(12) United States Patent
Ma et al.

(10) Patent No.: US 7,592,361 B2
(45) Date of Patent: Sep. 22, 2009

(54) INDOLE ACETIC ACID DERIVATIVES AND THEIR USE AS PHARMACEUTICAL AGENTS

(75) Inventors: Xin Ma, Bethany, CT (US);
Louis-David Cantin, Hamden, CT (US);
Soongyu Choi, Skillman, NJ (US);
Roger Clark, Lexington, MA (US);
Martin Hentemann, Hamden, CT (US);
Joachim Rudolph, Guilford, CT (US);
Rico Lavoie, Cheshire, CT (US);
Zhonghua Zhang, Derby, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 296 days.

(21) Appl. No.: 10/555,024

(22) PCT Filed: Apr. 28, 2004

(86) PCT No.: PCT/US2004/012959

§ 371 (c)(1),
(2), (4) Date: Oct. 26, 2005

(87) PCT Pub. No.: WO2004/098498

PCT Pub. Date: Nov. 18, 2004

(65) Prior Publication Data

US 2006/0264486 A1  Nov. 23, 2006

Related U.S. Application Data

(60) Provisional application No. 60/466,143, filed on Apr. 28, 2003.

(51) Int. Cl.
*A61K 31/425*  (2006.01)
*A61K 31/42*  (2006.01)
*C07D 417/00*  (2006.01)
*C07D 277/20*  (2006.01)
*C07D 498/00*  (2006.01)
*C07D 263/30*  (2006.01)

(52) U.S. Cl. .................. 514/365; 514/367; 514/374; 514/375; 548/159; 548/202; 548/224; 548/235

(58) Field of Classification Search .............. 514/365, 514/367, 374, 375; 548/159, 202, 224, 235
See application file for complete search history.

(56) References Cited

U.S. PATENT DOCUMENTS 5,916,908 A    6/1999  Giese et al.
6,187,805 B1 *  2/2001  Pineiro et al. ............... 514/415

FOREIGN PATENT DOCUMENTS

WO        9950268         7/1999
WO        0032180         8/2000
WO   WO 02/060438    *   8/2002   .................. 548/200

* cited by examiner

*Primary Examiner*—Kamal A Saeed
*Assistant Examiner*—Samantha L Shterengarts
(74) *Attorney, Agent, or Firm*—Myers Bigel Sibley & Sajovec, PA

(57) ABSTRACT

This invention is directed to indole acetic acid derivatives and their use in pharmaceutical compositions for the treatment of diseases such as diabetes, obesity, hyperlipidemia, and atherosclerotic disease. The invention is also directed to intermediates useful in preparation of indole acetic derivatives and to methods of preparation.

20 Claims, No Drawings

INDOLE ACETIC ACID DERIVATIVES AND THEIR USE AS PHARMACEUTICAL AGENTS

This application claims benefit of U.S. Provisional Application Ser. No. 60/466,143, filed Apr. 28, 2003, the contents of which are incorporated herein by reference in their entirety.

FIELD OF THE INVENTION

This invention is directed to indole acetic acid derivatives and their use in pharmaceutical compositions for the treatment of diseases such as diabetes, obesity, hyperlipidemia, and atherosclerotic disease. The invention is also directed to intermediates useful in preparation of indole acetic derivatives and to methods of preparation.

BACKGROUND OF THE INVENTION

Type 2 diabetes is the more common form of diabetes, with 90-95% of hyperglycemic patients experiencing this form of the disease. In type 2 diabetes, there appears to be a reduction in the pancreatic β-cell mass, several distinct defects in insulin secretion, and a decrease in tissue sensitivity to insulin. The symptoms and consequences of this form of diabetes include fatigue, frequent urination, thirst, blurred vision, frequent infections and slow healing of sores, diabetic nerve damage, retinopathy, micro and macro blood vessel damage, and heart and renal disease.

Resistance to the metabolic actions of insulin is one of the key features of type 2 diabetes. Insulin resistance is characterized by impaired uptake and utilization of glucose in insulin-sensitive target organs, for example, adipocytes and skeletal muscle, and by impaired inhibition of hepatic glucose output. Functional insulin deficiency, insulin resistance in the periphery, and the failure of insulin to suppress hepatic glucose output results in fasting hyperglycemia. Pancreatic β-cells compensate for the insulin resistance by secreting increased levels of insulin. However, the β-cells are unable to maintain this high output of insulin, and eventually, the glucose-induced insulin secretion falls, leading to the deterioration of glucose homeostasis and to the subsequent development of overt diabetes. Hyperinsulinemia is also linked to insulin resistance, hypertriglyceridemia, low high-density lipoprotein (HDL) cholesterol, and increased plasma concentration of low-density lipoproteins (LDL). The association of insulin resistance and hyperinsulinemia with these metabolic disorders has been termed "Syndrome X," and has been strongly linked to an increased risk of hypertension and coronary artery disease.

Obesity is an excessive accumulation of adipose tissue. Excess adipose tissue is associated with the development of serious medical conditions, for example, type 2 diabetes, hypertension, coronary artery disease, hyperlipidemia, obesity, and certain malignancies. The adipocyte may also influence glucose homeostasis through the production of tumor necrosis factor α (TNFα) and other molecules.

Atherosclerotic disease is known to be caused by a number of factors, for example, hypertension, diabetes, low levels of HDL, and high levels of LDL. Atherosclerotic-related diseases include cardiovascular disease, coronary heart disease (CHD), cerebrovascular disease, and peripheral vessel disease. Coronary heart disease includes CHD death, myocardial infarction, and coronary revascularization. Cerebrovascular disease includes ischemic or hemorrhagic stroke, and transient ischemic attacks.

Accordingly, despite the presence of some pharmaceuticals that are used to treat these diseases, there remains a need for new pharmaceuticals that are both safe and effective agents for the treatment of disease, and for useful methods to prepare them.

The present invention relates to compounds which are useful in the treatment of diabetes and related disorders such as Syndrome X, impaired glucose tolerance, impaired fasting glucose, and hyperinsulinemia; obesity; atherosclerotic disease, dyslipidemia, and related disorders such as hypertriglyceridemia, low HDL cholesterol, and hypercholesteremia; cardiovascular disease; and cerebrovascular disease.

DESCRIPTION OF THE INVENTION

The invention provides indole acetic acid derivatives of Formula (Ia) and Formula (Ib)

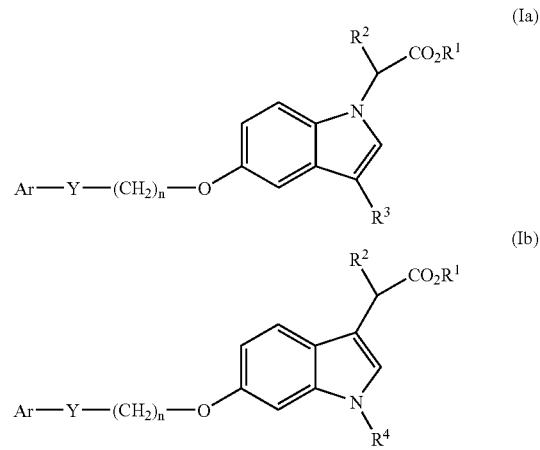

wherein $R^1$ is H, $C_1$-$C_6$ alkyl, or benzyl;

$R^2$ is H or $C_1$-$C_6$ alkyl;

$R^3$ is H or $C_1$-$C_4$ alkyl;

$R^4$ is H, $C_1$-$C_4$ alkyl, or $C_1$-$C_4$ acyl;

Y is O or $NR^5$;

$R^5$ is H or $C_1$-$C_6$ alkyl optionally substituted with $C_3$-$C_6$ cycloalkyl;

n is 2, 3, or 4;

Ar is a ring radical selected from phenyl and a 6-membered heteroaryl ring containing up to three N atoms,
 said Ar being optionally substituted at any available position by 1 to 5 independently selected $R^6$ groups, and
 optionally fused to a 5- or 6-membered saturated carbocyclic ring,
  a 5- or 6-membered unsaturated carbocyclic ring, or
  a 5- or 6-membered heterocyclic ring containing up to 3 additional heteroatoms selected from N, O, and S,
  wherein said fused ring may be optionally substituted at any available position by 1-4 independently selected $R^7$ groups;

$R^6$ is selected from the group
 OH,
 SH,
 halo,
 CN,
 $NO_2$,
 C(=O)OH,
 C(=O)—$OC_1$-$C_6$ alkyl, C(=O)—OC$_3$-C$_6$ cycloalkyl,
NR$^8$R$^9$,
C(=O)NR$^8$R$^9$,
C(=S)NR$^8$R$^9$,
C$_1$-C$_6$ alkyl optionally substituted with halo, OH, NR$^8$R$^9$, or C$_1$-C$_6$ alkoxy,
C$_1$-C$_6$ haloalkyl,
C$_1$-C$_6$ alkoxy,
C$_1$-C$_6$ thioalkyl,
C$_2$-C$_6$ alkenyl,
C$_1$-C$_6$ haloalkoxy,
C$_3$-C$_6$ cycloalkyl,
C$_3$-C$_6$ cycloalkoxy,
phenoxy optionally substituted on the phenyl ring with halo, C$_1$-C$_6$ alkyl, or C$_1$-C$_6$ alkoxy, and
a mono or bicyclic ring radical selected from the group consisting of phenyl optionally fused to
  a 5- or 6-membered saturated or partially unsaturated carbocyclic ring, or
  a 5- or 6-membered saturated or partially unsaturated heterocyclic ring containing from 1-3 heteroatoms selected from N, O, and S, and
a 5- or 6-membered heterocyclic ring radical containing up to 4 heteroatoms selected from N, O, or S, optionally fused to
  a 5- or 6-membered saturated or partially unsaturated carbocyclic ring, or
  a 5- or 6-membered saturated or partially unsaturated heterocyclic ring containing from 1-3 heteroatoms selected from N, O, and S,
said mono or bicyclic ring radical being optionally substituted with up to 5 of the following groups
halo,
hydroxy,
oxo,
CN,
C$_1$-C$_6$ alkyl optionally substituted with halo, OH, NR$^8$R$^9$, or C$_1$-C$_6$ alkoxy,
C$_1$-C$_6$ haloalkyl,
C$_1$-C$_6$ alkoxy,
C$_1$-C$_6$ thioalkyl
C$_1$-C$_6$ haloalkoxy,
C$_3$-C$_6$ cycloalkyl,
C$_3$-C$_6$ cycloalkoxy,
C$_1$-C$_6$ acyl,
C(=O)OH,
CH$_2$C(=O)OH,
NR$^8$R$^9$
C(=O)NR$^8$R$^9$,
C(=O)OC$_1$-C$_6$ alkyl, and
C(=O)OC$_3$-C$_6$ cycloalkyl;
R$^7$ is selected from the group
oxo,
hydroxy,
halo,
CN,
NR$^8$R$^9$,
C$_1$-C$_6$ alkyl optionally substituted with OH, NR$^8$R$^9$, or C$_1$-C$_6$ alkoxy,
C$_1$-C$_6$ haloalkyl,
C$_1$-C$_6$ alkoxy,
C$_1$-C$_6$ thioalkyl,
C$_1$-C$_6$ haloalkoxy,
C$_3$-C$_6$ cycloalkyl, and
C$_3$-C$_6$ cycloalkoxy;

R$^8$ and R$^9$ are independently selected from
H,
C$_1$-C$_6$ alkyl optionally substituted with C$_3$-C$_6$ cycloalkyl,
C$_1$-C$_6$ acyl,
benzyl optionally substituted with halo, C$_1$-C$_6$ alkoxy, (C$_1$-C$_6$)alkyl, CN, NH$_2$, N[(C$_1$-C$_3$)alkyl]$_2$, NO$_2$, or CF$_3$,
C$_3$-C$_6$ cycloalkyl, and
phenyl optionally substituted with halo, C$_1$-C$_6$ alkoxy, (C$_1$-C$_6$)alkyl, CN, NH$_2$, N[(C$_1$-C$_3$)alkyl]$_2$, NO$_2$, or CF$_3$, or
R$^8$ and R$^9$ may be taken together with the nitrogen atom to which they are attached to form a 5- or 6-membered heterocyclic ring optionally interrupted by NR$^5$ or O;

or the pharmacologically acceptable esters and salts thereof.

Definitions

The terms identified above have the following meaning throughout:

The term "halo" means F, Cl, Br, or I.

The terms "C$_1$-C$_3$ alkyl," "C$_1$-C$_4$ alkyl," and "C$_1$-C$_6$ alkyl" mean a straight or branched saturated hydrocarbon carbon chain of from 1 to about 3 carbon atoms, from 1 to about 4 carbon atoms, or from 1 to about 6 atoms, respectively. Examples of such groups include, but are not limited to, methyl, ethyl, isopropyl, sec-butyl, 2-methylpentyl, n-hexyl, and the like.

The term "C$_2$-C$_6$ alkenyl" means a straight or branched unsaturated hydrocarbon carbon chain of from 2 to about 6 carbon atoms. Examples of such groups include, but are not limited to, vinyl, allyl, isopropenyl, 2-butenyl, 3-ethyl-2-butenyl, 4-hexenyl, and the like.

The term "C$_1$-C$_6$ haloalkyl" means a C$_1$-C$_6$ alkyl group substituted by 1 to 3 halogen atoms or fluorine up to the perfluoro level. Examples of such groups include, but are not limited to, trifluoromethyl, tetrafluoroethyl, 1,2-dichloropropyl, 5-bromopentyl, 6-iodohexyl, and the like.

The term "C$_3$-C$_6$ cycloalkyl" means a saturated carbocyclic ring system of from 3 to about 6 carbon atoms. Examples of such groups include, but are not limited to, cyclopropyl, cyclobutyl, cyclopentyl, cyclohexyl, and the like.

The terms "C$_1$-C$_4$ acyl" and "C$_1$-C$_6$ acyl" means a linear or branched saturated carbon group having from about 1 to about 4 C atoms or from about 1 to about 6 C atoms, respectively, said carbon group being attached to the core molecule through the C atom of a C=O group. Examples of such groups include, but are not limited to, acetyl, propionyl, n-butanoyl, 2-methylpentantoyl, and the like The term "C$_1$-C$_6$ alkoxy" means a linear or branched saturated carbon group having from 1 to about 6 C atoms, said carbon group being attached to an O atom. The O atom is the point of attachment of the alkoxy substituent to the rest of the molecule. Such groups include, but are not limited to, methoxy, ethoxy, n-propoxy, isopropoxy, and the like.

The term "C$_1$-C$_6$ thioalkyl" means a linear or branched saturated carbon group having from 1 to about 6 C atoms, said carbon group being attached to an S atom. The S atom is the point of attachment of the thioalkyl substituent to the rest of the molecule. Such groups include, but are not limited to, methylthio, propylthio, hexylthio, and the like.

The term "C$_1$-C$_6$ haloalkoxy" means a C$_1$-C$_6$ alkoxy group further substituted on C with 1 to 3 halogen atoms or fluorine up to the perfluoro level.

The term "C$_3$-C$_6$ cycloalkoxy" means a C$_3$-C$_6$ cycloalkyl group attached to an O atom. The O atom is the point of attachment of the cycloalkoxy group with the rest of the molecule.

The term "phenoxy" means a phenyl group attached to an O atom. The O atom is the point of attachment of the phenoxy group to the rest of the molecule.

The term "6-membered heteroaryl ring" means a 6-membered monocyclic heteroaromatic ring radical containing 1-5 carbon atoms and up to the indicated number of N atoms. Examples of 6-membered heteroaryl rings include, but are not limited to, pyridyl, pyrimidyl, pyridazinyl, pyrazinyl, triazinyl, and the like.

The term "5- or 6-membered heterocyclic ring" means a 5 or 6-membered ring containing 1-5 C atoms and up to the indicated number of N, O and S atoms, and may be aromatic, partially saturated, or fully saturated.

When the 5- or 6-membered heterocyclic ring is attached to the rest of the molecule as a substituent, it becomes a radical. Examples of 5- or 6-membered heteroaryl ring radicals include, but are not limited to, furyl, pyrrolyl, thienyl, pyrazolyl, isoxazolyl, imidazolyl, oxazolyl, thiazolyl, isothiazolyl, triazolyl, thiadiazolyl, oxadiazolyl, pyridyl, pyrimidyl, pyridazinyl, pyrazinyl, triazinyl, and the like. Examples of partially unsaturated 5- or 6-membered heterocyclic ring radicals include, but are not limited to, dihydropyranyl, pyrrolinyl, pyrazolinyl, imidazolinyl, dihydrofuryl, and the like. Examples of saturated 5- or 6-membered heterocyclic ring radicals include, but are not limited to, pyrrolidinyl, tetrahydropyridyl, piperidinyl, morpholinyl, tetrahydrofuryl, tetrahydrothienyl, piperazinyl, and the like. The point of attachment of the radical may be from any available C or N atom of the ring to the rest of the molecule.

When the 5- or 6-membered heterocyclic ring is fused to another ring contained in the rest of the molecule, it forms a bicyclic ring. Examples of such 5- and 6-membered heterocyclic fused rings include, but are not limited to, pyrrolo, furo, pyrido, piperido, thieno, and the like. The point of fusion is at any available face of the heterocyclic ring and parent molecule.

Examples of compounds of Formulae (Ia) and (Ib) may be found in the preparative examples described below and in Table 1. The compounds described in the examples are intended to be representative of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

A salt of a compound of Formulae (Ia) or (Ib) may be prepared in situ during the final isolation and purification of a compound, or by separately reacting the purified compound in its free base form with a suitable organic or inorganic acid and isolating the salt thus formed. Likewise, when a compound of Formulae (Ia) or (Ib) contains a carboxylic acid moiety (e.g., $R^1$=$CH_2CO_2H$), a salt of said compound of Formulae (Ia) or (Ib) may be prepared by separately reacting it with a suitable inorganic or organic base and isolating the salt thus formed. The term "pharmaceutically acceptable salt" refers to a relatively non-toxic, inorganic or organic acid addition salt of a compound of the present invention (see, e.g., Berge, et al., J. Pharm. Sci. 66:1-19, 1977).

Representative salts of the compounds of Formulae (Ia) and (Ib) include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups in the conjugate base may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides; aralkyl halides like benzyl and phenethyl bromides, and the like.

The esters of Formulae (Ia) and (Ib) in the present invention are non-toxic, pharmaceutically acceptable esters, for example, alkyl esters such as methyl, ethyl, propyl, isopropyl, butyl, isobutyl, or pentyl esters. Additional esters such as, for example, methyl ester or phenyl-$C_1$-$C_5$ alkyl may be used. A compound of Formulae (Ia) or (Ib) may be esterified by a variety of conventional procedures including reacting the appropriate anhydride, carboxylic acid, or acid chloride with the alcohol group of the Formulae (Ia) or (Ib) compound. The appropriate anhydride may be reacted with the alcohol in the presence of a base to facilitate acylation such as 1,8-bis[dimethylamino]naphthalene or N,N-dimethylaminopyridine. An appropriate carboxylic acid may be reacted with the alcohol in the presence of a dehydrating agent such as dicyclohexylcarbodiimide, 1-[3-dimethylaminopropyl]-3-ethylcarbodiimide, or other water soluble dehydrating agents which are used to drive the reaction by the removal of water, and optionally, an acylation catalyst. Esterification may also be effected using the appropriate carboxylic acid in the presence of trifluoroacetic anhydride and optionally, pyridine, or in the presence of N,N-carbonyldiimidazole with pyridine. Reaction of an acid chloride with the alcohol may be carried out with an acylation catalyst such as 4-DMAP or pyridine.

One skilled in the art would readily know how to successfully carry out these as well as other methods of esterification of alcohols.

Additionally, sensitive or reactive groups on a compound of Formulae (Ia) or (Ib) may need to be protected and deprotected during any of the above methods for forming esters. Protecting groups in general may be added and removed by conventional methods well known in the art (see, e.g., T. W. Greene and P. G. M. Wuts, *Protective Groups in Organic Synthesis*; Wiley: New York, (1999)).

The compounds of Formulae (Ia) and (Ib) may contain one or more asymmetric centers, depending upon the location and nature of the various substituents desired. Asymmetric carbon atoms may be present in the (R) or (S) configuration. Preferred isomers are those with the absolute configuration which produces a compound of Formulae (Ia) or (Ib) with the more desirable biological activity. In certain instances, asymmetry may also be present due to restricted rotation about a given bond, for example, the central bond adjoining two aromatic rings of the specified compounds.

Substituents on a ring may also be present in either cis or trans form, and a substituent on a double bond may be present in either Z or E form.

It is intended that all isomers (including enantiomers and diastereomers), either by nature of asymmetric centers or by restricted rotation as described above, as separated, pure or partially purified isomers or racemic mixtures thereof, be included within the scope of the instant invention. The purification of said isomers and the separation of said isomeric mixtures may be accomplished by standard techniques known in the art.

The particular process to be utilized in the preparation of the compounds of this invention depends upon the specific compound desired. Such factors as the selection of the specific X moiety, and the specific substituents possible at various locations on the molecule, all play a role in the path to be followed in the preparation of the specific compounds of this invention. Those factors are readily recognized by one of ordinary skill in the art.

In general, the compounds used in this invention may be prepared by standard techniques known in the art, by known processes analogous thereto, and/or by the processes described herein, using starting materials which are either commercially available or producible according to routine, conventional chemical methods. The following preparative methods are presented to aid the reader in the synthesis of the compounds of the present invention.

General Methods of Preparation

Compounds of Formulae (Ia) and (Ib) can be prepared by the general methods outlined in the schemes below. Unless specifically defined otherwise, $R^1$-$R^9$, Y, n, and Ar have the meanings described above for the compounds of Formulae (Ia) and (Ib).

In Scheme 1, for example, compounds of Formula (Ia) can be prepared by either of the two routes illustrated. In Method A, a hydroxy or amino compound of Formula (II) is allowed to react with a substituted alkylene of Formula (III), optionally in the presence of a base, to provide the intermediate of Formula (IV). This compound is then allowed to react with the 5-hydroxyindole of Formula (V), optionally in the presence of base, to give the compound of the invention of Formula (Ia).

Alternatively, as shown in Method B, the reaction of the compound of Formula (VI) with a compound of Formula (VII), optionally in the presence of a base, gives an intermediate of Formula (VIII). This is allowed to react with the 5-hydroxyindole of Formula (V) under Mitsunobu conditions, (e.g., DEAD, TPP) to provide the compound of Formula (Ia).

Scheme 1
Preparation of Compounds of Formula (Ia)

A.

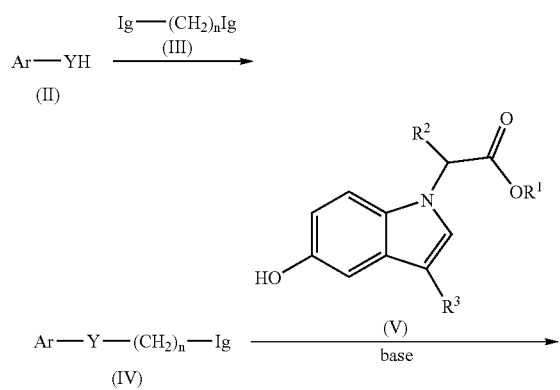

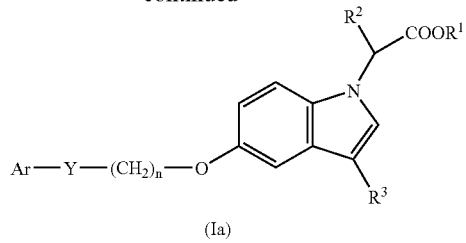

B.

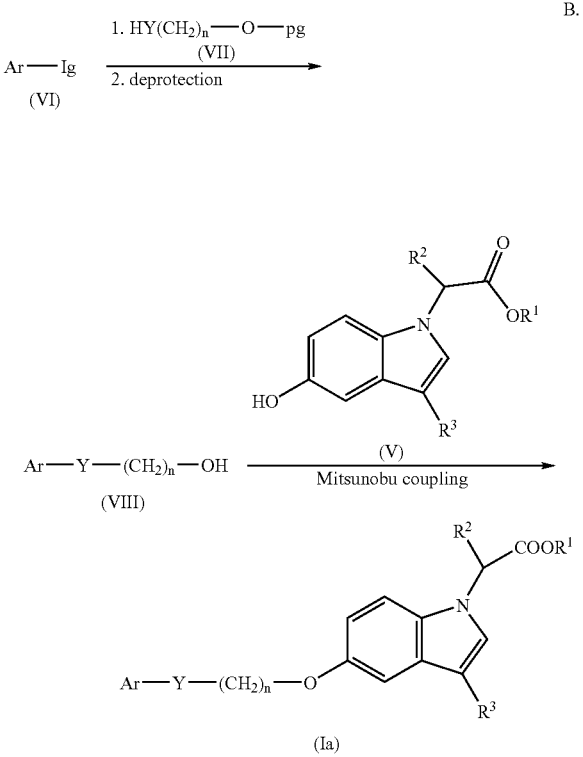

Ig = a leaving group (e.g., Br, OTs, etc.)
pg = a protecting grou (e.g., Ac, trityl, etc.)

In a similar fashion, compounds of Formula (Ib) can be prepared by analogous procedures illustrated in Scheme 2. In Method A, the previously described intermediate of Formula (IV) is allowed to react with the 6-hydroxyindole of Formula (IX) in the presence of a base such as cesium carbonate, to give the compound of Formula (Ib).

Alternatively, the intermediate of Formula (VIII), prepared as previously described, is allowed to react under Mitsunobu conditions (e.g., DEAD, TPP) to provide the compounds of Formula (Ib).

Scheme 2
Preparation of Compounds of Formula (Ib)

A.

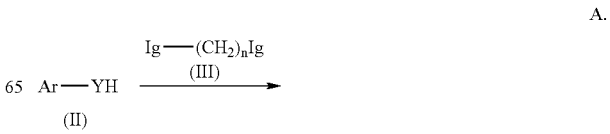

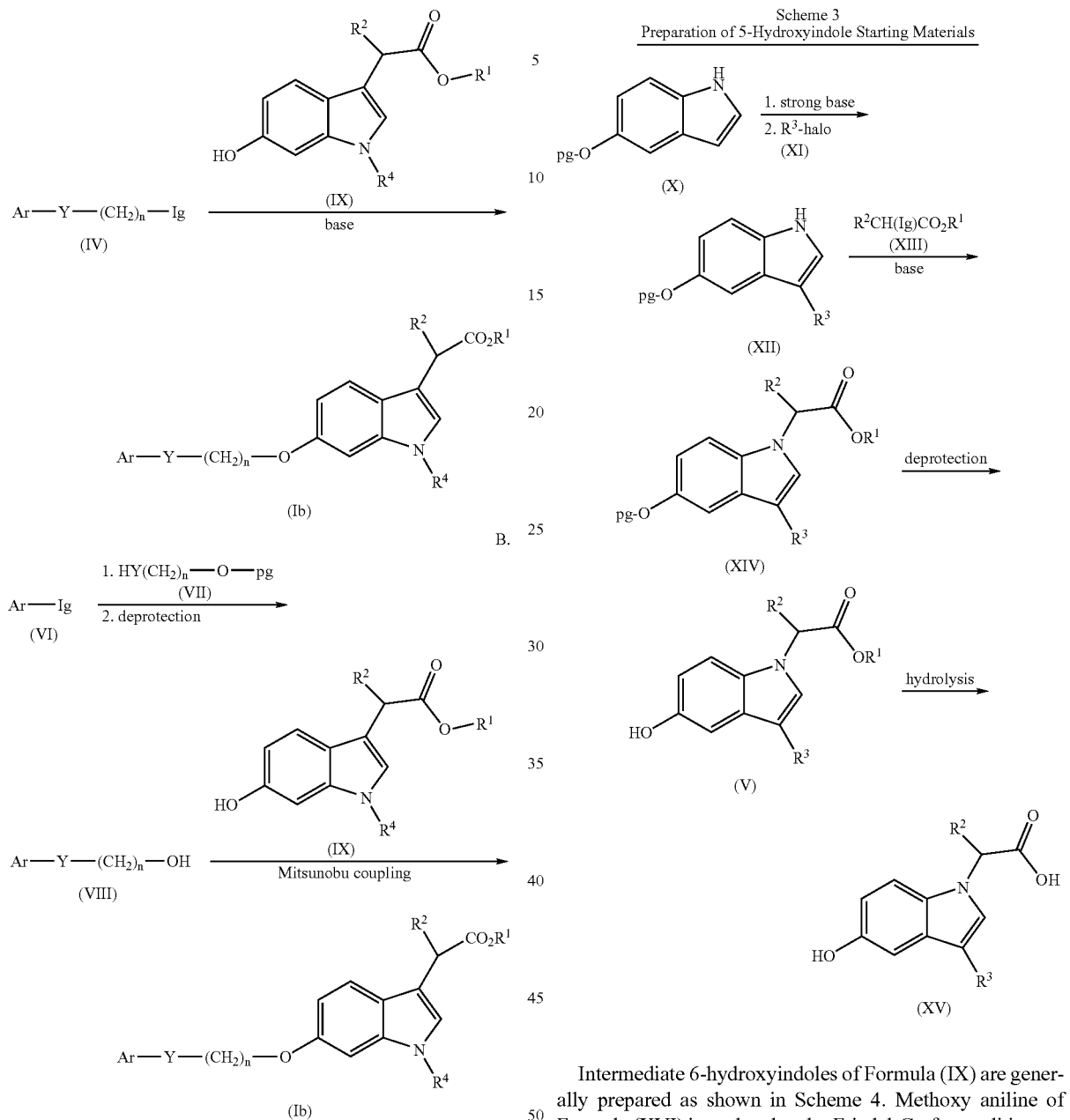

Intermediates that are not commercially available may be prepared by methods known in the art or methods analogous thereto. For example, 5-hydroxyindole intermediates of Formula (V) are generally prepared as shown in Scheme 3. The protected hydroxyindole is allowed to react with a strong base, such as an alkyl magnesium halide, followed by an alkyl halide of Formula (XI) [where hal is I, Br, or Cl] to provide the 3-alkylsubstituted indole of Formula (XII). N-alkylation of (XII) with a compound of Formula (XIII) in the presence of base provides the intermediate of Formula (XIV). Deprotection of (XIV) gives the compound of Formula (V). If desired, compounds of Formula (V) where $R^1$ is $C_1$-$C_6$ alkyl, may be hydrolyzed to the corresponding acid compounds of Formula (XV) [(V) where $R^1$ is H].

Intermediate 6-hydroxyindoles of Formula (IX) are generally prepared as shown in Scheme 4. Methoxy aniline of Formula (XVI) is acylated under Friedel-Crafts conditions to give, upon workup, the amino chloroacetophenone of Formula (XVII). Alkylation of the amine group of Formula (XVII) using a reagent of Formula (XVIII), such as dimethyl sulfate, optionally in the presence of a base, provides the intermediate of Formula (XIX). Ring closure of (XIX) with a base such as sodium hydride give the indolinone of Formula (XX). Reaction of (XX) with a Wadsworth-Emmons reagent of Formula (XXI) gives the indole acetic acid derivative of Formula (XXII). Demethylation of (XXII) by standard methods (e.g., $BBr_3$) provides the desired 6-hydroxyindole intermediate of Formula (IX). Hydrolysis of a Formula (IX) compound where $R^1$ is $C_1$-$C_6$ alkyl may be carried out, if desired, under standard conditions to provide the corresponding carboxylic acid compound of Formula (XXIII) [Formula (IX) where $R^1$ is H].

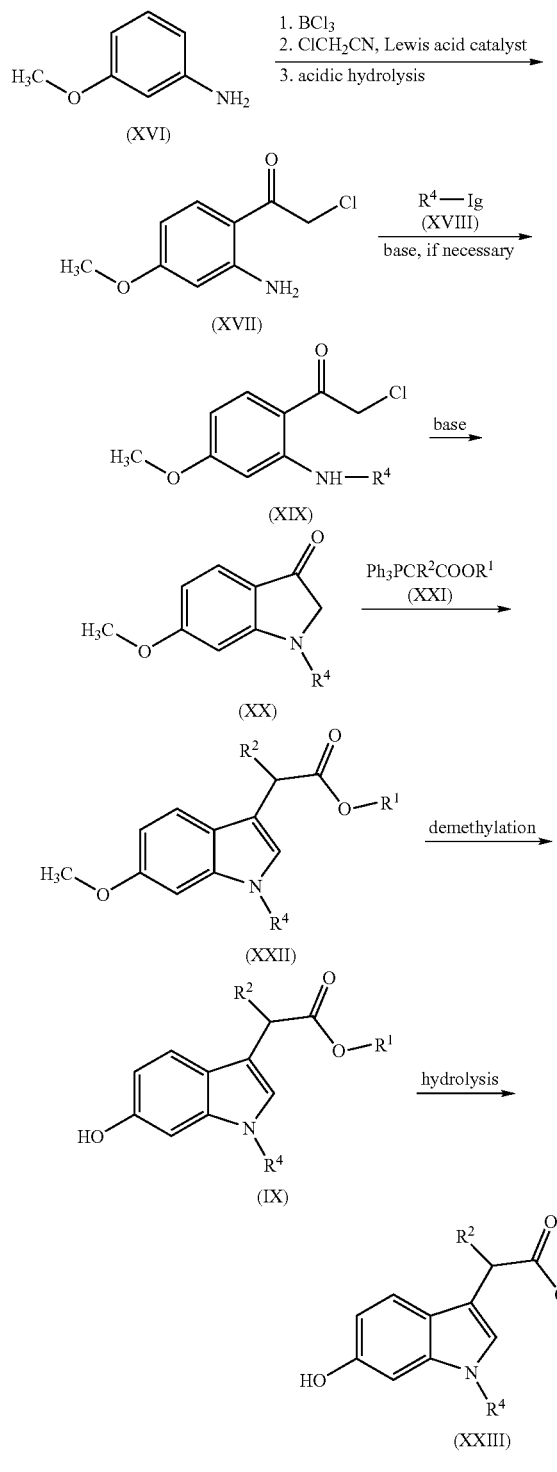

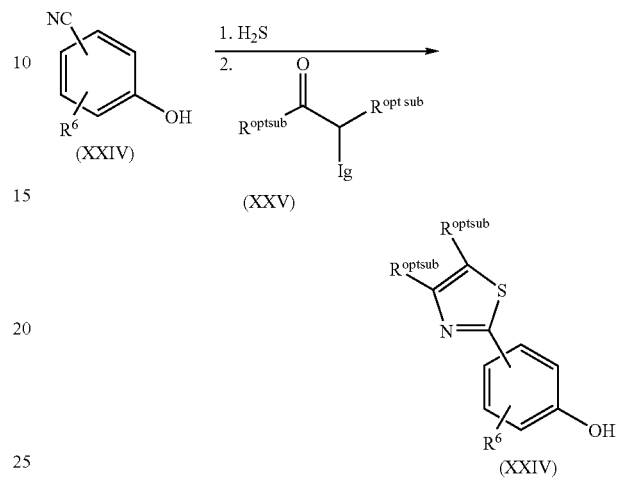

cally an alpha-haloketone of Formula (XXV), to give the phenol of Formula (XXVI) [(II), where Ar is phenyl, Y is O, and one $R^6$ is an optionally substituted thiazolyl radical].

The preparation of intermediates of Formula (II) where Ar is phenyl, Y is O, and $R^6$ is a thiazolyl ring, is described in PCT/US03/40842, incorporated by reference herein, and is further illustrated in Schemes 5 and 6. In Scheme 5, a cyanophenol of Formula (XXIV) is allowed to react sequentially with $H_2S$ and an appropriately substituted ketone, typically an alpha-haloketone of Formula (XXV), to give the phenol of Formula (XXVI) [(II), where Ar is phenyl, Y is O, and one $R^6$ is an optionally substituted thiazolyl radical].

Similarly, in Scheme 6, Formula (II) compounds in which Ar is phenyl, Y is O, and one $R^6$ group is an optionally substituted oxazole is prepared as shown in Scheme 6, also starting from the cyanophenol of Formula (XXIV). Basic peroxide hydrolysis of (XXIV) gives the amide of Formula (XXVII); reaction with the ketone of Formula (XXV) gives the desired intermediate of Formula (XXVIII) [(II), where Ar is phenyl, Y is O, and one $R^6$ is an optionally substituted oxazolyl radical].

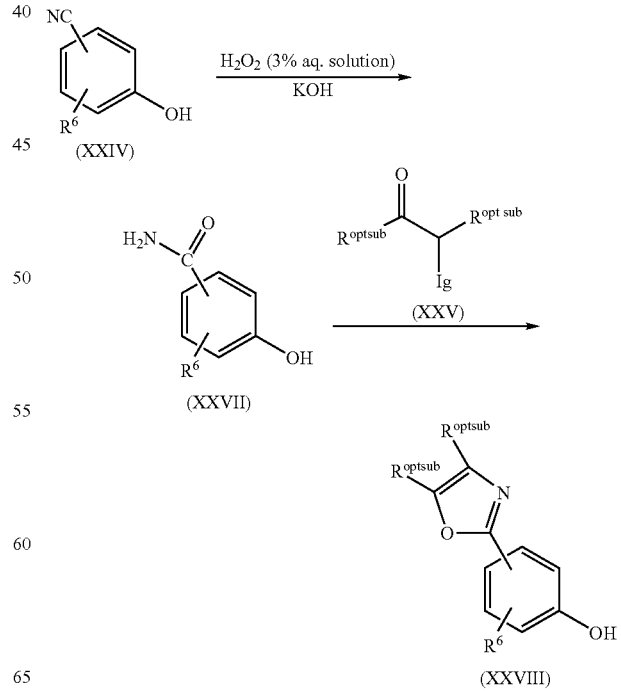

The chemistry described in Schemes 5 and 6 may also be carried out on appropriately substituted Formulae (Ia) and (Ib) compounds, namely Formulae (Ia) or (Ib) in which one of the $R^6$ substituents is cyano. An example of such transformation is shown in Scheme 7. The compound of Formula (XXIX) [(Ia) where $R^6$ substituent is cyano] is subjected to sequental treatment with $H_2S$, a ketone of Formula (XXV), and basic hydrolysis to give the Formula (XXX) compound [(Ia) where $R^6$ is an optionally substituted thiazolyl radical and $R^1$ is H].

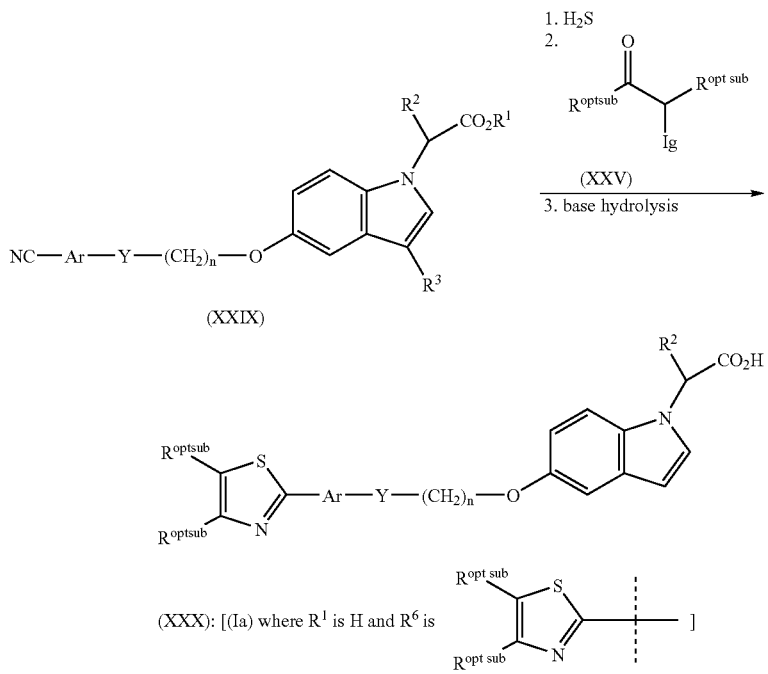

Preparation of Formulae (Ia) and (Ib) compounds in which $R^6$ is a mono or bicyclic ring radical may be prepared from the respective Formulae (Ia) and (Ib) compounds in which $R^6$ is halo. An example is illustrated in Scheme 8, in which a compound of Formula (XXXI) [(Ia) where $R^6$ is Cl] is allowed to react with a boronic acid or boronic ester under Suzuki conditions [base and Pd catalyst such as $PdCl_2(dppf)$] to give, after hydrolysis, the compound of Formula (XXXIII) [(Ib) where $R^6$ is an optionally substituted mono or bicyclic ring radical and $R^1$ is H].

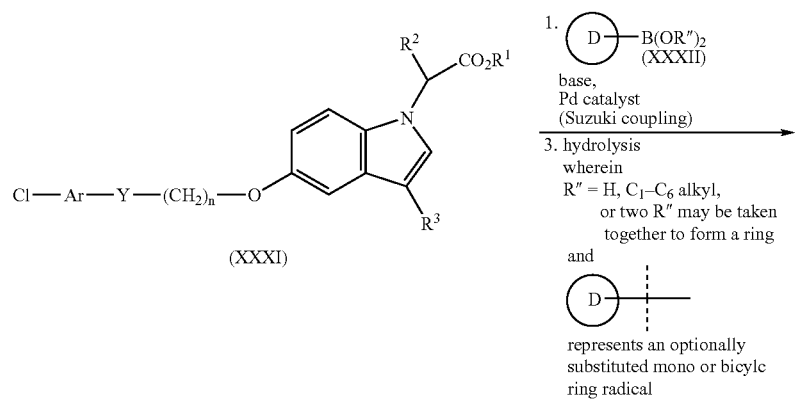

-continued

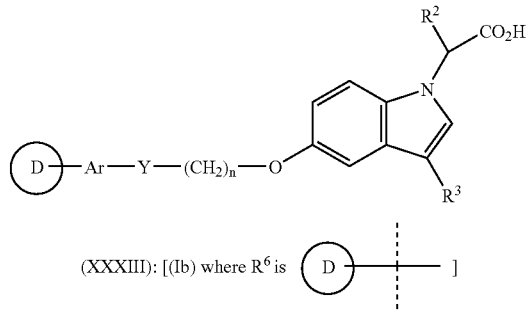

(XXXIII): [(Ib) where $R^6$ is D— ]

By a using the above schemes, alone or in combination, and preparative methods known in the art, compounds of the present invention can be made. The following experimental examples are presented to illustrate the invention described herein, but should not be construed as limiting the scope of the invention in any way.

Experimental Procedures

Air and moisture sensitive liquids and solutions were transferred via syringe or cannula, and introduced into reaction vessels through rubber septa. Commercial grade reagents and solvents were used without further purification. The term "concentration under reduced pressure" refers to use of a Buchi rotary evaporator at approximately 15 mm of Hg. All temperatures are reported uncorrected in degrees Celsius (° C.). Thin layer chromatography (TLC) was performed on EM Science pre-coated glass-backed silica gel 60 A F-254 250 μm plates. Column chromatography (flash chromatography) was performed on a Biotage system using 32-63 micron, 60 A, silica gel pre-packed cartridges. Purification using preparative reversed-phase HPLC chromatography were accomplished using a Gilson 215 system and a YMC Pro-C18 AS-342 (150×20 mm I.D.) column. Typically, the mobile phase used was a mixture of $H_2O$ (A) and MeCN (B). The water could be mixed or not with 0.1% TFA. A typical gradient was:

| Time [min.] | A: % | B: % | Flow [mL/min.] |
| --- | --- | --- | --- |
| 0.50 | 90.0 | 10.0 | 1.0 |
| 11.00 | 0.0 | 100.0 | 1.0 |
| 14.00 | 0.0 | 100.0 | 1.0 |
| 15.02 | 100.0 | 0.0 | 1.0 |

Unless otherwise specified, chiral analytical HPLC experiments were performed using one the two following methods using a Varian Pro Star 1200:
 A: Column: Chiracel AD, 4.6 (I.D.)×250 mm
 Mobile Phase: A: 0.1% TFA in hexanes; B: 0.1% TFA in i-PrOH;
 Isocratic: 95% A (5% B), 20 min.
 Flow Rate: 1.5 mL/min
 Detector (UV): 284 nm
 B: Column: Chiracel AD, 4.6 (I.D.)×250 mm
 Mobile Phase: A: 0.1% TFA in hexanes; B: 0.1% TFA in i-PrOH
 Isocratic: 95% A (5% B), 25 min.

Flow Rate: 1.0 mL/min
Detector (UV): 284 nm
Electron impact mass spectra (EI-MS or GC-MS) were obtained with a Hewlett Packard 5989A mass spectrometer equipped with a Hewlett Packard 5890 Gas Chromatograph with a J & W DB-5 column (0.25 μM coating; 30 m×0.25 mm). The ion source was maintained at 250° C. and spectra were scanned from 50-800 amu at 2 sec per scan. High pressure liquid chromatography-electrospray mass spectra (LC-MS) were obtained using a Hewlett-Packard 1100 HPLC equipped with a quaternary pump, a variable wavelength detector set at 254 nm, a YMC pro C-18 column (2×23 mm, 120 A), and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% to 95% B over 3.5 minutes at a flowrate of 1.0 mL/min was used with an initial hold of 0.5 minutes and a final hold at 95% B of 0.5 minutes. Total run time was 6.5 minutes. For consistency in characterization data, the retention time (RT) is reported in minutes at the apex of the peak as detected by the UV-Vis detector set at 254 nm.

Routine one-dimensional NMR spectroscopy was performed on 300 or 400 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate residual solvent signals, such as 2.49 ppm for DMSO-$d_6$, 1.93 ppm for $CD_3CN$, 3.30 ppm for $CD_3OD$, 5.32 ppm for $CD_2Cl_2$, and 7.26 ppm for $CDCl_3$ for $^1H$ NMR spectra, and 39.5 ppm for DMSO-$d_6$, 1.3 ppm for $CD_3CN$, 49.0 ppm for $CD_3OD$, 53.8 ppm for $CD_2Cl_2$, and 77.0 ppm for $CDCl_3$ for $^{13}C$ NMR spectra. General methods of preparation are illustrated in the reaction schemes, and by the specific preparative examples that follow.

Abbreviations and Acronyms

When the following abbreviations are used throughout the disclosure, they have the following meaning:

| | |
| --- | --- |
| Ac | acetyl |
| AcOH | acetic acid |
| ADDP | 1,1'-[azodicarbonyl]dipiperidine |
| Boc | t-butoxycarbonyl |
| Bu | butyl |
| $CDCl_3$ | deuterochloroform |

-continued

| | |
|---|---|
| Celite ® | registered trademark of Celite Corp. brand of diatomaceous earth |
| CI | chemical ionization |
| d | doublet |
| dd | doublet of doublet |
| ddd | doublet of doublet of doublet |
| de | diastereomeric excess |
| DAST | (diethylamino) sulfur trifluoride |
| DEAD | diethyl azodicarboxylate |
| DIA | diisopropylamine |
| DIAD | diisopropyl azodicarboxylate |
| DMAP | 4-(N,N-dimethyl)amino pyridine |
| DME | dimethoxyethane |
| DMF | N,N-dimethyl formamide |
| DMSO | dimethylsulfoxide |
| DMSO-$d_6$ | dimethylsulfoxide-$d_6$ |
| DOWEX ® 66 | Dowex hydroxide, weakly basic anion, macroporous, 25-50 mesh |
| dppf | 1,1'-bis(diphenylphosphino)ferrocene |
| Drierite ® | anhydrous calcium sulfate (W. A. Hammond Drierite Co.) |
| ee | enantiomeric excess |
| EI | electron impact ionization |
| EI – MS | electron impact – mass spectrometry |
| Et | ethyl |
| EtOH | ethanol |
| EtOAc | ethyl acetate |
| EtSH | ethane thiol |
| g | gram |
| GC – MS | gas chromatography – mass spectrometry |
| h | hour(s) |
| $^1$H NMR | proton nuclear magnetic resonance |
| Hex | hexanes |
| HPLC | high performance liquid chromatography |
| LC-MS | liquid chromatography/mass spectroscopy |
| LDA | lithium diisopropylamide |
| m | multiplet |
| M | molar |
| m/z | mass over charge |
| Me | methyl |
| MeCN | acetonitrile |
| mg | milligram |
| MHz | megahertz |
| min | minute(s) |
| mol | mole |
| mmol | millimole |
| MS | mass spectrometry |
| N | normal |
| NMR | nuclear magnetic resonance |
| NaOAc | sodium acetate |
| Pd/C | palladium on carbon |
| PdCl$_2$(dppf)•CH$_2$Cl$_2$ | [1,1'-bis(diphenylphosphino)ferrocene] dichloropalladium (II) complex with dichloromethane (1:1) |
| Ph | phenyl |
| PPh$_3$ | triphenylphosphine |
| ppm | parts per million |
| psi | pounds per square inch |
| Pr | propyl |
| q | quartet |
| qt | quintet |
| quant. | quantitative |
| $R_f$ | TLC retention factor |
| rt | room temperature |
| RT | retention time (HPLC) |
| s | singlet |
| TBS | tert-butyldimethylsilyl |
| TBSCl | tert-butyldimethylsilyl chloride |
| TFA | trifluoroacetic acid |
| THF | tetrahydrofuran |
| TLC | thin layer chromatography |
| TMS | tetramethylsilane |
| TPP | triphenylphosphine |
| v/v | volume per unit volume |
| vol | volume |
| w/w | weight per unit weight. |

PREPARATIVE EXAMPLES

Method 1: Preparation of 5-Hydroxy-1-indole Derivatives

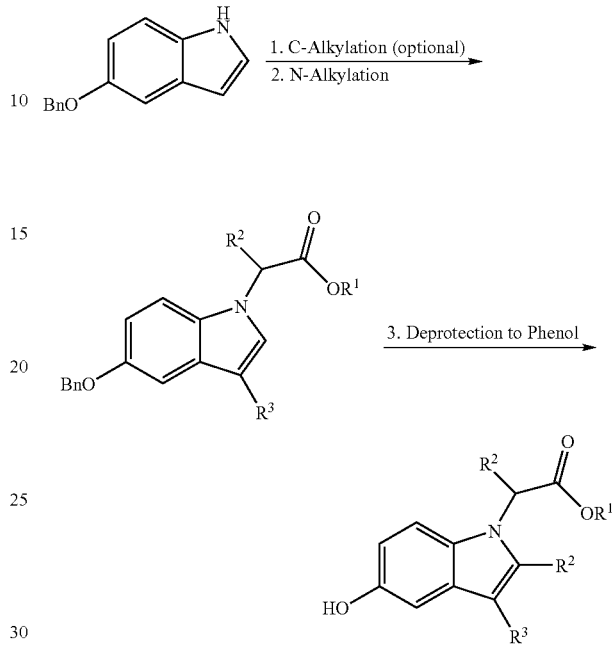

Step 1: C-Alkylation

Example 1

Preparation of 5-(benzyloxy)-3-methyl-1H-indole

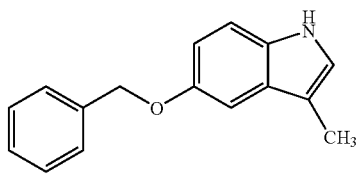

To a solution of 5-benzyloxyindole (19.8 g, 88.68·mmol) in THF (200 mL) pre-cooled with an ice bath, was added a 3.0 M solution of ethyl magnesium bromide in diethyl ether (44.3 mL, 133.02 mmol). The ice bath was removed and the resulting mixture was gradually warmed to rt over 5 h. The reaction mixture was cooled to 0° C. and iodomethane (37.8 g, 266.04 mmol) was added. The mixture was warmed to rt and stirred for 12 h. The reaction mixture was quenched by the addition of saturated aqueous ammonium chloride solution (50 mL). The reaction mixture was diluted with diethyl ether (150 mL), and then washed with water and a brine solution consecutively. The combined organic layers were dried over magnesium sulfate, filtered, and then concentrated via rotary evaporation to give a dark brownish solid. The crude mixture was purified on silica gel (95:5 hexane:dichloromethane) to give the title compound (12.6 g, 60%) as a brown solid. $^1$H NMR (400 MHz, CDCl$_3$) δ 7.79 (br s, 1H), 7.50 (d, 2H), 7.45 (m, 3H), 7.32 (s, 1H), 7.11 (d, 1H), 6.95 (m, 2H), 5.13 (s, 2H), 2.31 (s, 3H).

Example 2

Preparation of 5-(benzyloxy)-3-ethyl-1H-indole

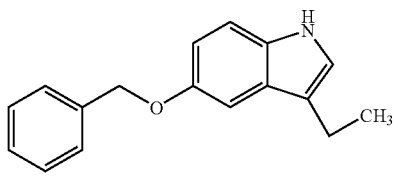

The title compound was prepared according to the method described in Example 1 substituting iodoethane for iodomethane. $^1$H NMR (CDCl$_3$) δ 7.79 (br s, 1H), 7.59 (d, 2H), 7.42 (m, 3H), 7.24 (m, 2H), 7.04 (d, 1H), 6.95 (m, 1H), 5.21 (s, 2H), 2.83 (q, 2H), 1.42 (t, 3H).

Step 2: N-Alkylation

Example 3

Preparation of 2-(5-benzyloxy-indol-1-yl)-propionic acid methyl ester

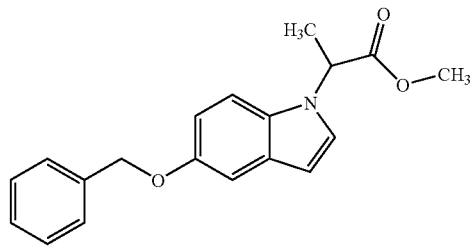

To a solution of 5-benzyloxyindole (13.5 g, 60.46 mmol) in DMF (300 mL) was added sodium hydride (60% dispersion in mineral oil, 3.63 g, 90.7 mmol). The resulting suspension was stirred at rt for 1 h after which methyl 2-bromopropionate (11.1 g, 66.51 mmol) was added. The resulting suspension was stirred at rt for 6 h. The reaction mixture was quenched with sat. aqueous ammonium chloride solution (25 mL), and diluted with 200 mL of EtOAc. The organic layer was washed with water three times. The aqueous layer was extracted again with EtOAc. The combined organic layers were dried over magnesium sulfate, filtered, and concentrated via rotary evaporation. The resulting brown oil was purified on silica gel (EtOAc/hexanes 1:1) to give the title compound as a brownish oil (15.3 g, 82%). LC/MS m/z 310 (M+H)$^+$, RT 4.04 min. $^1$H NMR (400 MHz, Acetone-d$_6$) δ 7.57 (d, 2H), 7.23-7.41 (m, 5H), 7.19 (d, 1H), 6.84 (d, 1H), 6.40 (d, 1H), 5.37 (q, 1H), 5.17 (s, 2H), 3.66 (s, 3H), 1.79 (d, 3H).

Example 4

Preparation of (R)-2-(5-benzyloxy-indol-1-yl)-propionic acid

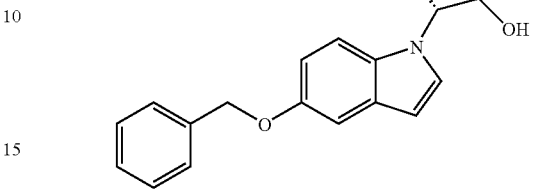

A suspension of 5-benzyloxyindole (105.29 g, 0.448 mol) and KOH (88.72 g, 1.344 mol) in DMSO (640.0 mL) was heated to ~120° C. and stirred for 25 minutes. The resulting dark colored solution was cooled to rt and then to 15-18° C. in an ice/water bath. To this mixture was added (S)-bromopropionic acid (46.47 mL, 0.515 mol) over 10 minutes, maintaining the temperature below 35° C. The resulting reaction mixture was stirred at ~30° C. for 1.5 h. The reaction was monitored by reverse phase HPLC. Upon completion, the reaction mixture was quenched by pouring into ice/water (1.2 L). The resulting mixture was extracted with ethyl acetate (2×500 mL, 1×250 mL). The combined organic layers were washed with water (3×500 mL), brine (350 mL), dried over anhydrous sodium sulfate, filtered, and concentrated to dryness to give 135 g of the crude product which was found to have an ee of ~80%. This mixture was purified by silica gel chromatography using a gradient of dichloromethane to 8% MeOH/dichloromethane giving 115 g of (R)-2-(5-benzyloxy-indol-1-yl)propionic acid, containing 10% of the (S)enantiomer.

This mixture was further enriched to give provide the (R) enantiomer in greater optical purity by the carrying out the following procedure:

The mixture was dissolved in dichloromethane/hexanes (294/294 mL) and stirred at rt for 2 days. The resulting racemic solid mixture was removed by filtration. The filtrate contained the desired enantiomer (90% ee). The filtrate was concentrated to dryness (at ~35° C.) to give 91 g of the desired product. The above precipitation process was repeated with dichloromethane/hexanes (273/575 mL). After filtration and washing with dichloromethane/hexanes (30 mL), the combined filtrates were concentrated to give 82.9 g of the desired product (95% ee). $^1$H NMR (400 MHz, DMSO-d$_6$) δ 7.43 (d, 2H), 7.38 (m, 3H), 7.30 (m, 2H), 7.13 (s, 1H), 6.82 (d, 1H), 6.38 (s, 1H), 5.25 (q, 1H), 5.08 (s, 2H), 1.70 (d, 3H); LC/MS (+esi) m/z 296.1 (M+H)$^+$, RT 3.06 min.

Chiral HPLC conditions for indole propionic acid: Column: Chiracel AD, 4.6 (I.D.)×250 mm; Mobile Phase: A: 0.1% TFA in Hexanes; B: 0.1% TFA in IPA; Gradient: 90-65% A (10-35% B) in 21 min.; Flow rate: 1.0 mL/min; Detector (UV): 284 nm; retention time of desired enantiomer: 13.09 min.

Reverse Phase HPLC conditions: Column: YMC-Pack ProC18 (AS-300), 50×4.6 mm (I.D.), S-5 μm, 12 nm (No. 040506614); Mobile Phase: A: 0.1% TFA in water; B: 0.1% TFA in acetonitrile; Gradient: 90-5% A (10-95% B) in 7 min.; Flow rate: 4.0 mL/min; Detector (UV): 220 nm. Retention time of title compound: 3.53 min.

The absolute stereoisomeric configuration of the target compound was determined by single crystal X-ray analysis of its R-α-methylbenzylamine salt.

Example 5

Preparation of [5-(benzyloxy)-1H-indol-1-yl]acetic acid methyl ester

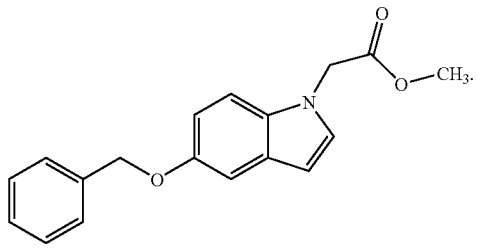

To a solution of 5-benzyloxyindole (1.67 g, 7.489 mmol) in DMF (50 mL) was added sodium hydride (60% dispersion in mineral oil, 389 mg, 9.735 mmol). The resulting suspension was stirred at rt for 1 h at which time methyl bromoacetate (1.26 g, 8.238 mmol) was added. The resulting solution was stirred at rt for 4.5 h. The reaction was quenched with sat. aqueous ammonium chloride solution (25 mL), and diluted with EtOAc (50 mL). The organic layer was washed three times with water. The aqueous layer was extracted with EtOAc again and the combined organic layers were dried over magnesium sulfate, filtered, and concentrated via rotary evaporation. The resulting brown oil was purified on silica gel (hexanes/EtOAc 1:1) to give the title compound as a brownish oil (1.64 g, 74%). LC/MS m/z 296 (M+H)+, RT 3.21 min; $^1$H NMR (400 MHz, CDCl$_3$) δ 7.35-7.37 (m, 2H), 7.23-7.30 (m, 3H), 7.02-7.08 (m, 2H), 6.95 (d, 1H), 6.87 (dd, 1H), 6.37 (dd, 1H), 5.01 (s, 2H), 4.72 (s, 2H), 3.64 (s, 3H).

Example 6

Preparation of 2-(5-benzyloxy-3-methyl-indol-1-yl)-propionic acid methyl ester

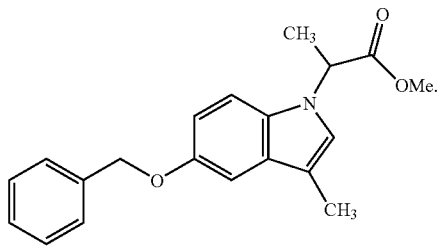

This compound was prepared according to the method outlined in Example 5, using the compound described in Example 1 and 2-bromoproprionate as starting materials. $^1$H NMR (400 MHz, CDCl$_3$) δ 7.55 (m, 2H), 7.46 (m, 3H), 7.24 (d, 1H), 7.19 (d, 1H), 7.08 (s, 1H), 7.03 (dd, 1H), 5.20 (s, 2H), 5.16 (1, 1H), 3.75 (s, 3H), 2.40 (s, 3H), 1.84 (d, 3H).

Step 3: Deprotection to Phenol

Example 7

Preparation of 2-(5-hydroxy-indol-1-yl)-propionic acid methyl ester

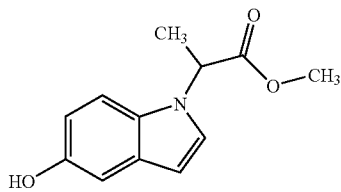

To a solution of 2-(5-benzyloxy-indol-1-yl)-propionic acid methyl ester (Example 3, 20.0 g, 64.7 mmol) in absolute ethanol (150 mL) was added Pd(OH)$_2$ (2.0 g, 10 wt %) suspended in ethanol (50 mL). Ammonium formate (8.1 g, 129.3 mmol) was added and the resulting mixture was heated to 60° C. for 4 h. The reaction mixture was cooled to rt and the palladium was filtered through a plug of silica gel. The filtrate was concentrated to give a light yellow oil which was used in the following step without further purification (13 g, 92%). LC/MS m/z 220 (M+H)+, RT 8.01 min; $^1$H NMR (400 MHz, acetone-d$_6$) δ 7.78 (br s, 1H), 7.28 (d, 1H), 7.20 (d, 1H), 6.97 (d, 1H), 6.77 (dd, 1H), 6.36 (d, 1H), 5.23 (q, 1H), 3.62 (s, 3H), 1.78 (d, 3H).

Example 8

Preparation of (R)-2-(5-hydroxy-indol-1-yl)-propionic acid methyl ester

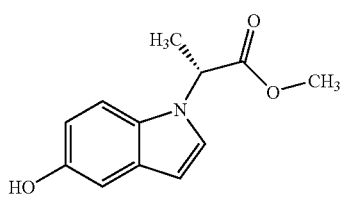

A suspension of (R)-2-(5-benzyloxy-indol-1-yl)-propionic acid (Example 4, 18.0 g, 0.061 mol), sodium bicarbonate (15.36 g, 0.183 mol), and iodomethane (11.40 mL, 0.183 mol) in DMF (164 mL) was stirred at rt for 20 h. The reaction was monitored by reverse phase HPLC. Upon completion, the reaction was quenched by pouring into ice/water (300 mL) followed by extracting with ethyl acetate (2×150 mL). The combined organic layer was washed with water (2×150 mL) and brine (150 mL) and was dried over anhydrous sodium sulfate. Filtration and concentration to dryness gave a crude oil which was purified by silica gel chromatography using 10-35% ethyl acetate/hexanes to give 16.38 g (87%) of (R)-2-(5-benzyloxy-indol-1-yl)-propionic acid methyl ester as an oil. $^1$H NMR (DMSO-d$_6$) δ 7.45 (d, 2H), 7.38 (m, 3H), 7.30 (m, 2H), 7.13 (s, 1H), 6.82 (d, 1H), 6.38 (s, 1H), 5.41 (q, 1H), 5.08 (s, 2H), 3.60 (s, 3H), 1.70 (d, 3H); LC/MS (+esi) m/z 310.2 (M+H)+, RT 3.47 min.

Reverse Phase HPLC conditions: Column: YMC-Pack ProC18 (AS-300), 50×4.6 mm (I.D.), S-5 μm, 12 nm (No. 040506614); Mobile Phase: A: 0.1% TFA in Water; B: 0.1% TFA in acetonitrile; Gradient: 90-5% A (10-95% B) in 7 min.; Flow rate: 4.0 mL/min; Detector (UV): 220 nm. Retention time for the title compound: 3.98 min.

A mixture of (R)-2-(5-benzyloxy-indol-1-yl)-propionic acid methyl ester (20.0 g, 0.065 mol) and palladium hydroxide (2.0 g, wet 20% Pd on carbon) in ethanol (340 mL) under argon was heated to 40° C. To this suspension was slowly added a solution of ammonium formate (5.04 g, 0.078 mol) in ethanol/water (110.5/9.6 mL). Fifteen percent (15%) of the solution was added initially over a period of 40 minutes to ensure that the reaction had initiated (indicated by reverse phase HPLC). The remaining solution was then slowly added over a period of 1.5 h. The reaction was monitored by reverse phase HPLC. Upon completion, the reaction mixture was cooled to rt and filtered through a silica gel pad. The pad was washed with ethanol. The combined fractions were concentrated to dryness under vacuum at 30° C. The crude product was purified by silica gel chromatography using a gradient of 5-35% ethyl acetate/hexanes to give 14.00 g (98%) of (R)-2-(5-hydroxy-indol-1-yl)-propionic acid methyl ester as an oil. Chiral HPLC indicated an ee value of the desired enantiomer as 95%. $^1$H NMR (400 MHz, DMSO-$d_6$) δ 8.70(s, 1H), 7.32 (s, 1H), 7.17 (d, 1H), 6.85 (s, 1H), 6.61 (d, 1H), 6.28 (d, 1H), 5.32 (q, 1H), 3.60 (s, 3H), 1.70 (d, 3H); LC/MS (+esi) m/z 220.1 (M+H)$^+$, RT 2.07 min.

Chiral HPLC conditions for phenol: Column: Chiracel AD, 4.6 (I.D.)×250 mm; Mobile Phase: A: 0.1% TFA in Hexanes; B: 0.1% TFA in IPA; Gradient: 90-50% A (10-50% B) in 26 min; Flow rate: 1.0 mL/min; Detector (UV): 284 nm. Retention time of the desired enantiomer: 20.45 min.

Reverse Phase HPLC conditions: Column: YMC-Pack ProC18 (AS-300), 50×4.6 mm (I.D.), S-5 μm, 12 nm (No. 040506614); Mobile Phase: A: 0.1% TFA in Water; B: 0.1% TFA in Acetonitrile; Gradient: 90-5% A (10-95% B) in 7 min; Flow rate: 4.0 mL/min; Detector (UV): 220 nm. Retention time of the title compound: 2.54 min.

Example 9

Preparation of methyl (5-hydroxy-1H-indol-1-yl)acetate

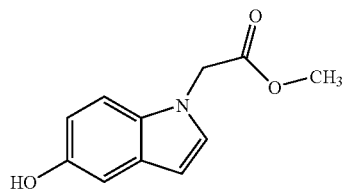

A solution of the compound prepared in Example 5 was treated as described in Example 7. LC/MS m/z 206 (M+H)$^+$, RT 1.68 min; $^1$H NMR (400 MHz, acetone-$d_6$) δ 6.98 (d, 1H), 6.95 (d, 1H), 6.92 (dd, 1H), 6.68 (dd, 1H), 6.33 (dd, 1H), 4.72 (s, 2H), 4.68 (br s, 1H), 3.65 (s, 3H).

Method 2: Preparation of 6-Hydroxy-1-indole Derivatives

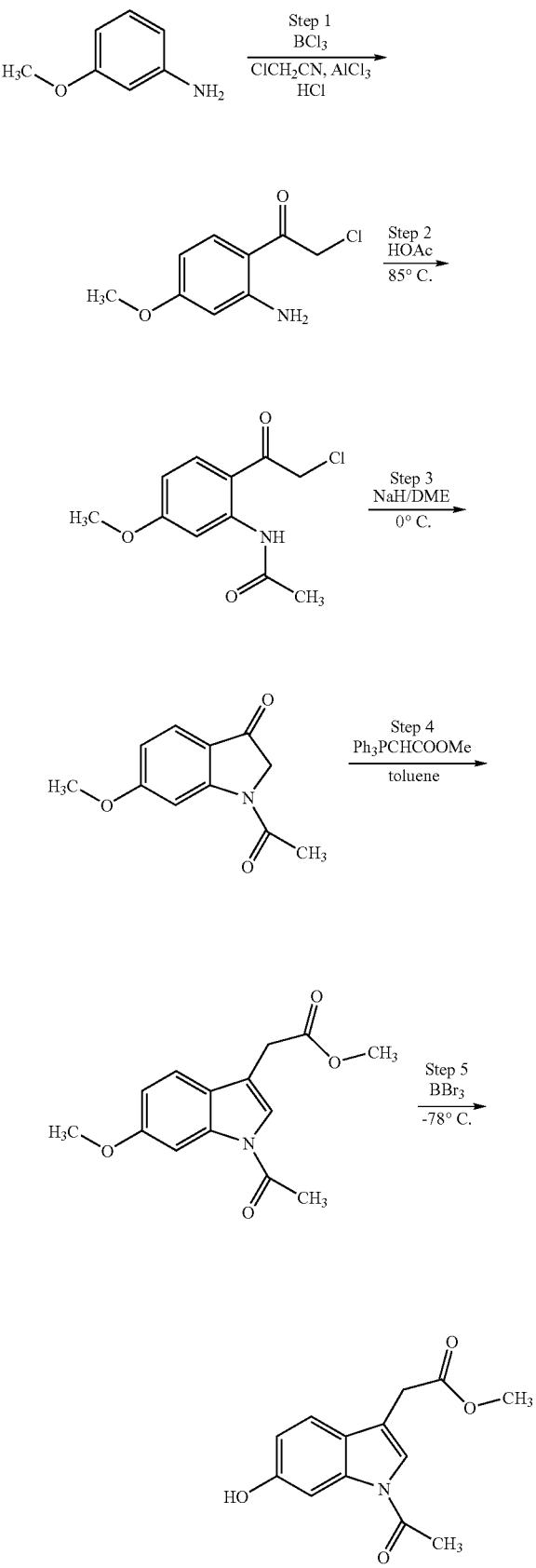

Step 1

Example 10

Preparation of
1-(2-amino-4-methoxyphenyl)-2-chloroethanone

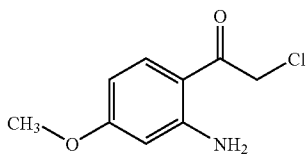

To 90 mL benzene cooled in an ice-water bath, was added 79.0 mL of a 1.0 M solution of BCl$_3$ (79.0 mmol) in dichloromethane, followed by the dropwise addition of a solution of m-anisidine (8.84 g, 71.78 mmol) in benzene (90 mL). To the resultant mixture was added chloroacetonitrile (6.50 g, 86.14 mmol), followed by AlCl$_3$ (10.53 g, 78.96 mmol). The reaction mixture was heated at reflux under argon for 5 h resulting in the formation of two layers. The reaction mixture was cooled to rt and 200 mL ice-cold 2N HCl solution was added. A yellow precipitate formed. The mixture was heated at 90° C. until the precipitate dissolved over about 1.5 h. The mixture was cooled to rt and extracted with dichloromethane and the organic layer was washed with water, dried over MgSO$_4$ and concentrated to yield a solid (9.93 g, 69%). $^1$H NMR showed minor impurities. The material was used without further purification. LC/MS m/z 200 (M+H)$^+$; $^1$H NMR (400 MHz, DMSO-d$_6$) δ 7.59 (d, 1H), 7.34 (bs, 2H), 6.23 (d, 1H), 6.11 (dd, 1H), 4.85 (s, 2H), 3.71 (s, 3H).

Step 2

Example 11

Preparation of
N-[2-(2-chloro-acetyl)-5-methoxy-phenyl]-acetamide

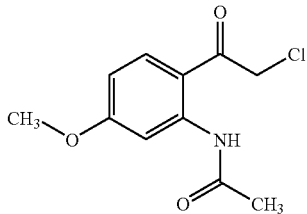

A solution of 1-(2-amino-4-methoxyphenyl)-2-chloroethanone (9.93 g, 49.74 mmol) (Example 10) in acetic acid (100 mL) was heated at 85° C. for 4 h. The solvent was evaporated under reduced pressure to yield a yellow solid (12.00 g, 100%). LC/MS m/z 242 (M+H)$^+$; $^1$H NMR (400 MHz, DMSO-d$_6$) δ 11.77 (s, 1H), 8.45 (d, 1H), 7.73 (d, 1H), 6.63 (dd, 1H), 4.71 (s, 2H), 3.89 (s, 3H), 2.25 (s, 3H).

Step 3

Example 12

Preparation of
1-acetyl-6-methoxy-1,2-dihydro-3H-indol-3-one

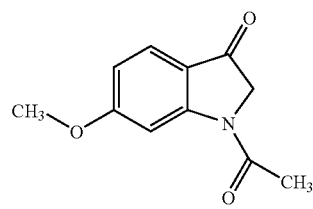

To a suspension of NaH (60% dispersion in mineral oil, 3.97 g, 99.3 mmol) in DME (75 mL) was added an ice-cold solution of N-[2-(chloroacetyl)-5-methoxyphenyl]acetamide (12.00 g, 49.7 mmol) (Example 11) in DME (165 mL) at 0° C. The mixture was stirred under argon for 15 minutes, then 2 N HCl (75 mL) solution was added slowly. The mixture was extracted with dichloromethane. The combined organic layers were dried over MgSO$_4$ and concentrated to yield a solid. The crude material was purified on silica gel eluting with EtOAc/hexane (1:1) and then EtOAc to give a reddish solid (7.87 g, 77%) with minor impurities: LC/MS m/z 206 (M+H)$^+$; $^1$H NMR (400 MHz, DMSO-d$_6$) δ 7.94 (d, 1H), 7.59 (d, 1H), 6.80 (dd, 1H), 4.51 (s, 2H), 3.85 (s, 3H), 2.24 (s, 3H).

Step 4

Example 13

Preparation of methyl
(1-acetyl-6-methoxy-1H-indol-3-yl)acetate

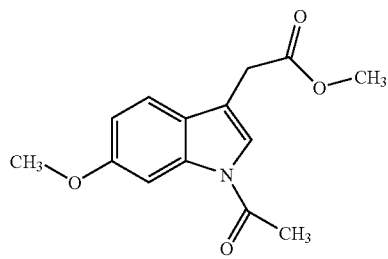

A mixture of 1-acetyl-6-methoxy-1,2-dihydro-3H-indol-3-one (3.96 g, 19.3 mmol) (Example 12) and methyl (triphenylphosphoranylidene)acetate (19.75 g, 57.9 mmol) in toluene (60 mL) was heated at reflux under argon for 24 h. The mixture was loaded on silica gel and eluted with EtOAc/hexane (1/5) to yield a thick oil (2.52 g, 50%). LC/MS m/z 262 (M+H)$^+$; $^1$H NMR (400 MHz, CDCl$_3$) δ 8.04 (br s, 1H), 7.38 (d, 1H), 7.31 (s, 1H), 6.92 (dd, 1H), 3.89 (s, 3H), 3.74 (s, 3H), 3.71 (d, 2H), 2.62 (s, 3H).

Step 5

Example 14

Preparation of methyl (1-acetyl-6-hydroxy-1H-indol-3-yl)acetate

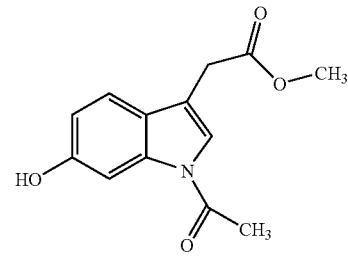

To a solution of methyl (1-acetyl-6-methoxy-1H-indol-3-yl)acetate (0.67 g, 2.56 mmol) (Example 13) in dichloromethane (10 mL) was added 1 M BBr$_3$ in dichloromethane (10.3 mL, 10.3 mmol) at −78° C. under argon. Stirring was continued at −78° C. for 1 h, at 0° C. for 3 h and at rt for 18 h consecutively. The reaction mixture was quenched with water and dichloromethane was added. Solid NaHCO$_3$ was added to adjust the pH of the mixture to 8. The mixture was extracted with CH$_2$Cl$_2$. The combined organic layers were dried over MgSO$_4$, filtered, and concentrated to yield a yellow solid (200.0 mg, 32%). LC/MS m/z 248 (M+H)$^+$; $^1$H NMR (400 MHz, DMSO-d$_6$) δ 9.42 (s, 1H), 7.77 (d, 1H), 7.52 (s, 1H), 7.28 (d, 1H), 6.71 (dd, 1H), 3.71 (s, 2H), 3.61 (s, 3H), 2.55 (s, 3H).

Method 3: Preparation of Naphthyl and Aryl Indole Derivatives

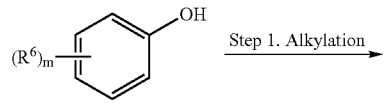

Step 1. Alkylation

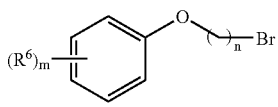

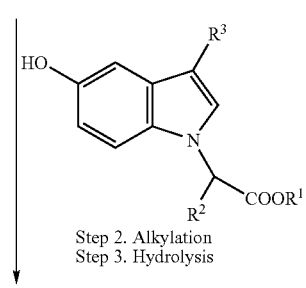

Step 2. Alkylation
Step 3. Hydrolysis

-continued

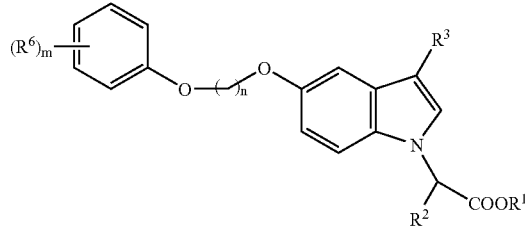

m = 1, 2, 3, 4, or 5

Step 1: Alkylation

Example 15

Preparation of 1,6-dibromo-2-(2-bromo-ethoxy)-naphthalene

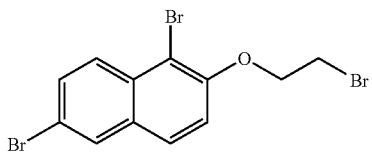

1,6-Dibromo-2-naphthol (15.0 g, 49.67 mmol) and 1,2-dibromoethane (46.7 g, 248.37 mmol) were added to a suspension of potassium carbonate (84.8 g, 74.51 mmol) in acetonitrile (500 mL) at rt. The reaction mixture was stirred for 48 h. Additional 1,2-dibromoethane (21.5 mL, 248.37 mmol) was added and the reaction mixture was stirred for 96 h at rt. The reaction mixture was cooled to 0° C. with an ice bath and filtered through a fritted glass funnel. The resulting filtrate was concentrated under reduced pressure to give the title compound (14.2 g, 69.9% yield) as a brown solid. GC/MS m/z 406 (M)$^+$, RT 10.25 min; $^1$H NMR (400 MHz, acetone-d$_6$) δ 14-8.09 (m, 2H), 7.96 (d, 1H), 7.71 (d, 1H), 7.54 (d, 1H), 4.64-4.60 (m, 2H), 3.90-3.86 (m, 2H).

Example 16

Preparation of 1-(2-bromo-ethoxy)-2-chloro-4-methyl-benzene

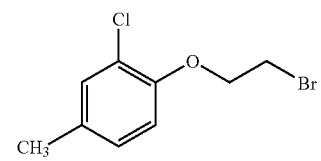

To a solution of 2-chloro-4-methylphenol (500 mg, 3.62 mmol) in acetonitrile (20 mL) was added 1,2-dibromoethane (3.29 g, 17.53 mmol) followed by cesium carbonate (2.28 g, 7.01 mmol). The resulting mixture was heated at 85° C. for 48 h, then cooled to rt. The solution was filtered through a Celite® pad. The Celite® was washed with acetone and the combined eluents were concentrated under reduced pressure to give the title compound as a white solid (697 mg, 76%). GC/MS (EI) m/z 248 (M)+, RT 7.33 min.

Example 17

Preparation of 4-bromo-1-(2-bromo-ethoxy)-2-chloro-benzene

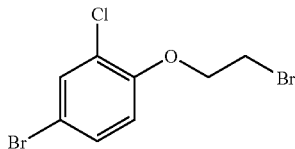

Using 4-bromo-2-chlorophenol as starting material, the title compound was prepared in a similar fashion as described in Example 16 to give a white solid (612 mg, 77%). GC/MS (EI) m/z 312 (M+), RT 8.11 min.

Example 18

Preparation of 2-(2-bromo-ethoxy)-5-methoxy-benzonitrile

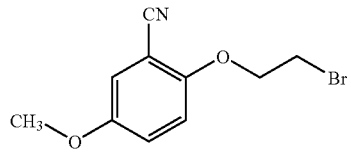

Using 2-cyano-4-methoxyphenol as starting material, the title compound was prepared in a similar fashion as described in Example 16 to give a white solid (837 mg, 93%) GC/MS (EI) m/z 255 (M)+, RT 4.49 min.

Example 19

Preparation of 1-(2-bromo-ethoxy)-2-methoxy-4-methyl-benzene

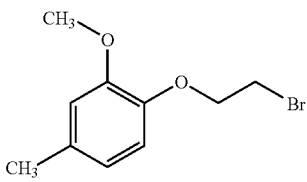

To a solution of 2-methoxy-4-methylphenol (1000 mg, 7.24 mmol) in DMF (40 mL) at rt was added sodium hydride (60% dispersion in mineral oil, 579 mg, 14.48 mmol). The reaction mixture was stirred for 1 h, then 1,2-dibromoethane (6.80 g, 136.18 mmol) was added. The resulting solution was heated at 50° C. for 24 h, then cooled to rt. The solution was treated with 2N HCl and extracted with EtOAc. The combined extracts were dried over MgSO4, filtered, and concentrated under reduced pressure. The crude material was purified by silica gel chromatography using a step gradient of 30 and 50% EtOAc/hexanes to give the title compound as a white solid (460 mg, 24%). GC/MS (EI) m/z 244 (M)+, RT 7.40 min.

Example 20

Preparation of 1-(2-bromo-ethoxy)-4-ethyl-2-methoxy-benzene

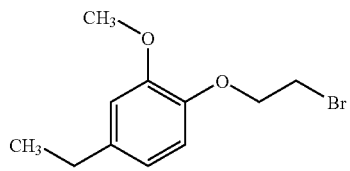

Using 4-ethyl-2-methoxyphenol as starting material, the title compound was prepared as described in Example 19 to give a white solid (371 mg, 20%). GC/MS (EI) m/z 258 (M)+, RT 7.72 min.

Example 21

Preparation of 1-(2-bromo-ethoxy)-2-chloro-4-methoxy-benzene

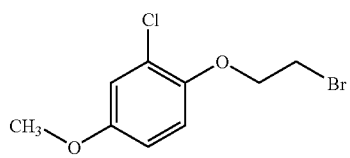

Using 2-chloro-4-methoxyphenol as starting material, the title compound was prepared as described in Example 19 to give a white solid (744 mg, 84%). GC/MS (EI) m/z 264 (M)+, RT 7.94 min.

Example 22

Preparation of 1-(3-bromo-propoxy)-2-methoxy-4-methyl-benzene

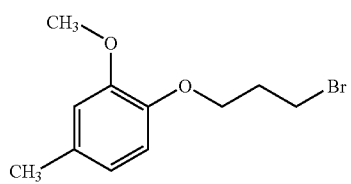

To a solution of 2-methoxy-4-methylphenol (500 mg, 3.62 mmol) in acetonitrile (20 mL) was added 1,3-dibromopropane (3.65 g, 201.89 mmol) followed by cesium carbonate (2.35 g, 7.24 mmol). The resulting solution was heated at 85° C. for 48 h, then cooled to rt. The solution was filtered through a Celite® pad. The Celite® was washed with acetone, and the combined filtrates were concentrated under reduced pressure to give the title compound as a white solid (395 mg, 42%). GC/MS (EI) m/z 258 (M)+, RT 7.94 min.

Steps 2 and 3: Coupling and Hydrolysis

Example 23

Preparation of (R) and (S)-2-{5-[2-(1,6-dibromo-naphthalen-2-yloxy)-ethoxy]-indol-1-yl}-propionic acid

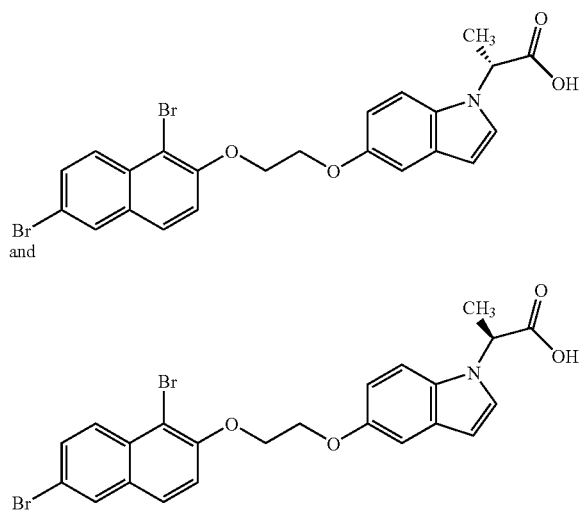

To a solution of 1,6-dibromo-2-(2-bromo-ethoxy)naphthalene (0.4 g, 0.98 mmol) (Example 15) in dry DMF (6 mL) was added 2-(5-hydroxy-indol-1-yl)-propionic acid methyl ester (0.215 g, 0.98 mmol) (Example 7) followed by cesium carbonate (1.59 g, 4.9 mmol). The reaction mixture was heated to 140° C. for 10 minutes and subsequently at 50° C. for 16 h. A saturated aqueous NaHCO$_3$ solution was added and the reaction mixture was extracted with ethyl acetate. The combined organic layers were dried over MgSO$_4$, filtered, and concentrated. The crude material was purified on reverse phase HPLC with gradient of 40% to 100% of acetonitrile and water mixture. The racemic mixture of the title compounds (122 mg, 46.3%) was collected as a white solid. $^1$H NMR (400 MHz, DMSO-d$_6$) δ 7.23-7.22(1H, m), 8.00-7.97 (2H, m), 7.71 (1H, dd), 7.63 (1H, d), 7.38 (1H, d), 7.29 (1H, d), 7.12 (1H, d), 6.79 (1H, dd), 6.36 (1H, d), 5.24 (1H, q), 4.58-4.55 (2H, m), 4.37-4.34 (2H, m), 1.68 (3H, d). LC/MS m/z 530 (M−H)$^-$, RT 3.60 min The racemic mixture (115 mg, 0.215 mmol) was separated into its two enantiomers, designated, 23A and 23B, on a Chiral Pak AD 20×250 column eluting with an isocratic solvent system of 35% isopropanol (containing 0.1% TFA) in hexanes (containing 0.1% TFA) at a flow rate of 20 mL/minute. The first peak off the column (RT=9.1 min) was designated Example 23A: (42 mg). $^1$H NMR (400 MHz, acetone-d$_6$) δ 8.13-8.09 (m, 2H), 7.95 (d, 1H), 7.70 (d, 1H), 7.62 (d, 1H), 7.38-7.33 (m, 2H), 7.19 (s, 1H), 6.89-6.87 (m, 1H), 6.42 (s, 1H), 5.29 (q, 1H), 4.64-4:62 (m, 2H), 4.47-4.45 (m, 2H), 1.80 (d, 3H). LC/MS m/z 531.9 (M+H)$^+$, RT 3.85 min. The second peak off the column (RT=13.0 min) was designated Example 23B: 40 mg. $^1$H NMR (400 MHz, acetone-d$_6$) δ 8.15-8.11 (m, 2H), 7.97 (d, 1H), 7.71 (d, 1H), 7.64 (d, 1H), 7.38-7.33 (m, 2H), 7.19 (s, 1H), 6.89-6.87 (m, 1H), 6.42 (s, 1H), 5.30 (q, 1H), 4.66-4.64 (m, 2H), 4.48-4.46 (m, 2H), 1.81 (d, 3H). LC/MS m/z 531.9 (M+H)$^+$, RT 3.85 min.

Example 24

Preparation of 2-{5-[2-(4-ethyl-2-methoxy-phenoxy)-ethoxy]-indol-1-yl}-propionic acid

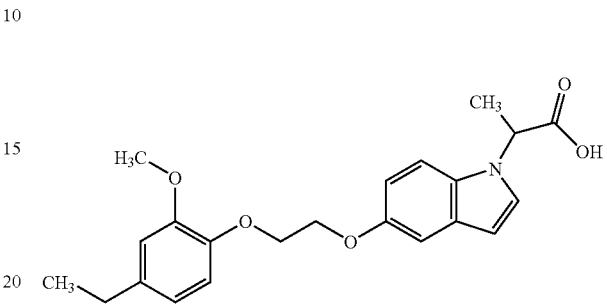

To a solution of the compound from Example 20 (0.2 g, 0.77 mmol) in dry DMF (5 mL) was added 2-(5-hydroxy-indol-1-yl)-propionic acid methyl ester (Example 7, 0.169 g, 0.77 mmol) followed by cesium carbonate (0.5 g, 1.54 mmol). The reaction mixture was heated to 140° C. for 3 h. HCl (2N) was added to the reaction mixture to adjust the pH to 2. The reaction mixture was extracted with ethyl acetate. The combined organic layers were dried over MgSO$_4$, filtered, and concentrated. The crude material was purified on reverse phase HPLC with gradient of 40% to 100% of acetonitrile and water mixture. The title compound (25 mg, 8%) was collected as a brownish solid. $^1$H NMR (400 MHz, acetone-d$_6$) δ 7.53 (s, 1H), 7.42 (d, 1H), 7.01 (d, 1H), 6.97-6.93 (m, 2H), 6.84 (d, 2H), 6.71 (dd, 1H), 5.37 (q, 1H), 4.42-4.29 (m, 4H), 3.81 (s, 3H), 2.58 (q, 2H), 1.85 (d, 3H), 1.20 (t, 3H). LC/MS m/z 384.3 (M+H)$^+$, RT 3.27 min.

Example 25

Preparation of 2-{5-[2-(2-methoxy-4-methyl-phenoxy)-ethoxy]-indol-1-yl}-propionic acid

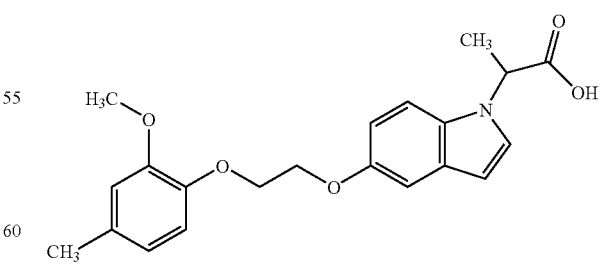

Using the compound from Example 19 as starting material the title compound was prepared as described in Example 24 to give a brownish solid (45 mg, 14%). $^1$H NMR (400 MHz, acetone-d$_8$) δ 7.32-7.27 (m, 2H), 7.10 (d, 1H), 6.86-6.80 (m, 2H), 6.75 (s, 1H), 6.62 (d, 1H), 6.36 (d, 1H), 5.23 (q, 1H), 4.29-4.25 (m, 4H), 3.74 (s, 3H), 2.22 (s, 3H), 1.75 (d, 3H). LC/MS m/z 370.3 (M+H)+, RT 3.11 min.

Example 26

Preparation of 2-{5-[2-(2-chloro-4-methyl-phenoxy)-ethoxy]-indol-1-yl}-propionic acid

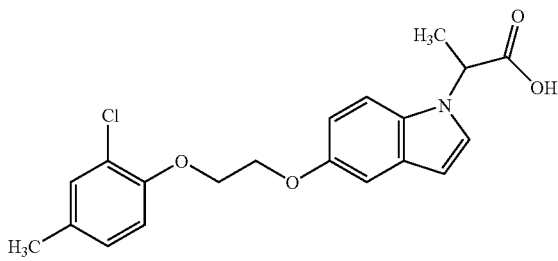

Using the compound from Example 16 as starting material the title compound was prepared as described in Example 24 to give a brownish solid (45 mg, 14%). ¹H NMR (400 MHz, acetone-$d_6$) δ7.32-7.27 (m, 2H), 7.17 (s, 1H), 7.13 (d, 1H), 7.10 (d, 2H), 6.81 (dd, 1H), 6.37 (d, 1H), 5.23 (q, 1H), 4.29-4.25 (m, 4H), 2.22 (s, 3H), 1.75 (d, 3H). LC/MS m/z 374.1 (M+H)+, RT 3.37 min.

Example 27

Preparation of 2-{5-[2-(4-bromo-2-chloro-phenoxy)-ethoxy]-indol-1-yl}-propionic acid

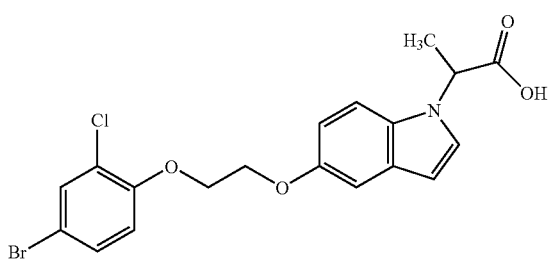

Using the compound from Example 17 as starting material, the title compound was prepared as described in Example 24 to give a brownish solid (45 mg, 14%). ¹H NMR (400 MHz, acetone-$d_6$) δ 7.51 (d, 1H), 7.40 (dd, 1H), 7.32-7.27 (m, 2H), 7.15-7.10 (m, 2H), 6.80 (dd, 1H), 6.35 (d, 1H), 5.24 (q, 1H), 4.43-4.34 (m, 4H), 1.75 (d, 3H). LC/MS m/z 439.9 (M+H)+, RT 3.54 min.

Example 28

Preparation of 2-{5-[2-(2-chloro-4-methoxy-phenoxy)-ethoxy]-indol-1-yl}-propionic acid

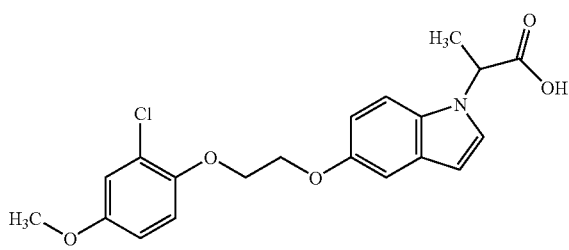

Using the compound from Example 21 as starting material, the title compound was prepared as described in Example 24 to give a brownish solid (32 mg, 10%). ¹H NMR (400 MHz, acetone-$d_6$) δ 7.38 (d, 1H), 7.34 (d, 1H), 7.17-7.14 (m, 2H), 6.99 (d, 1H), 6.88 (dt, 2H), 6.42 (d, 1H), 5.30 (q, 1H), 4.40-4.37 (m, 4H), 3.78 (s, 3H), 1.81 (d, 3H). LC/MS m/z 390.1 (M+H)+, RT 3.18 min.

Example 29

Preparation of 2-{5-[2-(2-cyano-4-methoxy-phenoxy)-ethoxy]-indol-1-yl}-propionic acid

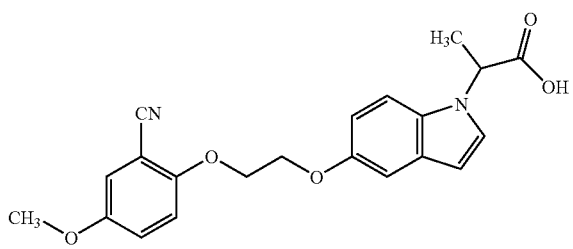

Using the compound from Example 18 as starting material, the title compound was prepared as described in Example 24 to give a brownish oil (20 mg, 6%). ¹H NMR (400 MHz, acetone-$d_6$): δ 7.37 (d, 1H), 7.34 (d, 1H), 7.29-7.17 (m, 4H), 6.86 (dd, 1H), 6.42 (d, 1H), 5.30 (q, 1H), 4.50-4.48 (m, 2H), 4.41-4.39 (m, 2H), 3.83 (s, 3H), 1.81 (d, 3H). LC/MS m/z 381.1 (M+H)+, RT 2.93 min.

Example 30

Preparation of 2-{5-[3-(2-methoxy-4-methyl-phenoxy)-propoxy]-indol-1-yl}-propionic acid

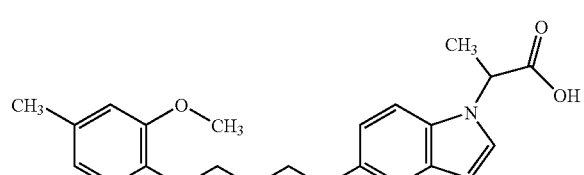

Using the compound from Example 19 as starting material the title compound was prepared as described in Example 24 to give a brownish solid (36 mg, 12%). ¹H NMR (400 MHz, acetone-$d_6$): δ 7.35 (d, 1H), 7.31 (d, 1H), 7.11 (d, 1H), 6.85 (d, 1H), 6.82 (dd, 1H), 6.77 (s, 1H), 6.67-6.65 (m, 1H), 6.40 (d, 1H), 5.27 (q, 1H), 4.21 (t, 2H), 4.16 (t, 2H), 3.78 (s, 3H), 2.26 (s, 3H), 2.23 (t, 2H), 1.80 (d, 3H). LC/MS m/z 384.1(M+H)+, RT 3.22 min.

Method 4: Preparation of Thiazolylphenols

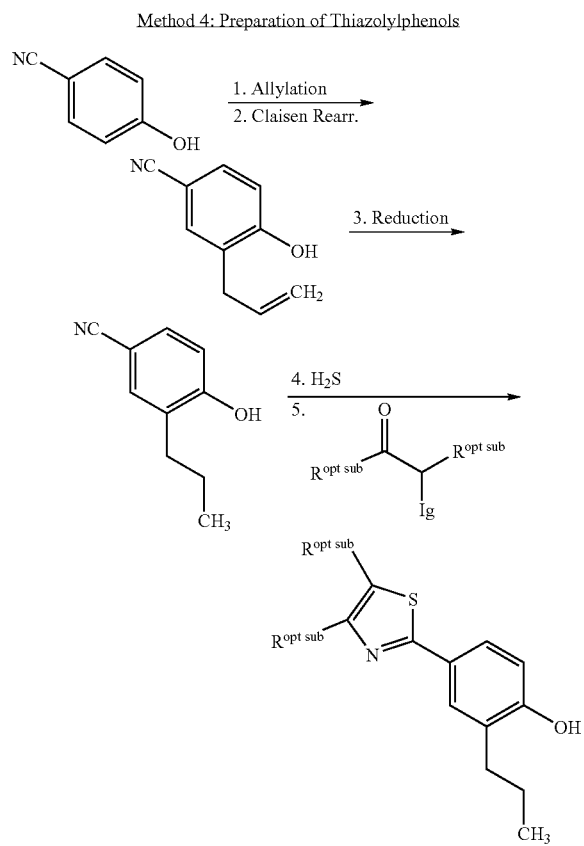

When R[6] = H and MeO: Nitriles are commercially available

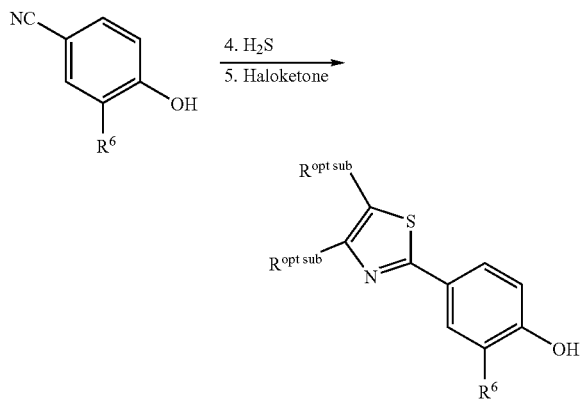

Step 1: Alkylation

Example 31

Preparation of 4-(allyloxy)benzonitrile

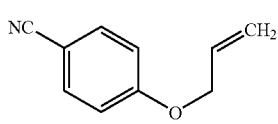

4-Hydroxybenzonitrile (30.0 g, 251.8 mmol), allyl bromide (39.6 g, 327.4 mmol), and cesium carbonate (98.5 g, 302.2 mmol) were dissolved in DMF (900 mL), and 1 mL water was added. After stirring for 12 h at ambient temperature, most of the DMF was removed in vacuo. Water was added and the reaction mixture was extracted with ethyl acetate. The combined organic layers were washed with $H_2O$ and brine. The organic layer was dried over $Na_2SO_4$, filtered, and the solvent was removed in vacuo. The title compound was obtained as a white crystalline material (40 g, 100%). $^1$H NMR (400 MHz, CDCl$_3$) δ 4.60 (d, 2H), 5.34 (d, 1H), 5.43 (d, 1H), 6.03 (m, 1H), 6.96 (d, 2H), 7.58 (d, 2H).

Step 2: Claisen Rearrangement

Example 32

Preparation of 3-allyl-4-hydroxybenzonitrile

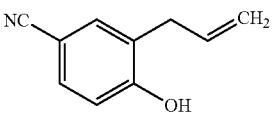

4-(Allyloxy)benzonitrile (40.0 g, 251.3 mmol) (Example 31) was heated under argon at 200° C. for 20 h. After cooling to rt, the product was purified via silica gel flash chromatography (ethyl acetate/hexane (v/v)=1:10 to 1:4) to give the title compound (27.5 g, 69%) as a white crystalline solid. $^1$H NMR (400 MHz, CDCl$_3$) δ 3.44 (d, 2H), 5.18 (d, 1H), 5.24 (d, 1H), 5.99 (m, 1H), 6.05 (br, 1H), 6.89 (d, 1H), 7.46 (d, 2H).

Step 3: Reduction

Example 33

Preparation of 4-hydroxy-3-propylbenzonitrile

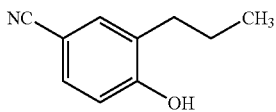

3-Allyl-4-hydroxybenzonitrile (20.0 g, 126 mmol) (Example 32) was dissolved in EtOH (320 mL) under argon. Pd/C (80 mg, 10%, Fluka) was added and the reaction mixture was stirred under a hydrogen atmosphere (1 atm) at rt for 20 h. The catalyst was filtered off, and then the reaction mixture was concentrated under reduced pressure, yielding 20.2 g (99%) of the title compound as a slightly greenish oil. $^1$H NMR (400 MHz, CDCl$_3$): δ0.95 (t, 3H), 1.63 (m, 2H), 2.56 (m, 2H), 6.86 (d, 1H), 7.30 (m, 2H).

Step 4: Thioamide Formation

Example 34

Preparation of 4-hydroxy-3-propylbenzenecarbothioamide

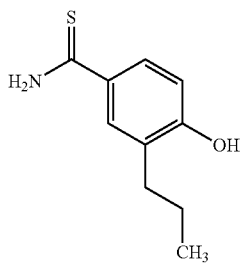

A solution of 4-hydroxy-3-propylbenzonitrile (35.63 g, 0.221 mol) (Example 33) in DMF (300 mL) was saturated with hydrogen sulfide at rt (moderate flow over 45 minutes). Temperature was monitored (increase of about 7° C.). To the solution was added diethylamine (45.73 mL, 0.442 mol). The temperature increased by 10° C., and the green reaction mixture became darker green. Hydrogen sulfide was passed into the dark green solution for another 30 minutes (at this point the reaction temperature was 40° C.). The reaction mixture was warmed to 60° C. Hydrogen sulfide was again passed into the solution at 60° C. over 2 h. The reaction mixture was cooled and stirred at rt for 54 h and most of the solvent removed under reduced pressure. The resultant residue was partitioned between ethyl acetate (300 mL) and water (200 mL). The organic layer was washed with water (4×100 mL), then brine, and dried over sodium sulfate, filtered, and concentrated. The resultant orange oil was triturated in hexanes (300 mL) and ether (25 mL) to give a yellow solid (39.97 g, 93%) after drying for 1 h under suction. LC/MS m/z 196.1 $(M+H)^+$, RT 2.16 min. $^1$H NMR (400 MHz, DMSO-$d_6$) δ 9.94 (s, 1H), 9.44 (s, 1H), 9.14 (s, 1H), 7.73-7.65 (m, 2H), 6.73 (d, 1H), 2.51-2.47 (m, 2H), 1.59-1.50 (m, 2H), 0.90 (t, 3H).

Example 35

Preparation of 4-hydroxy-3-methoxybenzenecarbothioamide

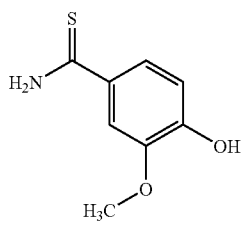

A solution of 4-hydroxy-3-methoxybenzonitrile (15.0 g, 0.1 mol) in DMF (150 mL) was treated with a slow flow of gaseous hydrogen sulfide for 30 minutes at rt. Diethyl amine (15.6 mL, 11.0 g, 0.15 mol) was added and the solution was heated at 70° C. for 4 h. The solution was cooled to rt and the residual $H_2S$ was removed by passing argon through the solution for 30 minutes. The solvent was evaporated under reduced pressure and the residue was filtered through a plug of silica, followed by washing with EtOAc. Removal of the solvent resulted in a crude brown oil, which was used in the next step without further purification.

Step 5: Thiazole Formation

Example 36

Preparation of 2-propyl-4-(4,5,6,7-tetrahydro-benzothiazol-2-yl)-phenol

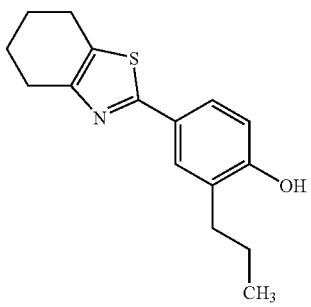

A suspension of 4-hydroxy-3-propyl-thiobenzamide (5 g, 0.026 mol) (Example 34), 2-chlorocyclohexanone (4.07 g, 0.031 mol), and p-toluenesulfonic acid monohydrate (0.244 g, 1.28 mmol) in anhydrous toluene (100 mL) was heated to reflux in a Dean-Stark apparatus under argon for 12 h. At about 90° C., the mixture became a red orange oil and after 4 h of refluxing, precipitation was observed. The reaction mixture was cooled and diluted with ethyl acetate (50 mL). The organic layer was washed successively with saturated sodium bicarbonate (2×50 mL), water (2×50 mL), brine, dried over sodium sulfate, and concentrated to give the desired product as a tan solid (6.89 g, 98%). LC/MS m/z 274.3 $(M+H)^+$, RT 2.99 min. $^1$H NMR (400 MHz, DMSO-$d_6$) δ 9.75 (s, 1H), 7.53-7.44 (m, 2H), 6.81 (d, 1H), 2.72-2.68 (m, 4H), 2.54-2.49 (m, 2H), 1.78 (b, 4H), 1.58-1.53 (m, 2H), 0.90 (t, 3H).

Example 37

Preparation of 4-(4-isopropoxy-1,3-thiazol-2-yl)-2-methoxyphenol

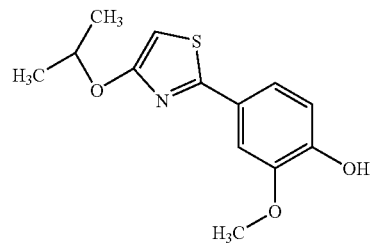

4-Hydroxy-3-methoxybenzenecarbothioamide (3.0 g, 16.37 mmol) (Example 35) and 2-chloro-N,N-dimethylacetamide were dissolved in isopropanol, and the mixture was heated at reflux for 12 h. The solvent was removed under reduced pressure. The residue was washed with water and extracted with ethyl acetate. The combined organic layers were dried over $Na_2SO_4$, filtered, and the solvent was removed in vacuo. Purification via silica gel flash chromatography (ethyl acetate/hexane (v/v)=1:4) yielded a solid (1.99 g, 46%). $^1$H NMR (400 MHz, CDCl$_3$) δ 1.42 (d, 6H), 3.91 (s, 3H), 4.64 (septet, 1H), 5.95 (s, 1H), 6.0 (br, 1H), 6.91 (d, 1H), 7.36 (d, 1H), 7.53 (s, 1H).

Method 5: Preparation of Oxazolylphenols

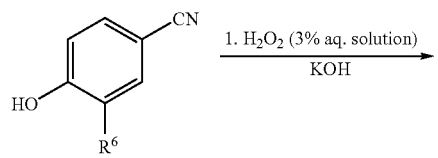

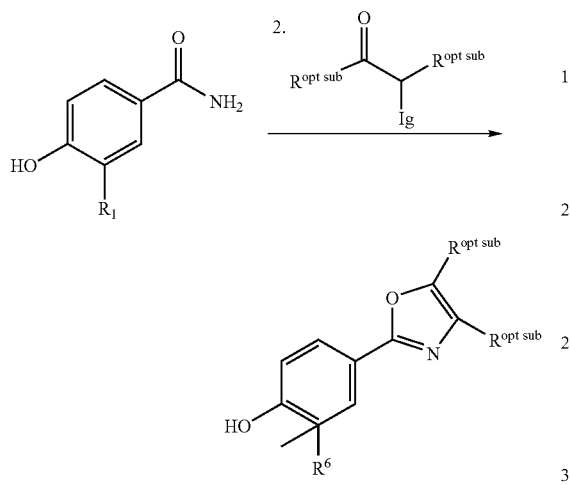

R[6] = H, MeO, or n-Pr

When R[6]=n-propyl, the cyanophenol was prepared based on examples described in Method 4.

Step 1: Hydrolysis of Nitrile

Example 38

Preparation of 4-hydroxy-3-methoxy-benzamide

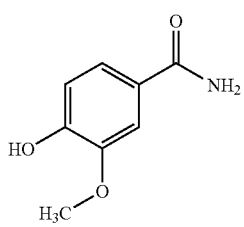

A 3% aqueous solution of hydrogen peroxide (155 mL, 0.151 mol) was added to a flask containing 4-hydroxy-3-methoxybenzonitrile (5.00 g, 33.52 mmol) at rt. Solid KOH (9.78 g, 174.33 mmol) was added slowly. Gas was evolved and the temperature of the rose. The solution was stirred for 16 h, and excess sodium sulfite was added. The mixture was then filtered and the solution was acidified to pH 2 with 2N HCl. The aqueous solution was extracted with dichloromethane. The combined organic layers were dried over $MgSO_4$, filtered, and concentrated to give the product as a pale yellow solid (4.27 g, 76.2%). $^1$H NMR (400 MHz, DMSO-$d_6$) δ 9.52 (s, 1H), 7.75 (s, 1H), 7.42 (d, 1H), 7.34 (dd, 1H), 7.096 (s, 1H), 6.76 (d, 1H), 3.78 (s, 3H).

Step 2: Oxazole Formation

Example 39

Preparation of 4-(4-ethyl-1,3-oxazol-2-yl)-2-methoxyphenol

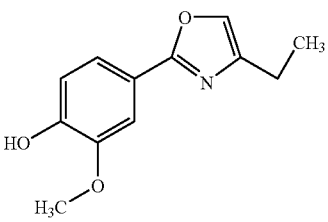

To a solution of 4-hydroxy-3-methoxybenzamide (460 mg, 2.75 mmol) (Example 38) in toluene (3 mL)/1,4-dioxane (3 mL), was added 1-bromo-2-butanone (623.29 mg, 4.13 mmol). The solution was heated to reflux for 18 h. The reaction mixture was cooled to rt, and the solvent was removed under reduced pressure. The crude residue was purified on silica gel to give the title compound as a yellow oil (434 mg, 72%). $^1$H NMR (400 MHz, DMSO-$d_6$) δ 9.60 (s, 1H), 7.78 (s, 1H), 7.39 (d, 1H), 7.36 (dd, 1H), 6.83 (d, 1H), 3.79 (s, 3H), 2.45 (m, 2H), 1.18 (t, 3H).

Method 6a: Preparation of Oxazolylphenols

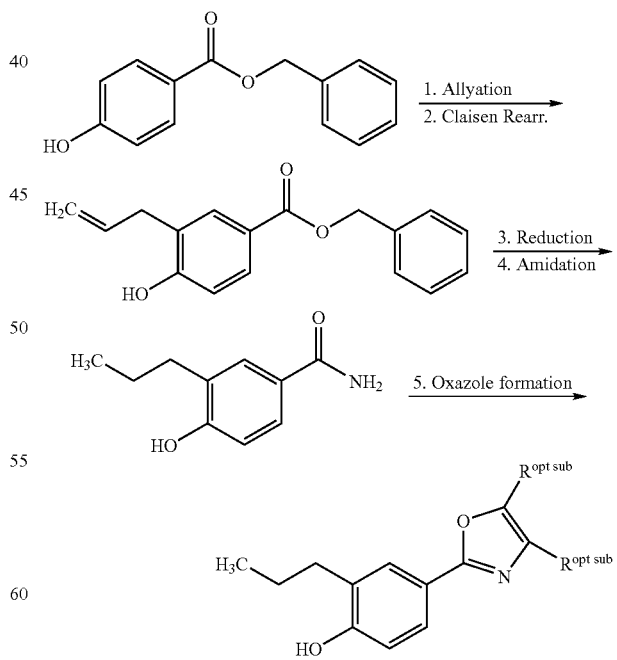

Steps 4 and 5 were also used during the synthesis of targets where the n-propyl group was replaced with H and MeO groups.

Method 6b: Preparation of Oxazolylphenols

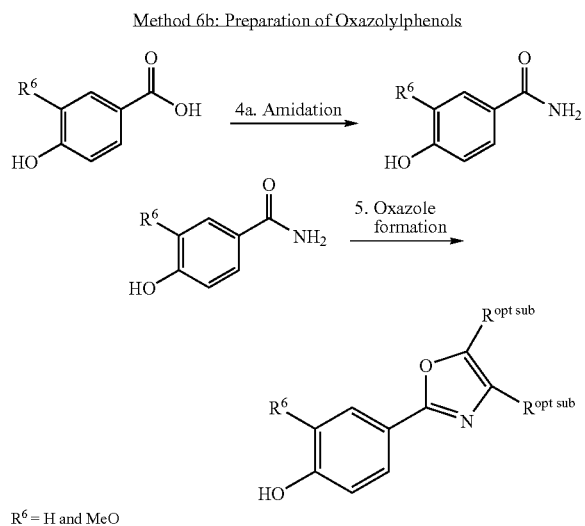

R⁶ = H and MeO

Step 1: Allylation

Example 40

Preparation of benzyl 4-(allyloxy)benzoate

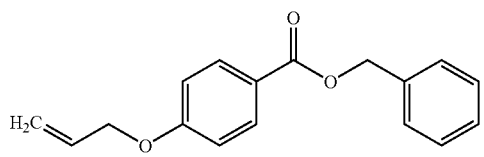

To a solution of benzyl 4-hydroxybenzoate (15.00 g, 65.1 mmol) in 130 mL acetone cooled in an ice water bath was added allyl bromide (11.4 mL, 130.1 mmol), followed by portionwise addition of potassium carbonate (45.00 g, 325.3 mmol). The ice bath was removed and the reaction mixture was warmed to rt. The mixture was stirred for 19 h. The precipitates were removed by filtration and the filtrate was concentrated to yield a colorless oil (17.65 g, 100%). LC/MS m/z 269 (M+H)⁺; ¹H NMR (400 MHz, CDCl₃) δ 8.00-8.04 (m, 2H), 7.31-7.45 (m, 5H), 6.91-6.94 (m, 2H), 6.00-6.91 (m, 1H), 5.30-5.45 (m, 4H), 4.58-4.61 (m, 2H).

Step 2: Claisen Rearrangement

Example 41

Preparation of benzyl 3-allyl-4-hydroxybenzoate

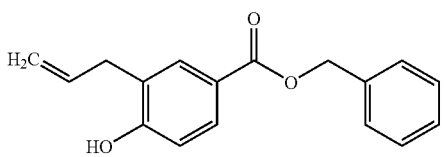

Benzyl 4-(allyloxy)benzoate (15.50 g, 57.8 mmol) (Example 40) was heated at 200° C. under argon for 18 h with stirring. Benzyl 3-allyl-4-hydroxybenzoate was obtained as a solid (15.40 g, 99%). LC/MS m/z 269 (M+H)⁺; ¹H NMR (400 MHz, CDCl₃) δ 7.86-7.89 (m, 2H), 7.33-7.45 (m, 5H), 6.83 (d, 1H), 5.96-6.06 (m, 1H), 5.48 (s, 1H), 5.33 (s, 2H), 5.15-5.20 (m, 2H), 3.45 (d, 2H).

Step 3: Reduction

Example 42

Preparation of 4-hydroxy-3-propylbenzoic acid

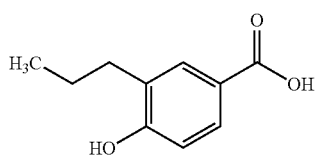

A mixture of benzyl 3-allyl-4-hydroxybenzoate (15.40 g, 57.4 mmol) (Example 41), 10% Pd/C (1.54 g), and 60 mL ethanol was placed in a Parr hydrogenator under 60 psi of H₂. The mixture was shaken for 2 h. The catalyst was removed by filtering through a plug of Celite®. The filtrate was concentrated to yield a thick oil (10.5 g 100%). ¹H NMR (400 MHz, DMSO-d₆) δ 12.36 (br s, 1H), 10.08 (s, 1H), 7.59-7.63 (m, 2H), 6.81 (d, 1H), 2.49-2.53 (m, 2H), 1.50-1.59 (m, 2H), 0.89 (t, 3H).

Step 4: Amidation

Example 43

Preparation of 4-hydroxy-3-propyl-benzamide

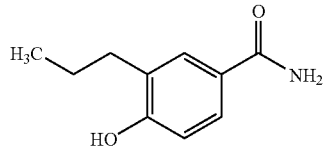

A solution of 4-hydroxy-3-propylbenzoic acid (7.30 g, 40.5 mmol) (Example 42) in thionyl chloride (15 mL, 205.6 mmol) was heated at reflux for 2 h and concentrated under reduced pressure. The residue was dissolved in THF. This solution was added to aqueous 30% NH₄OH solution (30 mL) at 0° C. The reaction mixture was stirred for 20 h at rt. The crude material was purified on HPLC to yield a solid (0.82 g, 11%). LC/MS m/z 180 (M+H)⁺; ¹H NMR (400 MHz, DMSO-d₆) δ 9.77 (s, 1H), 7.66 (br s, 1H), 7.51-7.59 (m, 2H), 7.01 (br, s, 1H), 6.75 (d, 1H), 2.47-2.51 (m, 2H), 1.51-1.60 (m, 2H), 0.90 (t, 3H).

Step 5: Oxazole Formation

Example 44

Preparation of 4-(4-ethyl-1,3-oxazol-2-yl)-2-propyl-phenol

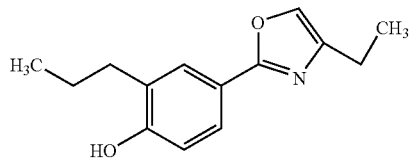

A mixture of 4-hydroxy-3-propylbenzamide (200.0 mg, 1.1 mmol) (Example 43), 1-bromo-2-butanone (0.19 mL, 1.7 mmol), toluene (1.5 mL), and 1,4-dioxane (1.5 mL) was heated at reflux for 8 h with a Dean-Stark trap. The solvents were evaporated. The crude product was purified on HPLC to yield a solid (124.2 mg, 48%). LC/MS m/z 232 (M+H)$^+$; $^1$H NMR (400 MHz, DMSO-d$_6$) δ 9.87 (s, 1H), 7.56-7.76 (m, 3H), 6.85 (d, J=8.4 Hz, 1H), 2.46-2.56 (m, 4H), 1.52-1.61 (m, 2H), 1.18 (t, J=7.6 Hz, 3H), 0.91 (t, J=7.3 Hz, 3H).

Method 7: Preparation of Benzisoxazole

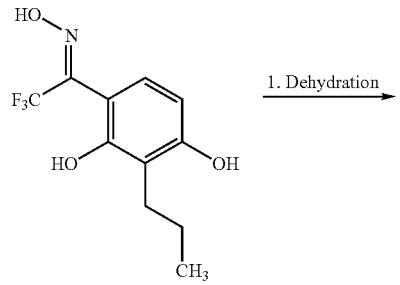

Step 1: Dehydration

Example 45

Preparation of 7-propyl-3-(trifluoromethyl)-1,2-benzisoxazol-6-ol

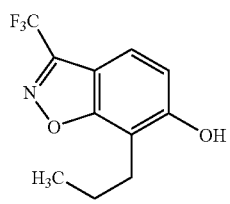

1-(2,4-Dihydroxy-3-propylphenyl)-2,2,2-trifluoroethanone oxime (prepared by the method described in WO 97/28137, 4.2 g, 15.96 mmol) and triphenylphosphine (8.82 g, 33.6 mmol) were dissolved in THF (250 mL) and the mixture was cooled to 0° C. A solution of diethyl azodicarboxylate (5.02 mL, 32.0 mmol) in THF (150 mL) was then slowly added over a period of 30 minutes. The reaction mixture was stirred for 1 h at 0° C. After addition of water (500 mL), the aqueous layer was extracted with ethyl acetate. The combined organic layers were washed with brine and dried over sodium sulfate. The solvent was removed in vacuo and the product purified via silica gel flash chromatography (ethyl acetate/hexane (v/v)=1:6). The product was obtained as a white-yellow powder in a yield of 1.96 g (8.0 mmol, 50%). $^1$H NMR (300 MHz, CDCl$_3$) δ 1.00 (t, 3H), 1.73 (m, 2H), 2.88 (t, 2H), 5.34 (s, 1H), 6.93 (d, 1H), 7.48 (d, 1H).

Step 2: Alkylation

Example 46

Preparation of 6-(3-bromo-propoxy)-7-propyl-3-trifluoromethyl-1,2-benzo[d]-isoxazole

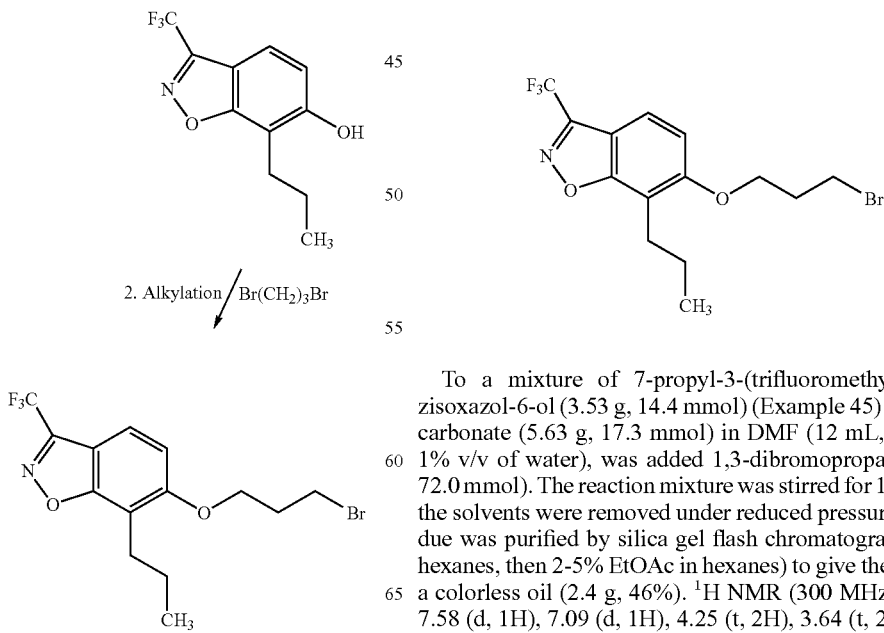

To a mixture of 7-propyl-3-(trifluoromethyl)-1,2-benzisoxazol-6-ol (3.53 g, 14.4 mmol) (Example 45) and cesium carbonate (5.63 g, 17.3 mmol) in DMF (12 mL, containing 1% v/v of water), was added 1,3-dibromopropane (14.5 g, 72.0 mmol). The reaction mixture was stirred for 12 h at rt and the solvents were removed under reduced pressure. The residue was purified by silica gel flash chromatography (100% hexanes, then 2-5% EtOAc in hexanes) to give the product as a colorless oil (2.4 g, 46%). $^1$H NMR (300 MHz, CDCl$_3$) δ 7.58 (d, 1H), 7.09 (d, 1H), 4.25 (t, 2H), 3.64 (t, 2H), 2.92 (t, 2H), 2.40 (m, 2H), 1.72 (m, 2H), 0.99 (t, 3H).

Method 8: Preparation of Phenolthiazole 1-Indoles

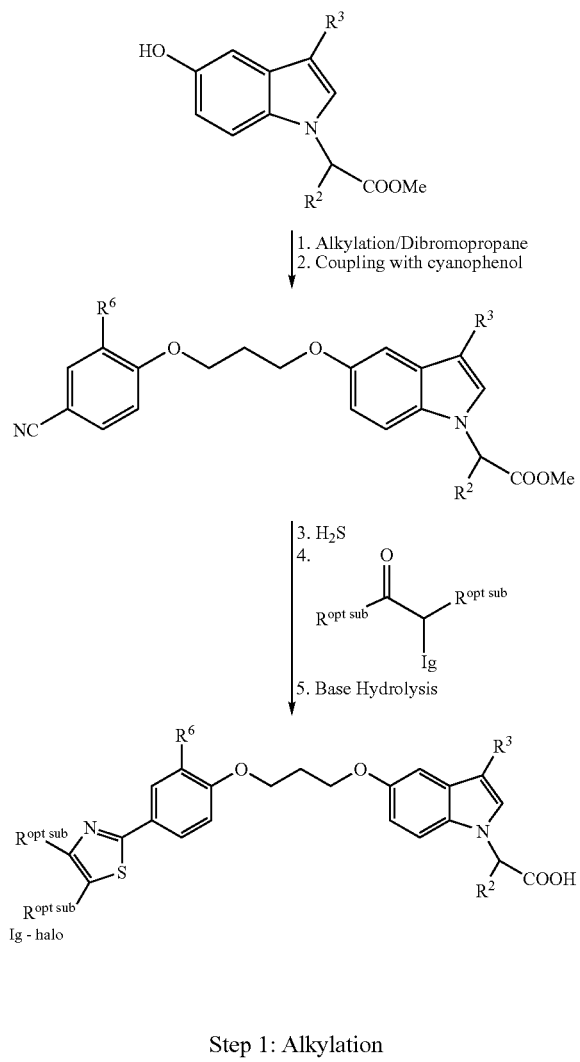

Step 1: Alkylation

Example 47

Preparation of methyl [5-(3-bromopropoxy)-1H-indol-1-yl]acetate

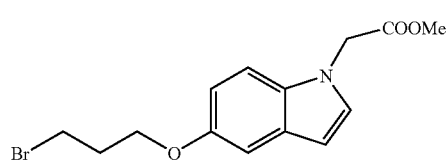

To a solution of methyl (5-hydroxy-1H-indol-1-yl)acetate (1.0 g, 4.87 mmol) (Example 9) in 35 mL DMF, was added 1,3-dibromopropane (5.90 g, 29.24 mmol) and Cs$_2$CO$_3$ (3.18 g, 9.75 mmol). The mixture was stirred at rt for 6 h, and then the solvent was evaporated under reduced pressure. The residue was suspended in EtOAc, filtered, and the filter cake was washed with EtOAc. The combined organic layers were dried, concentrated, and purified by column chromatography (0-10% EtOAc in hexane) to give 720 mg (45%) of the product containing minor impurities. This material was used in later steps with no further purification. $^1$H NMR (400 MHz, CDCl$_3$) δ 7.18-7.10 (m, 2H), 7.05 (d, 1H), 6.94-6.85 (m, 1H), 6.50 (d, 1H), 4.80 (s, 2H), 4.18 (t, 2H), 3.75 (s, 3H), 3.65 (t, 2H), 2.40-2.30 (m, 2H).

Example 48

Preparation of 2-[5-(3-bromo-propoxy)-indol-1-yl]-propionic acid methyl ester

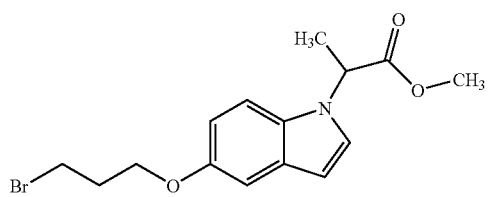

The title compound was prepared according to the method described in Example 47. $^1$H NMR (400 MHz, CD$_3$OD) δ 1.82 (d 3H), 2.34 (m 2H), 3.64 (t 2H), 3.70 (s 3H), 4.14 (t 2H), 5.1 (q 1H), 6.48 (d 1H), 6.85-6.90 (m 1H), 7.11 (d 1H), 7.18-7.25 (m 2H).

Example 49

Preparation of [5-(3-bromo-propoxy)-3-methyl-indo-1-yl]-acetic acid ethyl ester

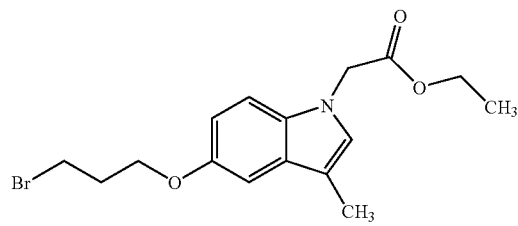

The title compound was prepared according to the method described in Example 47. $^1$H NMR (400 MHz, CDCl$_3$) δ 7.10 (m, 1H), 7.02 (d, 1H), 6.82-6.85 (m, 2H), 4.77 (s, 2H), 4.18 (m, 4H), 3.62 (t, 2H), 2.39 (m, 2H), 2.31 (s, 3H), 1.23 (t, 3H).

Example 50

Preparation of 2-[5-(3-bromo-propoxy)-3-methyl-indol-1-yl]-propionic acid methyl ester

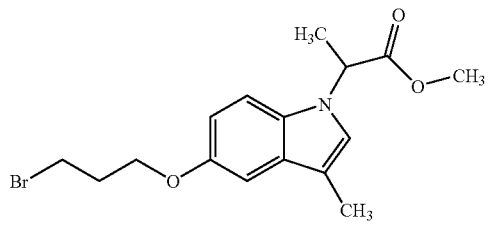

The title compound was prepared according to the method described in Example 47. ¹H NMR (400 MHz, CDCl₃) δ 7.18 (d, 1H), 7.01 (m, 2H), 6.82 (m, 1H), 5.02 (q, 1H), 4.19 (t, 2H), 3.70 (s, 3H), 3.63 (t, 2H), 2.39 (m, 2H), 2.30 (s, 3H), 1.79 (d, 3H).

Step 2: Coupling

Example 51

Preparation of methyl {5-[3-(4-cyano-2-propylphenoxy)propoxy]-1H-indol-1-yl}acetate

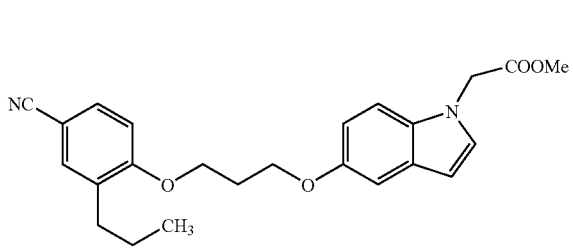

To a mixture of 4-hydroxy-3-propylbenzonitrile (Example 33, 1.33 g, 8.28 mmol) and methyl [5-(3-bromopropoxy)-1H-indol-1-yl]acetate (Example 47, 2.70 g, 8.28 mmol) in DMF (50 mL, containing 1% water), was added cesium carbonate (5.39 g, 16.55 mmol). The mixture was stirred at rt for 24 h and then the solvent was evaporated under reduced pressure. The residue was suspended in ethyl acetate and filtered. The filtrate was concentrated and purified via silica gel column chromatography (0-10% EtOAc in hexanes) to give 787 mg (23%) of the product as a solid. This was used in later steps with no further purification.

Step 3: Thioamide Formation

Example 52

Preparation of methyl (5-{3-[4-(aminocarbonothioyl)-2-propylphenoxy]-propoxy}-1H-indol-1-yl)acetate

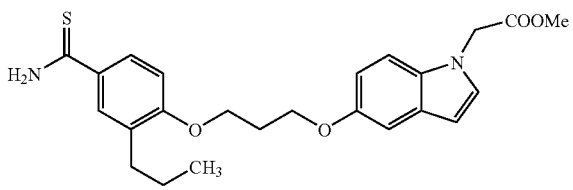

Hydrogen sulfide was passed through a solution of methyl {5-[3-(4-cyano-2-propylphenoxy)propoxy]-1H-indol-1-yl}acetate (Example 51, 787 mg, 1.94 mmol) in DMF (15 mL) for 30 minutes at rt. Diethyl amine (0.3 mL, 2.90 mmol) was added, and the solution was heated to 70° C. for 3 h. The reaction mixture was cooled to rt, and the residual H₂S was removed by passing argon through the reaction mixture for 30 minutes. The solvent was evaporated under reduced pressure and the residue was filtered through a plug of silica and washed with EtOAc. Concentration of solvent yielded a brown oil which was used in the next step without further purification. LC/MS m/z 441.2 (M+H)⁺; RT 3.35 min.

Step 4: Thiazole Formation

Example 53

Preparation of methyl (5-{3-[4-(4-ethyl-1,3-thiazol-2-yl)-2-propylphenoxy]propoxy}-1H-indol-1-yl)acetate

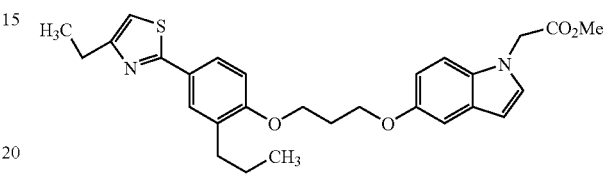

To a solution of methyl (5-{3-[4-(aminocarbonothioyl)-2-propyl-phenoxy]-propoxy}-1H-indol-1-yl)acetate (Example 52, 500 mg, 1.14 mmol) in ethanol (35 mL), was added 1-bromo-2-butanone (739 mg, 2.27 mmol) and pyridine (0.14 mL, 135 mg, 1.70 mmol). The reaction mixture was stirred for 3 h at 70° C. The solvent was evaporated under reduced pressure and the residue was purified by silica gel chromatography (0-15% EtOAc in hexane) to give 89 mg (16%) of the title compound. ¹H NMR (400 MHz, CDCl₃) δ 7.75-7.70 (m, 2H), 7.18-7.12 (m, 2H), 7.05 (d, 1H) 6.95-6.85 (m, 2H), 6.80 (s, 1H), 6.48 (d, 1H), 4.85 (s, 2H), 4.25-4.20 (m, 4H), 3.75 (s, 3H), 2.85 (q, 2H), 2.70-2.60 (m, 2H), 2.40-2.30 (m, 2H), 1.75-1.60 (m, 2H), 1.35 (t, 3H), 0.95 (t, 3H).

Step 5: Hydrolysis

Example 54

Preparation of (5-{3-[4-(4-ethyl-1,3-thiazol-2-yl)-2-propylphenoxy]propoxy}-1H-indol-1-yl)acetic acid

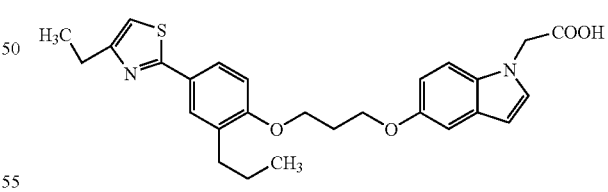

To a solution of methyl (5-{3-[4-(4-ethyl-1,3-thiazol-2-yl)-2-propylphenoxy]propoxy}-1H-indol-1-yl)acetate (Example 53, 89 mg, 0.18 mmol) in 3.0 mL THF, was added LiOH.H₂O (30 mg, 0.72 mmol) in water (1.0 mL). The mixture was stirred for 12 h at rt. The solvents were evaporated and the residue was suspended in a small volume of water. The pH of the mixture was adjusted to 3 with 1 N HCl. The aqueous layer was extracted with ethyl acetate. The combined organic layers were concentrated to give 65 mg (75%) of the product as a white solid. $^1$H NMR (400 MHz, CDCl$_3$) δ 7.42 (d, 1H), 7.35 (dd, 1H), 7.10-7.05 (m, 2H), 7.08 (d, 1H), 6.90 (dd, 1H), 6.78 (s, 1H), 6.45 (d, 1H), 6.35 (d, 1H), 4.85 (s, 2H), 4.34 (t, 2H), 4.26 (t, 2H), 2.92 (q, 2H), 2.55-2.45 (m, 2H), 2.25-2.15 (m, 2H), 1.62-1.50 (m, 2H), 1.35 (t, 3H), 0.92 (t, 3H).

Method 9: Preparation of Phenolthiazole 1-Indoles (Second Method)

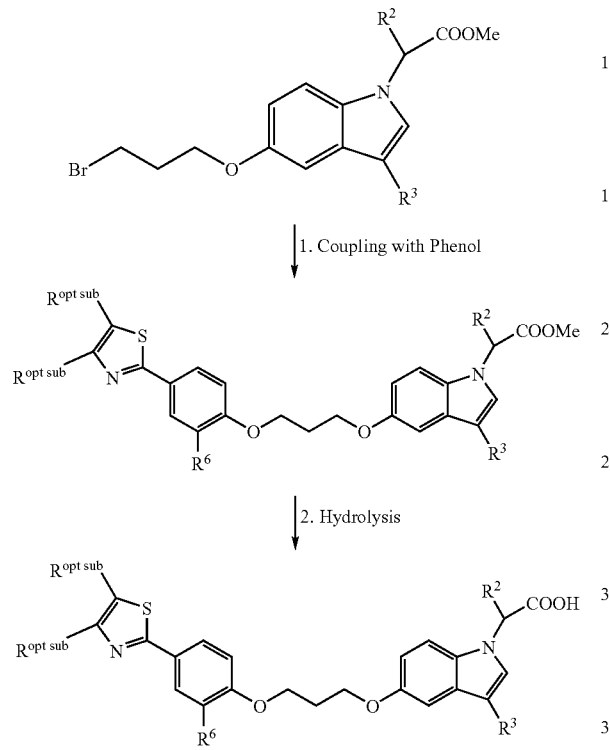

[5-(3-Bromo-propoxy)-indol-1-yl]-acetic acid methyl ester was prepared in similar fashion as described in Method 8.

Step 1: Coupling
Example 55
Preparation of methyl (5-{3-[2-propyl-4-(4,5,6,7-tetrahydro-1,3-benzothiazol-2-yl)phenoxy]propoxy}-1H-indol-1-yl)acetate

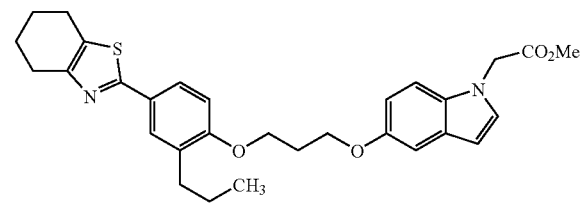

2-Propyl-4-(4,5,6,7-tetrahydro-benzothiazol-2-yl)-phenol (Example 36, 0.75 g, 2.76 mmol) was combined with [5-(3-bromo-propoxy)-indol-1-yl]-acetic acid methyl ester (Example 47, 0.75 g, 2.30 mmol) in 12 mL DMF (containing 1 v/v % of water). To this mixture was added Cs$_2$CO$_3$ (1.50 g, 4.60 mmol), and the resulting mixture was allowed to stir at rt for 14 h. At this time, the reaction mixture was diluted with EtOAc (50 mL) and then washed three times with water (75 mL total). The water layers were extracted with EtOAc (25 mL) and the combined organic extracts were dried over MgSO$_4$, filtered, and then concentrated under reduced pressure. Purification via flash silica gel chromatography (1:1 hexane/EtOAc) gave the title compound (800 mg, 64%) as a white solid. $^1$H NMR (400 MHz, CDCl$_3$) δ 7.75-7.70 (m, 2H), 7.18-7.10 (m, 2H), 7.05 (d, 1H), 6.92-6.85 (m, 2H), 6.48 (d, 1H), 4.84 (s, 2H), 4.30-4.20 (m, 4H), 3.75 (s, 3H), 2.90-2.75 (m, 4H) 2.70-2.60 (m, 2H), 2.40-2.30 (m, 2H), 1.95-1.85 (m, 4H), 1.70-1.58 (m, 2H), 0.95 (t, 3H).

Example 56

Preparation of methyl (5-{3-[4-(4-isopropoxy-1,3-thiazol-2-yl)-2-methoxyphenoxy]propoxy}-1H-indol-1-yl)acetate

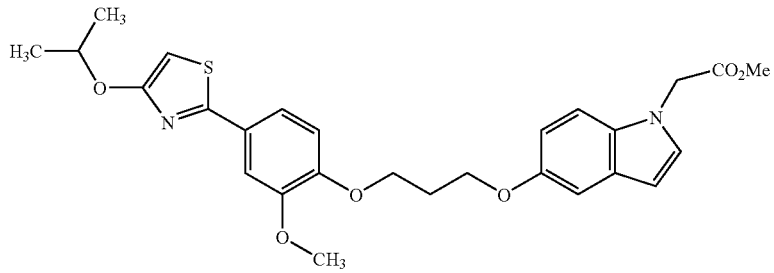

To a mixture of 4-(4-isopropoxy-1,3-thiazol-2-yl)-2-methoxy-phenol (Example 37, 269 mg, 1.01 mmol) and ethyl [5-(3-bromopropoxy)-1H-indol-1-yl]acetate (Example 47, 331 mg, 1.01 mmol) in 8 mL DMF (containing 1 v/v % of water), was added cesium carbonate (661 mg, 2.03 mmol). After stirring the reaction mixture for 16 h at rt, DMF was evaporated under reduced pressure. The residue was suspended in ethyl acetate and filtered through a silica gel plug to give 204 mg (39%) of a white solid, which was used in the next step with no further purification.

Step 2: Hydrolysis

Example 57

Preparation of (5-{3-[2-propyl-4-(4,5,6,7-tetrahydro-1,3-benzothiazol-2-yl)phenoxy]propoxy}-1H-indol-1-yl)acetic acid

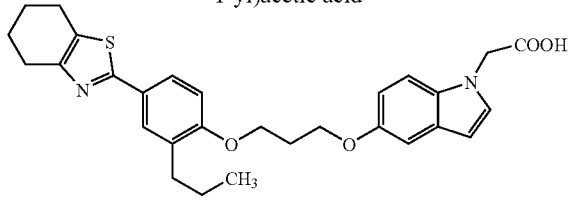

To a solution of methyl (5-{3-[2-propyl-4-(4,5,6,7-tetrahydro-1,3-benzothiazol-2-yl)phenoxy]propoxy}-1H-indol-1-yl)acetate (Example 55, 145 mg, 0.28 mmol) in THF (4.8 mL), was added LiOH.H$_2$O (39 mg, 0.84 mmol) in water (1.6 mL), and the mixture was stirred for 12 h at rt. The solvents were evaporated and a small volume of water was added to the residue. The pH of the mixture was adjusted to 3 with 1N HCl. The aqueous layer was extracted with ethyl acetate. The combined organic layers were dried, filtered, and concentrated to give 140 mg (99%) of the product as a white solid. $^1$H NMR (400 MHz, CDCl$_3$) δ 7.30 (d, 1H), 7.25-7.15 (m, 3H), 7.10 (d, 1H), 6.92 (dd, 1H), 6.45 (d, 1H), 6.20 (d, 1H), 4.85 (s, 2H), 4.40-4.32 (m, 2H), 4.32-4.22 (m, 2H), 2.90-2.80 (br, 2H), 2.80-2.70 (br, 2H), 2.50-2.40 (m, 2H), 2.25-2.05 (m, 2H), 1.95-1.75 (br, 4H), 1.60-1.40 (m, 2H), 0.90 (t, 3H). LC/MS m/z 505.2 (M+H)$^+$, RT 3.88 min.

Example 58

Preparation of (5-{3-[4-(4-isopropoxy-1,3-thiazol-2-yl)-2-methoxyphenoxy]propoxy}-1H-indol-1-yl) acetic acid

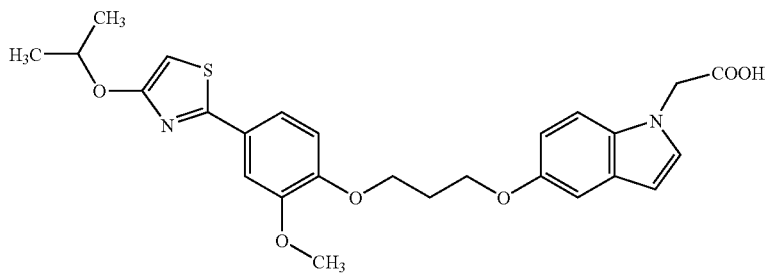

Methyl (5-{3-[4-(4-isopropoxy-1,3-thiazol-2-yl)-2-methoxyphenoxy]propoxy}-1H-indol-1-yl)acetate (Example 56, 204 mg, 0.40 mmol) was dissolved in THF (3 mL) in a round bottom flask, and LiOH.H$_2$O (67 mg, 1.60 mmol) in water (1 mL) was added. The mixture was stirred at rt for 16 h. The solvents were evaporated under reduced pressure and the residue was suspended in small volume of water. The pH of the mixture was adjusted to 3 with 1 N HCl. The aqueous layer was immediately extracted with EtOAc. The combined organic layers were dried, filtered, and concentrated to give 182 mg (91%) of the product as a white solid. $^1$H NMR (400 MHz, CDCl$_3$) δ: 7.42 (s, 1H), 7.32 (d, 1H), 7.15-7.08 (m, 2H), 7.04 (d, 1H), 6.88 (dd, 1H), 6.82 (d, 1H), 6.52 (d, 1H), 5.96 (s, 1H), 4.85 (s, 2H), 4.70-4.60 (q, 1H), 4.35-4.20 (m, 4H), 3.88 (s, 3H), 2.38-2.28 (m, 2H), 1.42 (d, 6H).

Example 59

Preparation of (S)-2-(5-{3-[4-(4-ethoxy-5-methyl-thiazol-2-yl)-2-propyl-phenoxy]-propoxy}-indol-1-yl)-propionic acid and (R)-2-(5-{3-[4-(4-ethoxy-5-methyl-thiazol-2-yl)-2-propyl-phenoxy]-propoxy}-indol-1-yl)-propionic acid

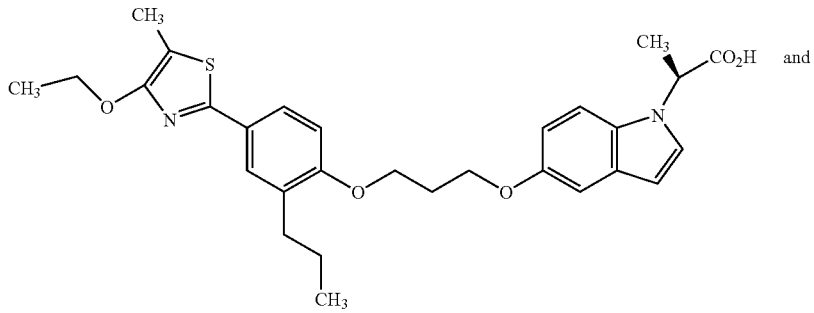

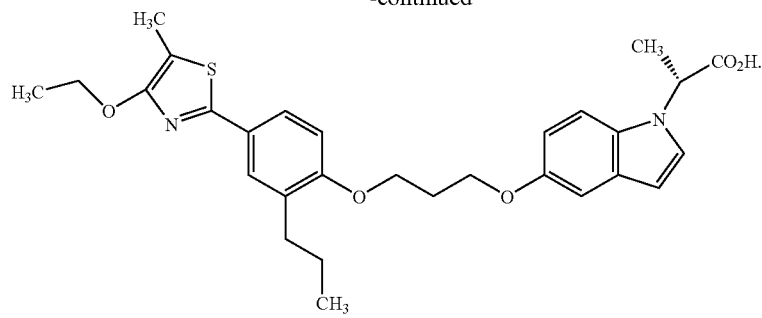

The corresponding racemic ester (266 mg, 0.50 mmol) prepared according to the method described in Example 55 was dissolved in a mixture of 3:3:1 THF, MeOH, and water (7 mL) and LiOH.H$_2$O (118 mg, 4.96 mmol) was added. The mixture was stirred at 50° C. for 3 h. The solvents were evaporated under reduced pressure. The residue was acidified with 1 N HCl. The aqueous layer was immediately extracted with EtOAc. The combined organic layers were dried and concentrated. The crude product was purified by reversed phase HPLC using a gradient of 20 to 100% A (A: CH$_3$CN 0.1% TFA; B: Water 0.1% TFA) to give a racemic mixture of the title compound as a white solid. $^1$H NMR (400 MHz, acetone-d$_6$) δ 7.67-7.65 (m, 2H), 7.35 (d, 1H), 7.32 (d, 1H), 7.12 (d, 1H), 7.02 (d, 1H), 7.85 (dd, 1H), 6.41 (d, 1H), 5.28 (q, 1H), 4.37 (q, 2H), 4.29-4.23 (m, 4H), 2.66 (t, 2H), 2.31 (t, 2H), 2.25 (s, 3H), 1.80 (d, 3H), 1.68-1.62 (m, 2H), 1.36 (t, 3H), 0.96 (t, 3H). LC/MS m/z 523.1 (M+H)$^+$; RT 4.46 min.

The racemic acid mixture (0.088 g) was resolved by chiral HPLC using a Chiral Pak AD-H column eluting with a gradient of 10 to 20% of B (A: hexanes; B: isopropanol) over 20 minutes at a flow-rate of 15 mL/min. A white solid was obtained after concentrating the fractions correlating to the first peak (26.5 mg, RT=14.4 min) designated as the Example 59A. $^1$H NMR (400 MHz, acetone-d$_6$) δ 7.68-7.64 (m, 2H), 7.36 (d, 1H), 7.32 (d, 1H), 7.12 (d, 1H), 7.04 (d, 1H), 6.84 (dd, 1H), 6.40 (d, 1H), 5.28 (q, 1H), 4.37 (q, 2H), 4.31-4.24 (m, 4H), 2.66 (t, 2H), 2.31 (t, 2H), 2.25 (s, 3H), 1.80 (d, 3H), 1.68-1.62 (m, 2H), 1.36 (t, 3H), 0.96 (t, 3H) LC/MS m/z 523.3 (M+H)$^+$; RT=4.47 min. The other enantiomer, designated as Example 59B, was collected from the fractions correlating to the second peak as a white solid (24.4 mg, RT=16.7 min). $^1$H NMR (400 MHz, Acetone d$_6$) δ 7.68-7.64 (m, 2H), 7.36 (d, 1H), 7.32 (d, 1H), 7.12 (d, 1H), 7.04 (d, 1H), 6.84 (dd, 1H), 6.40 (d, 1H), 5.28 (q, 1H), 4.37 (q, 2H), 4.31-4.24 (m, 4H), 2.66 (t, 2H), 2.31 (t, 2H), 2.25 (s, 3H), 1.80 (d, 3H), 1.68-1.62 (m, 2H), 1.36 (t, 3H), 0.96 (t, 3H). LC/MS m/z 523.3 (M+H)$^+$; RT 4.47 min.

Example 60

Preparation of (S)-2-(5-{3-[4-(4-ethoxy-5-methyl-thiazol-2-yl)-2-propyl-phenoxy]-propoxy}-3-methyl-indol-1-yl)-propionic acid and (R)-2-(5-{3-[4-(4-ethoxy-5-methyl-thiazol-2-yl)-2-propyl-phenoxy]-propoxy}-3-methyl-indol-1-yl)-propionic acid

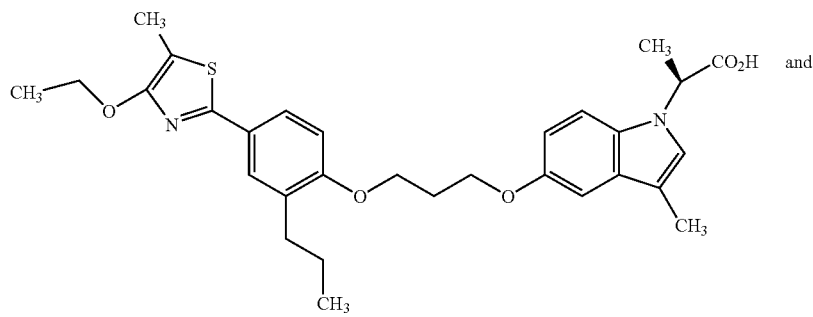

and

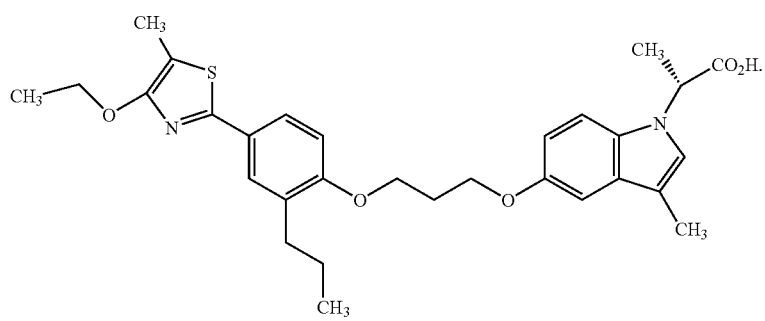

The racemic acid mixture (0.119 g) prepared by the method of Example 59 was resolved by chiral HPLC using a Chiral Pak AD column eluting with a isocratic system (10% isopropanol and 90% hexanes) for 20 minutes at a flow-rate of 15 mL/min. This yielded a white solid (39.8 mg) of the compound, designated as Example 60A, corresponding to the first peak (RT=11.9 min). LC/MS m/z 537.3 (M+H)$^+$; RT 4.60 min. The other enantiomer, designated Example 60B, was collected as a white solid corresponding to the second peak (38.1 mg, RT=14.5 min) LC/MS m/z 537.3 (M+H)$^+$; RT 4.60 min.

Example 61

Preparation of (S)-2-(5-{3-[4-(4,5,6,7-tetrahydro-benzothiazol-2-yl)-phenoxy]-propoxy}-indol-1-yl)-propionic acid and (R)-2-(5-{3-[4-(4,5,6,7-tetrahydro-benzothiazol-2-yl)-phenoxy]-propoxy}-indol-1-yl)-propionic acid

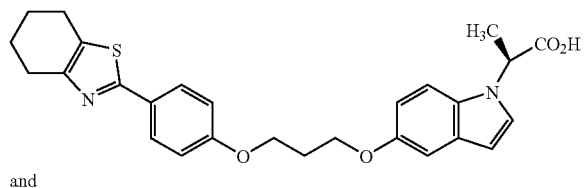

and

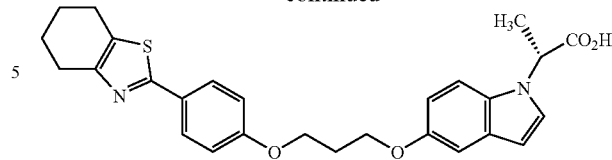

The corresponding racemic acid mixture (0.989 g) prepared according to the method of Example 59 was resolved by chiral HPLC using a Pirkle covalent (R,R) whelk-02 chiral column 20×250 mm, eluting with an isocratic solvent system containing 20% B (A: hexanes; B: 1:1 methanol/ethanol) over 20 minutes at a flow-rate of 25 mL/min. This yielded the compound, designated as Example 61A, as a white solid (182 mg) corresponding to the first peak (RT=14.7 min). LC/MS m/z 477.2 (M+H)$^+$; RT 3.52 min. The other enantiomer, designated as Example 61B, was collected as a white solid (159 mg) correlating to the second peak (RT=16.2 min). LC/MS m/z 477.2 (M+H)$^+$; RT 3.52 min.

Method 10: Preparation of Phenoloxazole Indoles

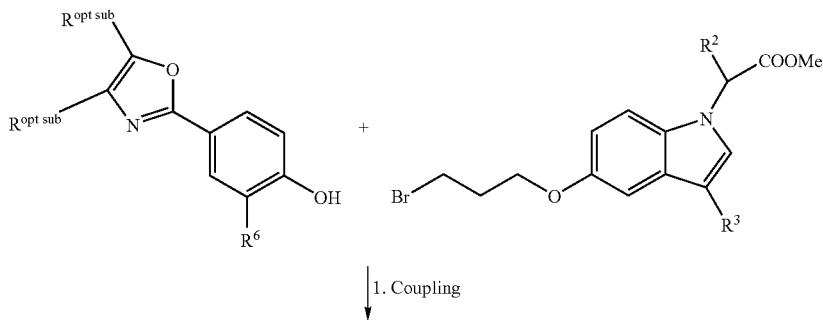

1. Coupling

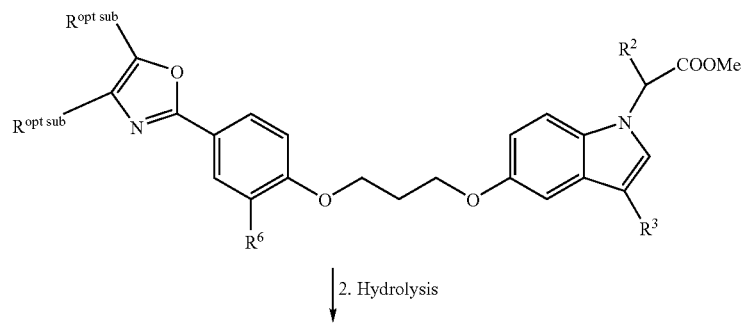

2. Hydrolysis

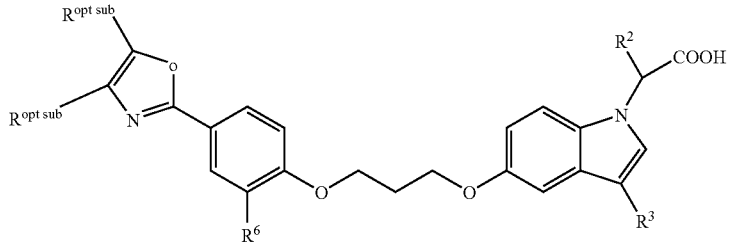

Step 1: Coupling

Example 62

Preparation of 2-(5-{3-[4-(4-ethyl-oxazol-2-yl)-2-methoxy-phenoxy]-propoxy}-indol-1-yl)-propionic acid methyl ester

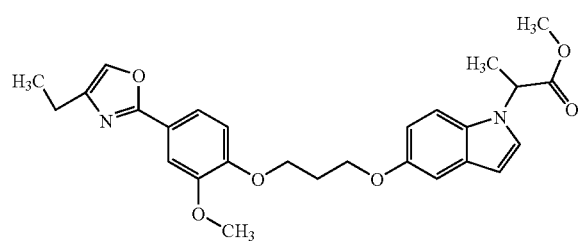

2-[5-(3-Bromo-propoxy)-indol-1-yl]-propionic acid methyl ester (Example 48, 170.20 mg, 0.50 mmol) and 4-(4-ethyl-oxazol-2-yl)-2-methoxy-phenol (Example 39, 109.68 mg, 0.50 mmol) were dissolved in DMF (2 mL) at rt. Cesium carbonate (244.5 mg, 0.75 mmol) was added to the solution, followed by three drops of water. The mixture was stirred at rt for 17 h. The crude reaction mixture was filtered and purified by HPLC. The desired product was isolated as a white solid (143.8 mg, 60.1%). LC/MS m/z 479.3 (M+H)$^+$; RT 3.59 min. $^1$H NMR (400 MHz, CD$_2$Cl$_2$) δ 7.58 (d, 1H), 7.56 (s, 1H), 7.41 (m, 1H), 7.24 (d, 1H), 7.19 (d, 1H), 7.11 (d, 1H), 7.00 (d, 1H), 6.88 (dd, 1H), 6.46 (d, 1H), 5.11 (q, 1H), 4.28 (t, 2H), 4.22 (t, 2H), 3.93 (s, 3H), 3.71 (s, 3H), 2.61 (q, 2H), 2.34 (m, 2H), 1.82 (d, 3H), 1.29 (t, 3H).

Step 2: Hydrolysis

Example 63

Preparation of 2-(5-{3-[4-(4-ethyl-oxazol-2-yl)-2-methoxy-phenoxy]-propoxy}-indol-1-yl)-propionic acid

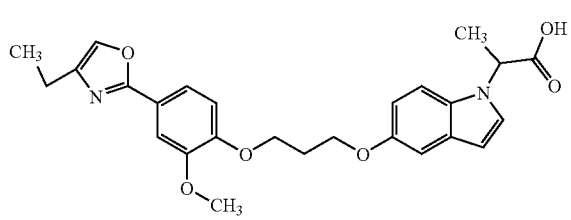

2-(5-{3-[4-(4-Ethyl-oxazol-2-yl)-2-methoxy-phenoxy]-propoxy}-indol-1-yl)-propionic acid methyl ester (Example 62, 129.7 mg, 0.27 mmol) was dissolved in a solution of tetrahydrofuran (2 mL), methanol (1 mL), and water (2 mL). Lithium hydroxide (32.45 mg, 1.36 mmol) was added and the mixture was stirred at rt for 2 h. The solution was concentrated, diluted with water (5 mL), and acidified with 1N HCl. The resulting white precipitate was collected by filtration and dried to give the title compound (100.1 mg, 79.5%). LC/MS m/z 465.1 (M+H)$^+$; RT 3.25 min. $^1$H NMR (400 MHz, DMSO-d$_6$) δ 7.82 (s, 1H), 7.47 (dd, 1H), 7.42 (d, 1H), 7.37 (d, 1H), 7.28 (d, 1H), 7.11 (d, 1H), 7.06 (d, 1H), 6.77 (dd, 1H), 6.34 (d, 1H), 5.24 (q, 1H), 4.19 (t, 2H), 4.12 (t, 2H), 3.82 (s, 3H), 2.52 (m, 2H), 2.20 (m, 2H), 1.68 (d, 3H), 1.19 (t, 3H).

Method 11: Preparation of Phenol 3-Indole Acetic Acid Derivatives

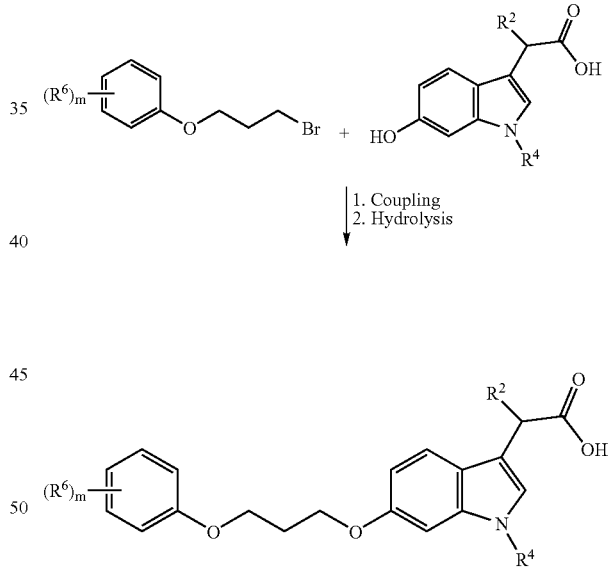

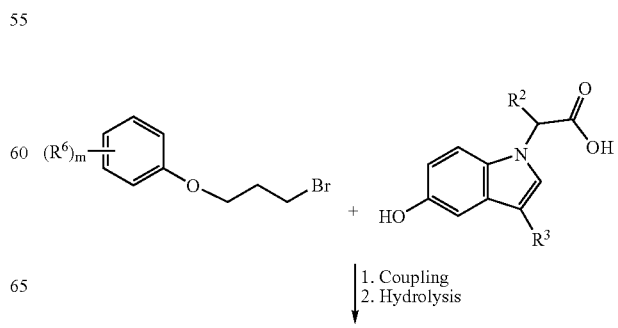

-continued

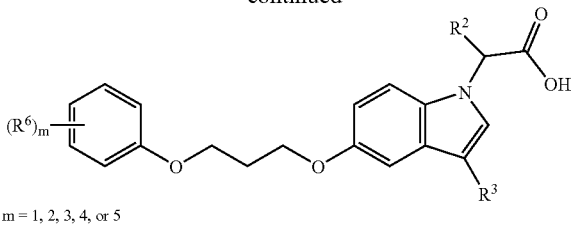

m = 1, 2, 3, 4, or 5

Similar conditions were used in the preparation of 3-indole and 1-indole acetic acid derivatives.

Step 1: Coupling

Example 64

Preparation of {1-acetyl-6-[3-(7-propyl-3-trifluoromethyl-benzo[d]isoxazol-6-yloyl)-propoxy]-1H-indol-3-yl}-acetic acid methyl ester

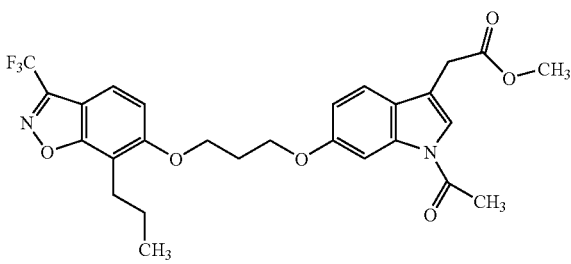

A mixture of (1-acetyl-6-hydroxy-1H-indol-3-yl)-acetic acid methyl ester (Example 14, 90.0 mg, 0.364 mmol), 6-(3-bromo-propoxy)-7-propyl-3-trifluoromethyl-benzo[d]isoxazole (Example 46, 140.0 mg, 0.382 mmol), $Cs_2CO_3$ (124.5 mg, 0.382 mmol), and water (3 drops) in DMF (3.6 mL) was stirred at rt under argon for 20 h. The reaction mixture was loaded on to silica gel and eluted with EtOAc/hexane (5:95) to yield the title compound as a white solid (110.0 mg, 57%). LC/MS m/z 533 (M+H)$^+$, RT 4.25 min; $^1$H NMR (400 MHz, $CDCl_3$) δ 8.08 (s, 1H), 6.92-7.57 (m, 5H), 4.26-4.35 (m, 4H), 3.73 (s, 3H), 3.70 (s, 2H), 2.81-2.93 (m, 2H), 2.61 (s, 3H), 2.35-2.36 (m, 2H), 1.63-1.69 (m, 2H), 0.93 (d, 3H).

Step 2: Hydrolysis

Example 65

Preparation of {6-[3-(7-propyl-3-trifluoromethyl-benzo[d]isoxazol-6-yloxy)-6-propoxy]-1H-indol-3-yl}-acetic acid

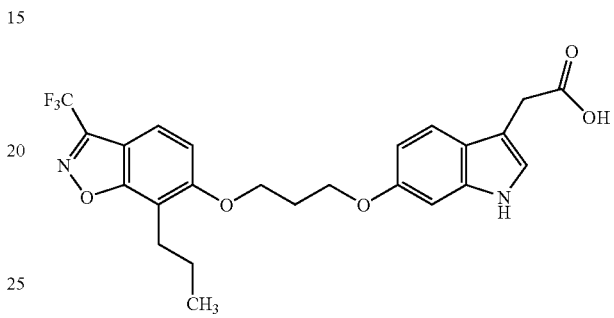

To a solution of {1-acetyl-6-[3-(7-propyl-3-trifluoromethyl-benzo[d]isoxazol-6-yloyl)-propoxy]-1H-indol-3-yl}-acetic acid methyl ester (Example 64, 102.7 mg, 0.193 mmol) in THF (1 mL) was added 1.0 M LiOH solution (0.66 mL) in MeOH/water (1:1). The mixture was heated at 60° C. for 2 h. The solvents were evaporated under reduced pressure. Water was added to dissolve the residue. The pH of the mixture was adjusted to 1-2 with concentrated HCl. The mixture was extracted with dichloromethane (3×20 mL). The combined organic layers were dried over $MgSO_4$, filtered, and concentrated to yield the title compound as a solid (80.1 mg, 80%). LC/MS m/z 477 (M+H)$^+$, RT 3.84 min; $^1$H NMR (400 MHz, DMSO-$d_6$) δ 12.08 (s, 1H), 10.67 (s, 1H), 6.63-7.75 (m, 6H), 4.35 (t, 2H), 4.16 (t, 2H), 3.56 (s, 2H), 2.83-2.87 (m, 2H), 2.22-2.28 (m, 2H), 1.57-1.66 (m, 2H), 0.87 (t, 3H).

Method 12: Preparation of Pyridinethiazole 1-Indoles

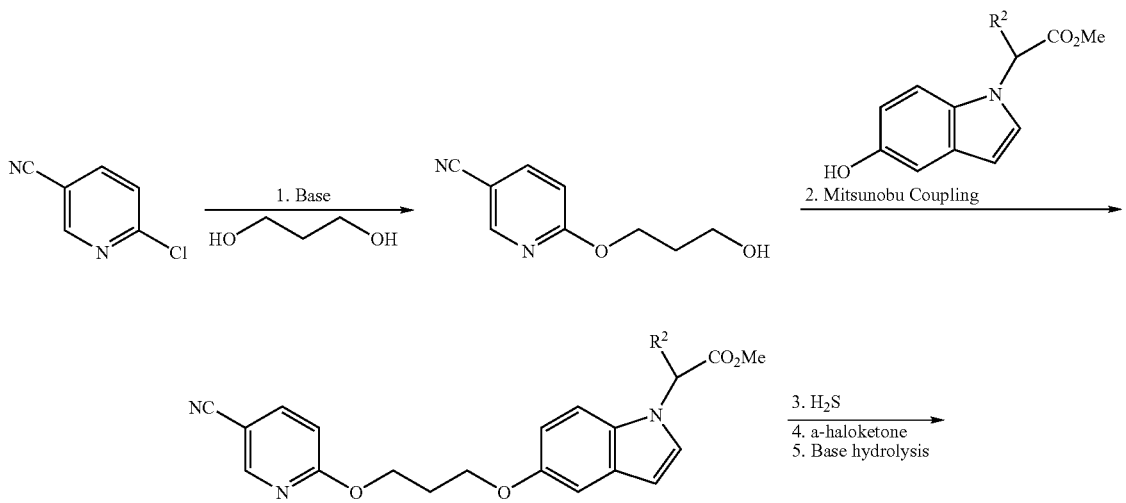

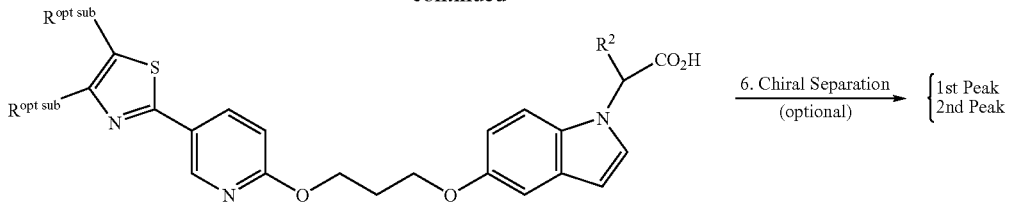

Step 1: Propanediol Addition

Example 66

Preparation of 6-(3-hydroxypropoxy)nicotinonitrile

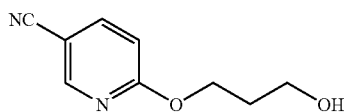

Sodium hydride (0.42 g, 60% suspension in mineral oil, 10.61 mmol) was added to a solution of 1,3-propanediol (2.30 mL, 31.83 mmol) in DMF (22 mL) at 0° C., and the mixture was stirred at rt for 20 minutes. To the resultant pale yellow slurry was added 6-chloronicotinonitrile (1.50 g, 10.61 mmol) in one portion. The mixture was stirred at rt for 18 h. It was then poured into water. The precipitates were filtered and the filtrate was extracted with ethyl acetate. The organic extract was washed with brine, dried over $Na_2SO_4$, filtered, and concentrated under reduced pressure to give the title compound (1.56 g, 83%) as a white solid. $^1$H NMR (300 MHz, $CD_2Cl_2$) δ 8.47 (d, 1H), 7.82-7.79 (m, 1H), 6.84-6.82 (m, 1H), 4.53 (t, 2H), 3.75 (t, 2H), 2.06-1.99 (m, 2H).

Step 2: Mitsunobu Coupling

Example 67

Preparation of methyl 2-(5-{3-[(5-cyano-2-pyridinyl)oxy]propoxy}-1H-indol-1-yl)propanoate

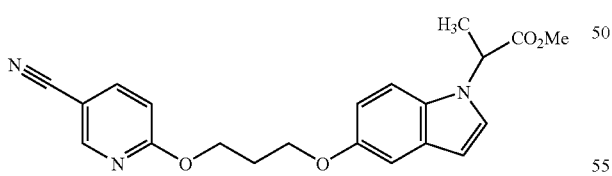

To a solution of 6-(3-hydroxypropoxy)nicotinonitrile (Example 66, 0.55 g, 3.09 mmol) and methyl 2-(5-hydroxy-1H-indol-1-yl)propanoate (Example 7, 0.34 g, 1.55 mmol) in $CH_2Cl_2$ (7.73 mL) were added triphenylphosphine (0.61 g, 2.32 mmol) and 1,1'-(azodicarbonyl)-dipiperidine (0.59 g, 2.32 mmol). The yellow reaction mixture was stirred at rt for 18 h and then concentrated under reduced pressure. The crude residue was purified by silica gel column chromatography (eluting with 67% hexanes/EtOAc) to give the title compound (0.5 g, 85%). $^1$H NMR (400 MHz, $CD_2Cl_2$) δ 8.49 (dd, 1H), 7.79 (dd, 1H), 7.25-7.09 (m, 3H), 6.85-6.83 (m, 2H), 6.47 (d, 1H), 5.11 (qt, 1H), 4.60 (t, 2H), 4.17 (t, 2H), 3.71 (s, 3H), 2.35-2.25 (m, 2H), 1.82 (d, 3H).

Step 3: Thioamide Formation

Example 68

Preparation of methyl 2-[5-(3-{[5-(aminocarbonothioyl)-2-pyridinyl]oxy}propoxy)-1H-indol-1-yl]propanoate

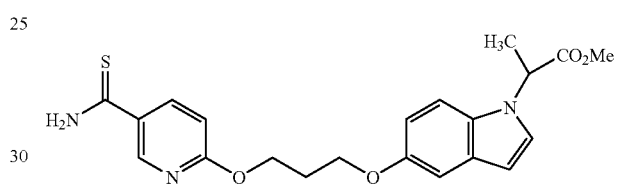

$H_2S$ gas was passed slowly through a solution of methyl 2-(5-{3-[(5-cyano-2-pyridinyl)oxy]propoxy}-1H-indol-1-yl)propanoate (Example 67, 0.50 g, 1.32 mmol) in DMF (7.80 mL) for 20 minutes at rt. Diethylamine (0.21 mL, 2.37 mmol) was added in one portion, and the resultant light green solution was heated at 60° C. for 3 h. The reaction mixture was purged with a stream of argon, and then concentrated under reduced pressure. The desired compound (0.49 g, 90%) was isolated by column chromatography (50% hexanes in EtOAc) as a bright yellow solid. $^1$H NMR (400 MHz, $CD_2Cl_2$) δ 8.63 (dd, 1H), 8.16 (dd, 1H), 7.25-7.08 (m, 3H), 6.86-6.74 (m, 2H), 6.46 (d, 1H), 5.16 (qt, 1H), 4.59 (t, 2H), 4.17 (t, 2H), 3.71 (s, 3H), 2.35-2.25 (m, 2H), 1.82 (d, 3H).

Step 4: Thiazole Formation

Example 69

Preparation of methyl 2-[5-(3-{[5-(4-ethyl-1,3-thiazol-2-yl)-2-pyridinyl]oxy}propoxy)-1H-indol-1-yl]propanoate

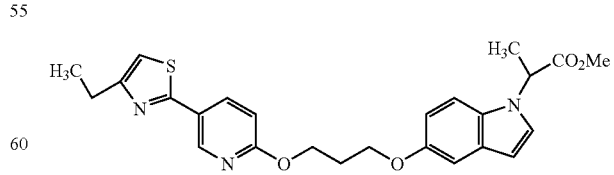

A mixture of methyl 2-[5-(3-{[5-(aminocarbonothioyl)-2-pyridinyl]oxy}propoxy)-1H-indol-1-yl]propanoate (Example 68, 0.1 g, 0.24 mmol) and 1-bromo-2-butanone (0.05 g, 0.29 mmol) in ethanol (8.90 mL) was heated under argon at 80° C. for 3 h. The resulting mixture was concentrated. The title compound (0.11 g, 98%) was isolated by column chromatography (2:1 hexanes/EtOAc). ¹H NMR (400 MHz, CD₂Cl₂) δ 8.69 (dd, 1H), 8.13 (dd, 1H), 7.25-7.10 (m, 3H), 6.90-6.81 (m, 3H), 6.47 (d, 1H), 5.12 (qt, 1H), 4.58 (t, 2H), 4.20 (t, 2H), 3.71 (s, 3H), 2.85 (qt, 2H), 2.36-2.24 (m, 2H), 1.82 (d, 3H), 1.35 (t, 3H).

Step 5: Hydrolysis

Example 70

Preparation of 2-[5-(3-{[5-(4-ethyl-1,3-thiazol-2-yl)-2-pyridinyl]oxy}propoxy)-1H-indol-1-yl]propanoic acid

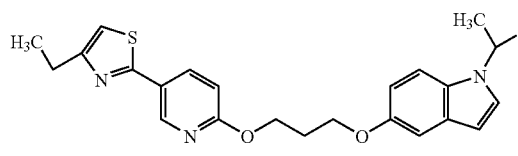

Lithium hydroxide (0.05 g, 2.15 mmol) was added to a solution of methyl 2-[5-(3-{[5-(4-ethyl-1,3-thiazol-2-yl)-2-pyridinyl]oxy}propoxy)-1H-indol-1-yl]propanoate (Example 69, 0.1 g, 0.21 mmol) in a mixture of THF (2 mL), methanol (2 mL), and water (1 mL). The reaction mixture was stirred at rt for 18 h and then concentrated under reduced pressure. The residue was diluted with water and acidified with 5% H₃PO₄. The aqueous layer was extracted with ethyl acetate. The combined organic extracts were dried over Na₂SO₄, filtered, and concentrated to give the title compound as a solid (0.079 g, 82%). ¹H NMR (400 MHz, CD₂Cl₂) δ 8.45 (dd, ₁H), 7.94 (dd, 1H), 7.08-6.62 (m, 6H), 6.22 (d, 1H), 4.94 (qt, 1H), 4.37 (t, 2H), 4.00 (t, 2H), 2.66 (qt, 2H), 2.31-2.07 (m, 2H), 1.60 (d, 3H), 1.15 (t, 3H).

Step 6: Chiral Separation

Example 71

Separation of (2R)-2-[5-(3-{[5-(4-ethyl-1,3-thiazol-2-yl)-2-pyridinyl]oxy}propoxy)-1H-indol-1-yl]propanoic acid and (2S)-2-[5-(3-{[5-(4-ethyl-1,3-thiazol-2-yl)-2-pyridinyl]oxy}propoxy)-1H-indol-1-yl]propanoic acid

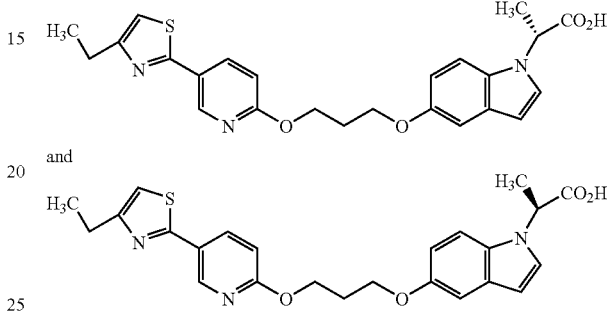

and

The racemic mixture of 2-[5-(3-{[5-(4-ethyl-1,3-thiazol-2-yl)-2-pyridinyl]oxy}propoxy)-1H-indol-1-yl]propanoic acid (Example 70, 0.3 g) was resolved by HPLC using a Pirkle covalent (R,R) whelk-02 chiral column, eluting with a gradient of 20 to 46% B (A: hexanes; B: 1:1 Methanol/Ethanol) over 13 minutes at a flow-rate of 25 mL/min. This yielded 91 mg of the enantiomer, designated as Example 71A, with the retention time of 11.11 minutes. The other enantiomer, designated Example 71B, was eluted at retention time 9.62 minutes. ¹H NMR (400 MHz, CD₂Cl₂) δ 8.54 (dd, 1H), 8.01 (dd, 1H), 7.13-6.72 (m, 6H), 6.25 (d, 1H), 4.96 (qt, 1H), 4.44 (t, 2H), 4.08 (t, 2H), 2.74 (qt, 2H), 2.36-2.13 (m, 2H), 1.70 (d, 3H), 1.21 (t, 3H).

Method 13: Preparation of Pyridinethiazole 1-Indoles

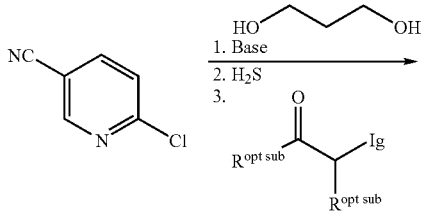

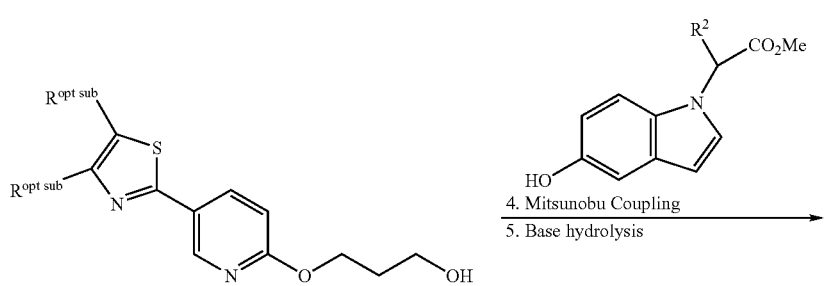

-continued

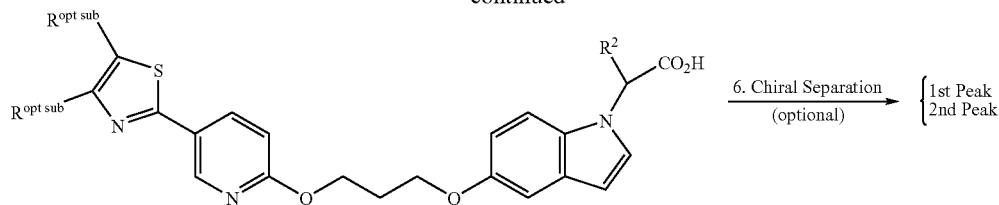

Step 1 and 2

Example 72

Preparation of 6-(3-hydroxy-propoxy)-thionicotinamide

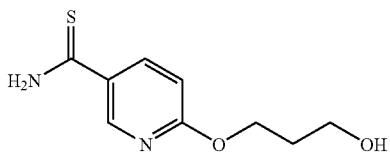

Through a solution of 6-(3-hydroxypropoxy)nicotinonitrile (Example 66, 16 g, 89.79 mmol) in DMF (450 mL) was passed $H_2S$ for 3 h at rt. The reaction mixture turned purple. Diethylamine (9.85 g, 134.69 mmol) was added slowly. The resultant dark green solution was heated at 60° C. for 2 h. The resulting mixture was concentrated under reduced pressure and purified by flash chromatography with a gradient of EtOAc in hexanes from 50 to 100%. The title compound was collected as a yellow solid (18.9 g, 98%). $^1H$ NMR (400 MHz, acetone-$d_6$) δ 8.98-8.87 (br, 2H), 8.80-8.79 (m, 1H), 8.29 (dd, 1H), 6.77 (dd, 1H), 4.48 (t, 2H), 3.74-3.68 (m, 3H), 1.99 (t, 2H). LC/MS m/z 213.2 (M+H)$^+$; RT 0.50 min.

Step 3: Thiazole Formation

Example 73

Preparation of 3-[5-(4-ethyl-thiazol-2-yl)-pyridin-2-yloxy]-propan-1-ol

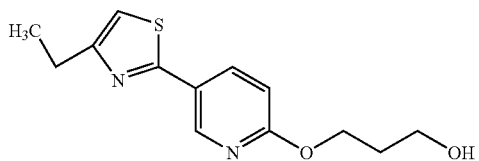

To a solution of 6-(3-hydroxy-propoxy)-thionicotinamide (Example 72, 8.8 g, 41.46 mmol) in EtOH (205 mL) at rt was added 1-bromo-2-butanone. The reaction mixture was then heated at 70° C. for 3 h. Upon completion, triethylamine was added and the volatiles were removed under reduced pressure. The crude material was suspended in $CH_2Cl_2$ and purified by flash chromatography. The column was eluted with a mixture of EtOAc/hexanes (30 to 50% EtOAc) to give the title compound as a white solid (10.04 g, 91%) after concentration of the chromatography fractions. $^1H$ NMR (400 MHz, acetone-$d_6$) δ 8.70 (s, 1H), 8.19 (dd, 1H), 7.15 (s, 1H), 6.86 (d, 1H), 4.48 (t, 2H), 3.74-3.71 (m, 3H), 2.83 (q, 2H), 2.01-1.98 (m, 2H), 1.32 (t, 3H). LC/MS m/z 265.3 (M+H)$^+$; RT 2.12 min.

Step 4: Coupling

Example 74

Preparation of (R)-2-(5-{3-[5-(4-ethyl-thiazol-2-yl)-pyridin-2-yloxy]-propoxy}-indol-1-yl)-propionic acid methyl ester

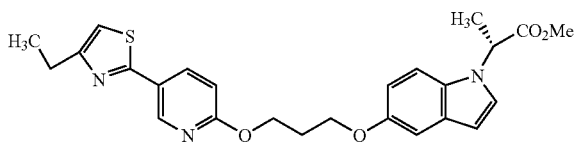

A solution of 3-[5-(4-ethyl-thiazol-2-yl)-pyridin-2-yloxy]-propan-1-ol (Example 73, 7.0 g, 0.025 mol), (R-2-(5-hydroxy-indol-1-yl)-propionic acid methyl ester (Example 8, 4.961 g, 0.023 mol), and triphenylphosphine (7.716 g, 0.029 mol) in dichloromethane (60 mL) was treated with a solution of 1,1'-(azodicarbonyl)-dipiperidine (7.423 g, 0.029 mol) in dichloromethane (45 mL) slowly over 25 minutes while maintaining the temperature around 25° C. The resulting suspension was stirred at rt for 18 h. Upon completion, the solvent was removed under vacuum and the crude product was purified by silica gel chromatography using a gradient of 5-35% ethyl acetate/hexanes to give 7.3 g (69%) of the title compound as a beige solid. The product was characterized as in Example 69.

Step 5: Hydrolysis

Example 75

Preparation of (R)-2-(5-{3-[5-(4-ethyl-thiazol-2-yl)-pyridin-2-yloxy]-propoxy}-indol-1-yl)-propionic acid

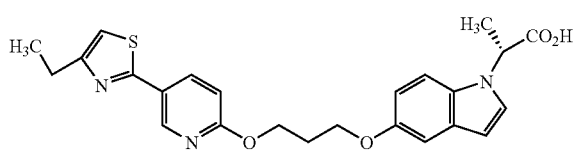

A solution of (R)-2-(5-{3-[5-(4-ethyl-thiazol-2-yl)-pyridin-2-yloxy]-propoxy}-indol-1-yl)-propionic acid methyl ester (Example 74, 7.0 g, 0.015 mol) in THF (51 mL) and ethanol (26 mL) was treated with a solution of lithium hydroxide (0.432 g, 0.018 mol) in water (51 mL). The slightly hazy solution was stirred at rt for 2.5 h. The organic solvents were removed under vacuum at 30° C. The remaining suspension was diluted with water (50 mL). The pH of the mixture was adjusted to ~5 using 1N HCl, and the mixture was stirred at rt for 1 h. The solid was filtered, washed with water (20 mL) and dried under high vacuum for 18-20 h.

To the resultant carboxylic acid (6.3 g) was added acetone (105 mL) and (R)-α-methylbenzylamine (1.93 mL, 0.015 mol). The reaction mixture was heated to ~45° C. to achieve dissolution. The hot solution was gravity filtered and allowed to cool to rt. It was then stirred at rt for 16-18 h. The resulting precipitate was filtered, washed with acetone (13 mL), and dried under vacuum for 4-5 h. The dry salt was suspended in water (250 mL) and the pH of the suspension was adjusted to ~5 with 1N HCl. The mixture was stirred for 1.5 h at rt, then filtered. The filter cake was washed with water (50 mL) and dried under high vacuum at rt for 18-20 h to give 3.6 g of the acid as a beige solid. The product was recrystallized from ethanol (52 mL) to give 2.7 g (40%) of the title compound (97% ee by chiral HPLC).

Chiral HPLC conditions: Column: Chiracel AD, 4.6 (I.D.)×250 mm; Mobile Phase: A: 0.1% TFA in Hexanes; B: 0.1% TFA in IPA; Isocratic: 70% A (30% B) for 15 min; Flow rate: 1.0 mL/min; Detector (UV): 284 nm; retention time of the desired enantiomer: 11.53 min.

Method 14: Preparation of Pyridinethiazole Indoles

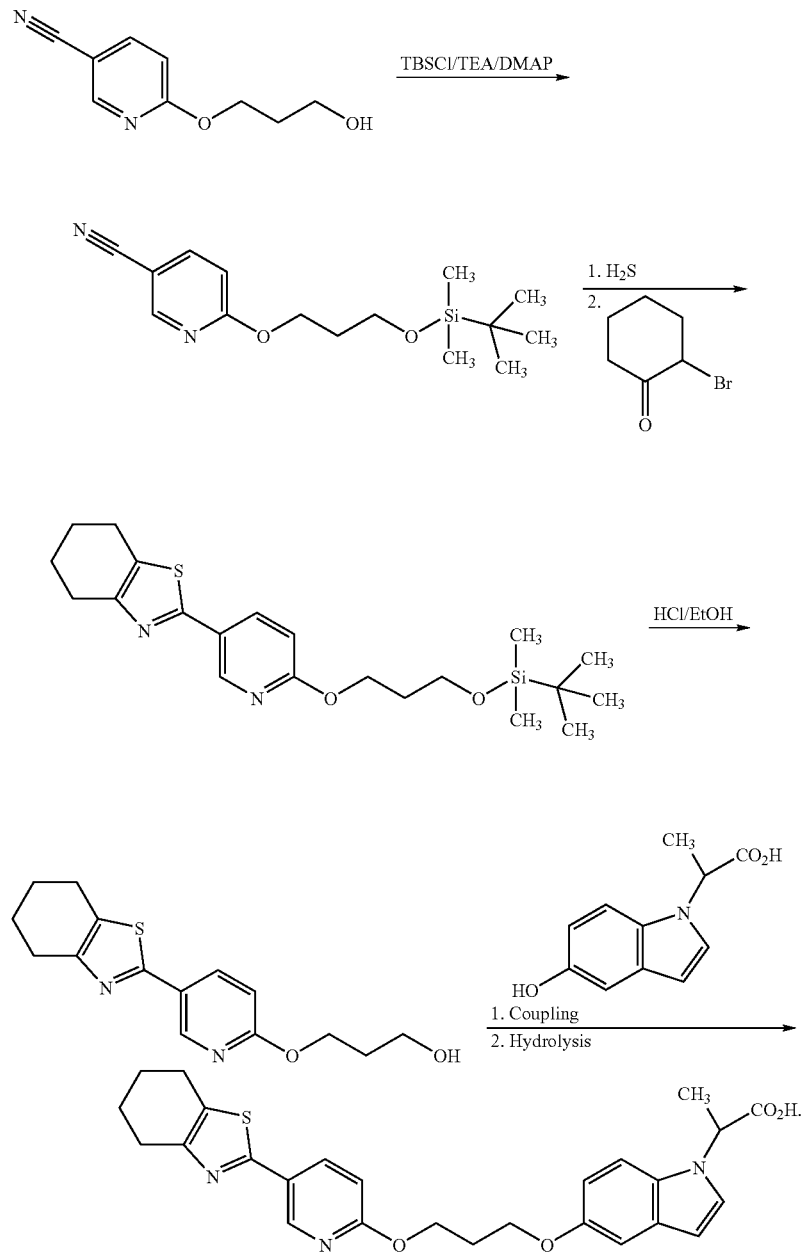

Step 1: Protection of Alcohol

Example 76

Preparation of 6-[3-(tert-butyl-dimethyl-silanyloxy)-propoxy]-nicotinonitrile

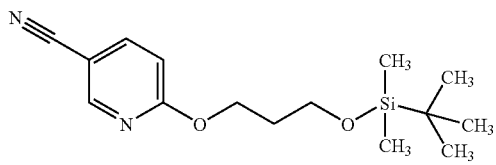

To a solution of t-butyldimethylsilyl chloride (0.93 g, 6.17 mmol) in CH$_2$Cl$_2$ (25 mL) was added 6-(3-hydroxypropoxy) nicotinonitrile (Example 66, 1 g, 5.61 mmol), Et$_3$N (0.62 g, 6.17 mmol), and DMAP (0.014 g, 0.11 mmol). The mixture was stirred at rt for 18 h. The reaction mixture was diluted with brine and extracted with CH$_2$Cl$_2$ (3×25 mL). The combined organic layers were dried over Na$_2$SO$_4$, filtered, and concentrated under reduced pressure. The crude residue was purified by silica gel flash chromatography (2:1 hexanes/EtOAc) to give the title compound (1.14 g, 69%). $^1$H NMR (400 MHz, CDCl$_3$) δ 8.40 (dd, 1H), 7.69 (dd, 1H), 6.72 (dd, 1H), 4.40 (t, 2H), 3.73 (t, 2H), 1.90-1.98 (m, 2H), 0.82 (s, 9H), 0.02 (s, 6H).

Step 2: Thiazole Formation

Example 77

Preparation of 2-{6-[3-(tert-butyl-dimethyl-silanyloxy)-propoxy]-pyridin-3-yl}-4,5,6,7-tetrahydro-benzothiazole

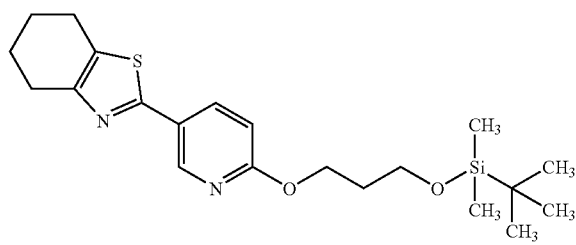

H$_2$S gas was passed slowly through a solution of 6-[3-(tert-butyl-dimethyl-silanyloxy)-propoxy]-nicotinonitrile (Example 76, 1.14 g, 3.90 mmol) in DMF (25.0 mL) at rt for 30 minutes. Diethylamine (0.60 mL, 5.85 mmol) was added in one portion, and the resultant light green solution was heated at 60° C. for 4 h. The reaction mixture was purged with a stream of argon, and concentrated under reduced pressure. The crude product was filtered through a short pad of silica gel and eluted with EtOAc. The solvent was removed under reduced pressure. The residue was treated with a solution of 2-chlorocyclohexanone (0.244 g, 1.80 mmol) in 10 mL 1:1 toluene/dioxane. The flask was connected to a Dean-Stark apparatus and heated at 150° C. for 18 h. The reaction mixture was concentrated under reduced pressure, the residue washed with water, and extracted with ethyl acetate. The combined organic extracts were dried over Na$_2$SO$_4$, filtered, and concentrated under reduced pressure. The crude material was purified by silica gel flash chromatography (15% EtOAc in hexanes) to give the title compound (0.29 g, 18%). $^1$H NMR (400 MHz, CDCl$_3$) δ 8.58 (dd, 1H), 8.02 (dd, 1H), 6.65 (dd, 1H), 4.36 (t, 2H), 3.75 (t, 2H), 2.70-2.82 (m, 4H), 1.90-1.98 (m, 2H), 1.80-1.90 (m, 4H), 0.82 (s, 9H), 0.02 (s, 6H).

Step 3: Deprotection to Alcohol

Example 78

Preparation of 3-[5-(4,5,6,7-tetrahydro-benzothiazol-2-yl)-pyridin-2-yloxy]-propan-1-ol

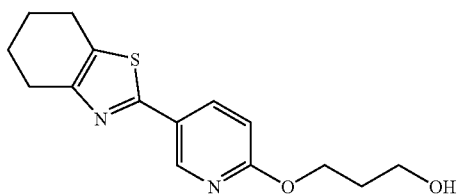

A mixture of 2-{6-[3-(tert-butyl-dimethyl-silanyloxy)-propoxy]-pyridin-3-yl}-4,5,6,7-tetrahydro-benzothiazole (Example 77, 0.29 g, 0.71 mmol) in ethanol/HCl/water (95:1:4; 10 mL) was stirred at rt for 18 h, and then concentrated under reduced pressure. The residue was purified by silica gel flash chromatography (1:4 MeOH/CH$_2$Cl$_2$) to give the title compound (0.098 g, 46%). $^1$H NMR (400 MHz, CDCl$_3$) δ 8.60 (dd, 1H), 8.10 (dd, 1H), 6.75 (dd, 1H), 4.51 (t, 2H), 3.73 (t, 2H), 2.95-3.10 (broad s, 1H), 2.80-2.86 (m, 4H), 2.00-2.12 (m, 2H), 1.80-1.96 (m, 4H).

Step 4 and 5: Coupling and Hydrolysis

Example 79

Preparation of 2-(5-{3-[5-(4,5,6,7-tetrahydro-benzothiazol-2-yl)-pyridin-2-yloxy]-propoxy}-indol-1-yl)-propionic acid

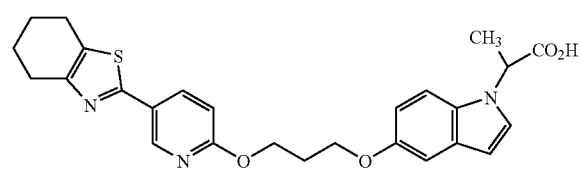

To a solution of 3-[5-(4,5,6,7-tetrahydro-benzothiazol-2-yl)-pyridin-2-yloxy]-propan-1-ol (Example 78, 0.098 g, 0.34 mmol) and 2-(5-hydroxy-indol-1-yl)-propionic acid methyl ester (Example 7, 0.067 g, 0.31 mmol) in CH$_2$Cl$_2$ (10 mL) were added triphenylphosphine (0.161 g, 0.61 mmol) and 1,1'-(azodicarbonyl)-dipiperidine (0.155 g, 0.61 mmol). The yellow reaction mixture was stirred at rt for 18 h, then diluted with 20 mL hexanes, and filtered through a short pad of silica gel. The filtrate was concentrated under reduced pressure, and the residue (0.065 g) dissolved in 5 mL of a mixture of methanol/THF/water (2:2:1). LiOH (9.1 mg, 0.37 mmol) was added. The mixture was stirred at rt for 18 h and concentrated under reduced pressure. The residue was taken up in water and washed with ether. The aqueous layer was acidified to pH 3.5 and extracted with ethyl acetate. The combined organic layers were dried over Na$_2$SO$_4$, filtered, and concentrated to give the title compound (7 mg, 4%). $^1$H NMR (400 MHz, acetone-d$_6$) δ 8.20 (dd, 1H), 7.90 (dd, 1H), 7.35 (s, 1H), 7.29 (dd, 1H), 7.11 (s, 1H), 6.85 (dd, 1H), 6.50 (dd, 1H), 6.39 (s, 1H), 5.25-5.35 (m, 1H), 4.31 (t, 2H), 4.31 (t, 2H), 4.08 (t, 2H), 2.95-3.05 (br s, 1H), 2.70-2.78 (m, 4H), 2.30-2.35 (m, 2H), 1.70-1.94 (m, 4H). LC/MS m/z 478.2 (M+H)$^+$, RT 2.90 min.

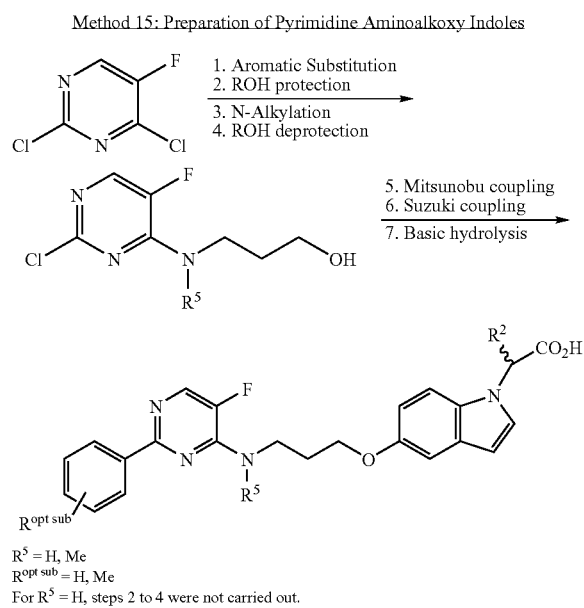

Method 15: Preparation of Pyrimidine Aminoalkoxy Indoles

1. Aromatic Substitution
2. ROH protection
3. N-Alkylation
4. ROH deprotection

5. Mitsunobu coupling
6. Suzuki coupling
7. Basic hydrolysis

R$^5$ = H, Me
R$^{opt\ sub}$ = H, Me
For R$^5$ = H, steps 2 to 4 were not carried out.

Step 1: Aromatic Substitution

Example 80

Preparation of 3-(2-chloro-5-fluoro-pyrimidin-4-ylamino)-propan-1-ol

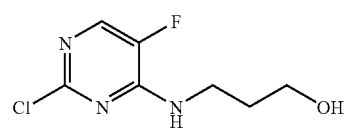

To a solution of 2,4-dichloro-5-fluoropyrimidine (15.0 g, 89.8 mmol) in ethanol (300 mL) were added 3-amino-1-propanol (8.23 mL, 107.8 mmol) and sodium carbonate (47.6 g, 449 mmol). The reaction mixture was vigorously stirred at rt for 72 h. Then the mixture was filtered through Celite®. The filtrate was concentrated under reduced pressure, and the residue was purified by silica gel flash chromatography (100% EtOAc) to give the title compound as a white solid (9.5 g, 51%). LC/MS m/z 206.3 (M+H)$^+$; $^1$H NMR (300 MHz, CD$_2$Cl$_2$) δ 1.85 (quintet, 2H), 3.55 (t, 2H), 3.65 (t, 2H), 4.85-4.98 (br, 2H), 7.85 (d, 1H).

Step 2: Protection of Alcohol

Example 81

Preparation of N-(3-{[tert-butyl(dimethyl)silyl]oxy}propyl)-2-chloro-5-fluoro-4-pyrimidinamine

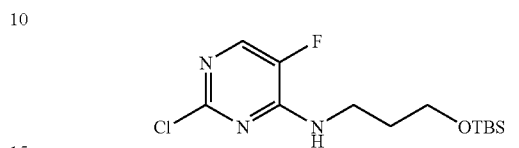

To a solution of t-butyldimethylsilyl chloride (1.63 g, 10.70 mmol) in dichloromethane (48.63 mL) was added 3-[(2-chloro-5-fluoro-4-pyrimidinyl)amino]-1-propanol (Example 80, 2.0 g, 9.73 mmol), followed by triethylamine (1.49 mL, 10.70 mmol) and dimethylaminopyridine (0.02 g, 0.19 mmol). The resulting cloudy mixture was stirred at rt for 18 h and then diluted with dichloromethane (80 mL). The mixture was washed with water (50 mL), dried over magnesium sulfate, and concentrated. The product was purified by column chromatography (67% hexanes in EtOAc) to give the title compound as a white solid (2.68 g, 86%). $^1$H NMR (300 MHz, CD$_2$Cl$_2$) δ 7.78 (d, 1H), 3.64-3.59 (m, 2H), 3.44-3.41 (m, 2H), 1.82-1.73 (m, 2H), 0.84 (s, 9H), 0.001 (s, 6H).

Step 3: N-Alkylation

Example 82

Preparation of N-(3-{[tert-butyl(dimethyl)silyl]oxy}propyl)-2-chloro-5-fluoro-N-methyl-4-pyrimidinamine

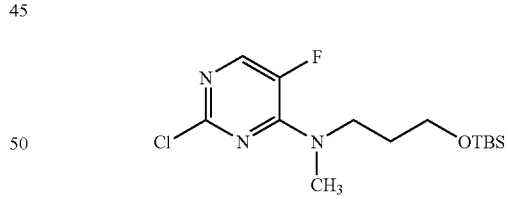

Sodium hydride (0.4 g, 16.76 mmol) was added to a solution of N-(3-{[tert-butyl(dimethyl)silyl]oxy}propyl)-2-chloro-5-fluoro-4-pyrimidinamine (Example 81, 2.68 g, 8.38 mmol) in DMF (41.90 mL). The resulting mixture was stirred at rt for 30 minutes. Methyl iodide (2.09 mL, 33.51 mmol) was added. The mixture was stirred at rt for additional 18 h, then quenched with water, and extracted with ether. The combined ether extracts were washed with water (25 mL), brine (40 mL), dried over magnesium sulfate, filtered, and concentrated. The title compound (2.76 g, 99%) was obtained after column chromatography (67% hexanes in EtOAc). $^1$H NMR (300 MHz, CD$_2$Cl$_2$) δ 7.78 (d, 1H), 3.64-3.59 (m, 4H), 3.24 (d, 3H), 1.82-1.73 (m, 2H), 0.84 (s, 9H), 0.001 (s, 6H).

Step 4: Deprotection to Alcohol

Example 83

Preparation of 3-[(2-chloro-5-fluoro-4-pyrimidinyl)(methyl)amino]-1-propanol

A mixture of N-(3-{[tert-butyl(dimethyl)silyl]oxy}propyl)-2-chloro-5-fluoro-N-methyl-4-pyrimidinamine (Example 82, 2.22 g, 6.65 mmol) in ethanol/HCl/water (95:1:4, 50 mL) was stirred at rt for 18 h and then concentrated under reduced pressure. The residue was passed through a plug of silica gel to give the title compound (1.13 g, 77%) as a viscous yellow oil. $^1$H NMR (300 MHz, DMSO-$d_6$) δ 8.08 (d, 1H), 3.59 (t, 2H), 3.43 (t, 2H), 3.24 (d, 3H), 1.74-1.71 (m, 2H).

Step 5: Mitsunobu Coupling

Example 84

Preparation of methyl (5-{3-[(2-chloro-5-fluoro-4-pyrimidinyl)(methyl)amino]propoxy}-1H-indol-1-yl)acetate

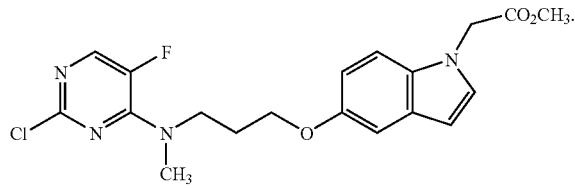

To a solution of 3-[(2-chloro-5-fluoro-4-pyrimidinyl)(methyl)amino]-1-propanol (Example 83, 0.60 g, 2.73 mmol) and methyl (5-hydroxy-1H-indol-1-yl)acetate (Example 9, 0.37 g, 1.82 mmol) in dichloromethane (9 mL) was added triphenylphosphine (0.70 g, 2.73 mmol) and 1,1'-(azodicarbonyl)-dipiperidine (0.72 g, 2.73 mmol) under argon. The golden yellow mixture was stirred at rt for 18 h. The desired product (0.42 g, 56%) was obtained after column chromatography (67% hexanes in EtOAc). $^1$H NMR (300 MHz, CD$_2$Cl$_2$) δ 7.85 (d, 1H), 7.15-7.07 (m, 3H), 6.88-6.83 (m, 1H), 6.47-6.46 (m, 1H), 4.85 (s, 2H), 4.07 (t, 2H), 3.84 (t, 2H), 3.76 (s, 3H), 3.26 (d, 3H), 2.20-2.13 (m, 2H).

Example 85

Preparation of 2-{5-[3-(2-chloro-5-fluoro-pyrimidin-4-ylamino)-propoxy]-indol-1-yl}-propionic acid methyl ester

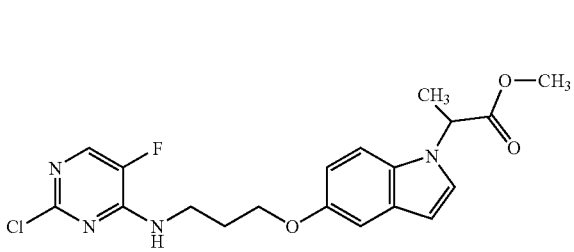

To a solution of 3-(2-chloro-5-fluoro-pyrimidin-4-ylamino)-propan-1-ol (Example 80, 0.66 g, 3.20 mmol) and 2-(5-hydroxy-indol-1-yl)-propionic acid methyl ester (Example 7, 0.47 g, 2.13 mmol) in dichloromethane (10.80 mL) was added triphenylphosphine (0.85 g, 3.20 mmol) and 1,1'-(azodicarbonyl)-dipiperidine (0.82 g, 3.20 mmol) under argon. The golden yellow mixture was stirred at rt for 18 h. The desired product (0.54 g, 59%) was obtained after column chromatography (67% hexanes in EtOAc). $^1$H NMR (300 MHz, CD$_3$OD) δ 7.85 (d, 1H), 7.27-7.06 (m, 3H), 6.82-6.79 (m, 1H), 6.40 (d, 1H), 5.24 (q, 1H), 4.11-4.07 (m, 2H), 3.70-3.67 (m, 5H), 2.15-2.09 (m, 2H), 1.77 (d, 3H).

Step 6: Suzuki Coupling

Example 86

Preparation of methyl (5-{3-[[5-fluoro-2-(4-methoxyphenyl)-4-pyrimidinyl](methyl)amino]propoxy}-1H-indol-1-yl)acetate

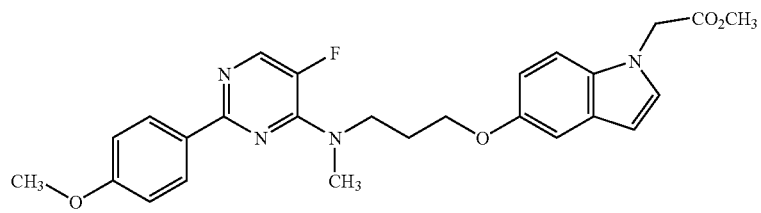

To a solution of methyl (5-{3-[(2-chloro-5-fluoro-4-pyrimidinyl)(methyl)amino]propoxy}-1H-indol-1-yl)acetate (Example 84, 0.1 g, 0.25 mmol) in toluene (3.75 mL), dioxane (0.75 mL), and water (0.88 mL) were added sodium carbonate (0.26 g, 2.46 mmol), 4-methoxyphenyl boronic acid (0.15 g, 0.98 mmol), and PdCl$_2$(dppf)(CH$_2$Cl$_2$) (0.04 g, 0.05 mmol). The mixture was heated at 80° C. for 4 h and then concentrated under reduced pressure. The product (0.11 g, 94%) was obtained after column chromatography (67% hexanes in EtOAc). $^1$H NMR (300 MHz, CD$_2$Cl$_2$) δ 8.31 (d, 2H), 8.06 (d, 1H), 7.12-7.07 (m, 3H), 6.95-6.87 (m, 3H), 6.41 (d, 1H), 4.85 (s, 2H), 4.11 (t, 2H), 3.94 (t, 2H), 3.86 (s, 3H), 3.76 (s, 3H), 3.35 (d, 3H), 2.26-2.20 (m, 2H).

Step 7: Hydrolysis

Example 87

Preparation of (5-{3-[[5-fluoro-2-(4-methoxyphenyl)-4-pyrimidinyl](methyl)amino]propoxy}-1H-indol-1-yl)acetic acid

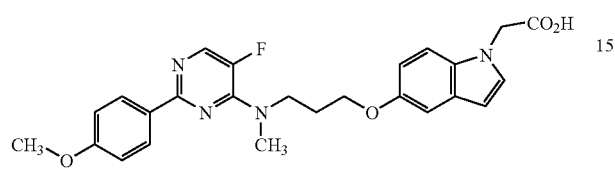

To a solution of methyl (5-{3-[[5-fluoro-2-(4-methoxyphenyl)-4-pyrimidinyl](methyl)amino]propoxy}-1H-indol-1-yl)acetate (Example 86, 0.1 g, 0.20 mmol) in methanol (2 mL), THF (2.00 mL), and water (1.00 mL) was added lithium hydroxide (0.05 g, 1.99 mmol). The mixture was stirred at rt for 18 h and then concentrated under reduced pressure. The residue was taken up in water and washed with ether. The aqueous layer was acidified to pH 3.5 and extracted with ethyl acetate. The combined organic layers were dried over sodium sulfate and concentrated to give the title compound (0.092 g, 100%). $^1$H NMR (300 MHz, CD$_3$OD) δ 8.20-8.17 (m, 2H), 8.03-8.01 (m, 1H), 7.18-6.78 (m, 6H), 6.33-6.30 (m, 1H), 4.74 (s, 2H), 4.11 (t, 2H), 3.94 (t, 2H), 3.83 (s, 3H), 3.36-3.34 (m, 3H), 2.26-2.20 (m, 2H). LC/MS m/z 465.2 (M+H)$^+$, RT 2.51 min.

Method 16: Preparation of Pyrimidine Aminoalkoxy Indoles

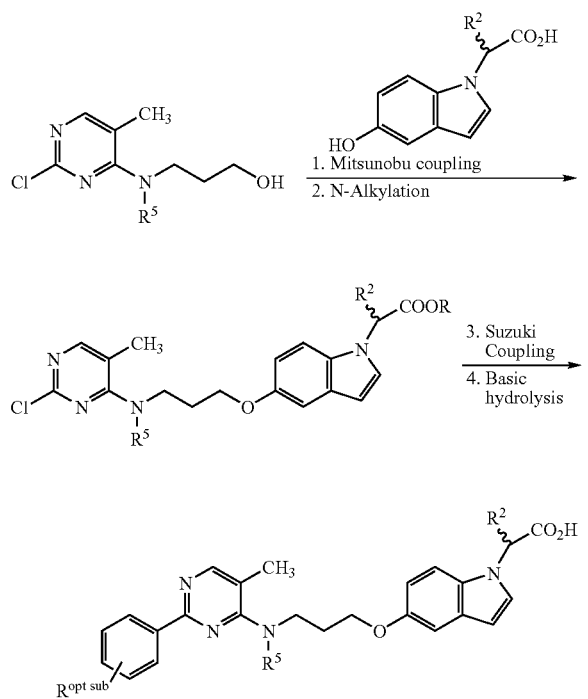

Step 1: Mitsunobu Coupling

Example 88

Preparation of (2-chloro-5-methyl-pyrimidin-4-yl)-[3-(1H-indol-5-yloxy)-propyl]-methyl-amine

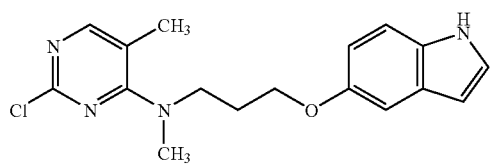

To a solution of 3-[(2-chloro-5-methyl-4-pyrimidinyl)(methyl)amino]-1-propanol (0.316 g, 1.47 mmol) (prepared in similar fashion as Example 83) and 5-hydroxyindole (0.195 g, 1.47 mmol) in dichloromethane (7 mL) was added triphenylphosphine (1.15 g, 4.40 mmol) and 1,1'-(azodicarbonyl)dipiperidine (1.11 g, 4.40 mmol) under argon. The golden yellow mixture was stirred at rt for 24 h. The desired product (0.117 g, 24%) was obtained after column chromatography (50% hexanes in EtOAc). LC/MS m/z 331.3 (M+H)$^+$, RT 2.76 min.

Step 2

Example 89

Preparation of (5-{3-[(2-chloro-5-methyl-pyrimidin-4-yl)-methyl-amino]-propoxy}-indol-1-yl)-acetic acid ethyl ester

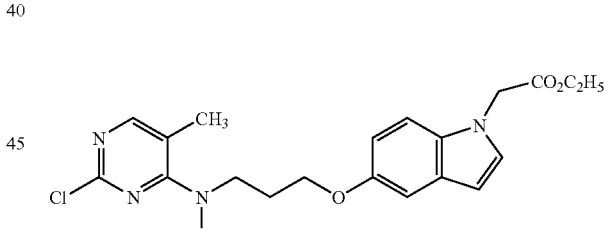

(2-Chloro-5-methyl-pyrimidin-4-yl)-[3-(1H-indol-5-yloxy)-propyl]-methyl-amine (Example 88, 0.117 g, 0.35 mmol) was dissolved in DMF (2 mL) at rt, and sodium hydride was added (0.017 g, 60% in mineral oil, 0.42 mmol). The reaction solution immediately turned purple. The resulting mixture was stirred for 1 h and ethyl bromoacetate (0.065 g, 0.39 mmol) was added. The reaction mixture was stirred for 60 h, diluted with water, and extracted with EtOAc. The organic phases were dried over sodium sulfate, filtered, and concentrated under reduced pressure to give the title compound as an orange oil without purification (103 mg, 70%). LC/MS m/z 417.4 (M+H)$^+$, RT 3.05 min.

77

Step 3: Suzuki Coupling

Example 90

Preparation of [5-(3-{[2-(4-fluoro-phenyl)-5-methyl-pyrimidin-4-yl]-methyl-amino}-propoxy)-indol-1-yl]-acetic acid ethyl ester

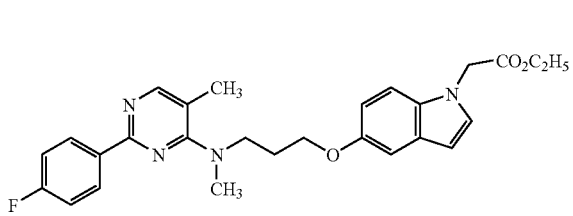

Using the compound from Example 89 as starting material, the title compound was prepared as described in Example 86 to give the title compound (316 mg, 83%). LC/MS m/z 477.3 (M+H)$^+$, RT 3.53 min.

78

Step 4: Hydrolysis

Example 91

Preparation of [5-(3-{[2-(4-fluoro-phenyl)-5-methyl-pyrimidin-4-yl]-methyl-amino}-propoxy)-indol-1-yl]-acetic acid

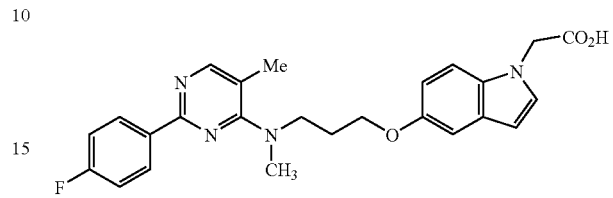

Using the compound from Example 90 as starting material, the title compound was prepared in similar fashion as described in Example 87 (heated at 50° C. for 3 h) to give the title compound as a white solid (316 mg, 83). LC/MS m/z 449.3 (M+H)$^+$, RT 2.26 min.

Method 17: Preparation of Pyrimidine Aminoalkoxy Indoles

Method 17: Preparation of Pyrimidine Aminoalkoxy Indoles

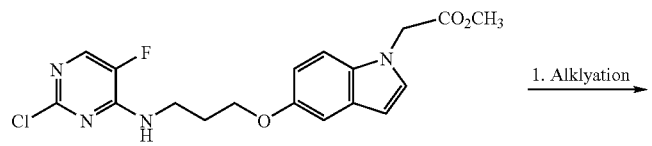

1. Alkylation

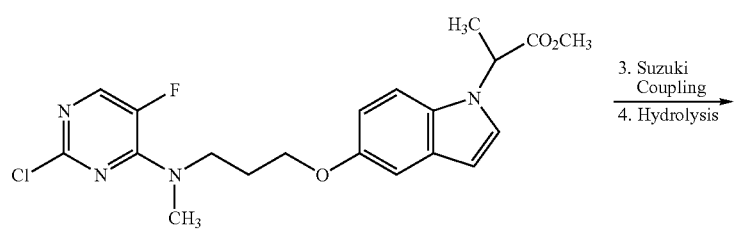

3. Suzuki Coupling
4. Hydrolysis

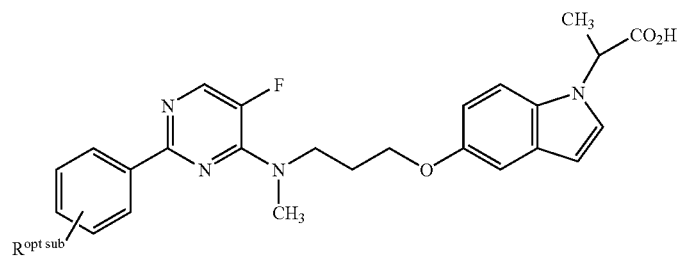

Alkylations on the nitrogen and carbon were performed as shown in Example 92; Suzuki coupling and basic hydrolysis were performed in similar fashion shown in the examples under Method 16.

Step 1: C- and N-Alkylation

Example 92

Preparation of 2-(5-{3-[(2-chloro-5-fluoro-4-pyrimidinyl)(methyl)amino]-propoxy}-indol-1-yl)propanoic acid

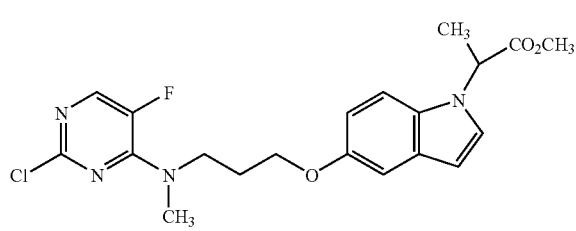

Sodium hydride (0.04 g, 1.78 mmol) was added to a solution of methyl (5-{3-[(2-chloro-5-fluoro-4-pyrimidinyl)amino]propoxy}-1H-indol-1-yl)acetate (0.35 g, 0.89 mmol, prepared in similar fashion as Example 86) in DMF (4.5 mL). After stirring the reaction mixture at rt for 30 minutes, methyl iodide (0.22 mL, 3.56 mmol) was added. The mixture was stirred at rt for additional 18 h, quenched with water, and extracted with ether. The combined ether extracts were washed with water and brine. The organic layer was dried over magnesium sulfate, filtered, and concentrated under vacuum. The desired product (0.11 g, 28%) was obtained after column chromatography (67% hexanes in EtOAc). $^1$H NMR (300 MHz, $CD_2Cl_2$) δ 7.84 (d, 1H), 7.25-7.06 (m, 3H), 6.85-6.82 (m, 1H), 6.47-6.46 (m, 1H), 5.12 (q, 1H), 4.06 (t, 2H) 3.84 (t, 2H), 3.71 (s, 3H), 3.25 (d, 3H), 2.19-2.12 (m, 2H), 1.82 (d, 3H). LC/MS m/z 421.1 (M+H)$^+$, RT 3.35 min.

By substituting the appropriate starting materials, and by using the above described methods other compounds of the invention may be similarly prepared. Example compounds of the invention are summarized below in Table 1.

| Entry No. | Structure | IUPAC Name | M + H (ES) | RT (min) | Methods of Preparation |
|---|---|---|---|---|---|
| 1 | 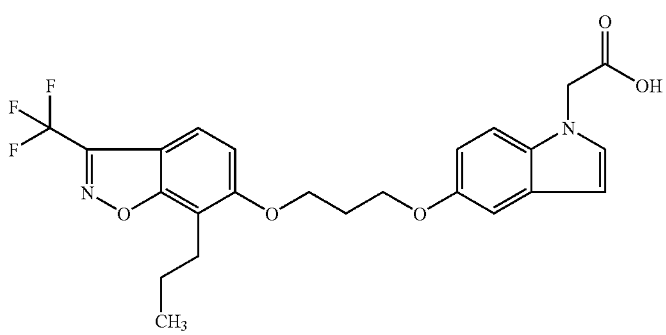 | (5-{3-[3-(1,1-difluoroethyl)-7-propyl-benzo[d]isoxazol-6-yloxy]-propoxy}-indol-1-yl)-acetic acid | 424.3 | 4.09 | 1, 7, 11 |
| 2 | 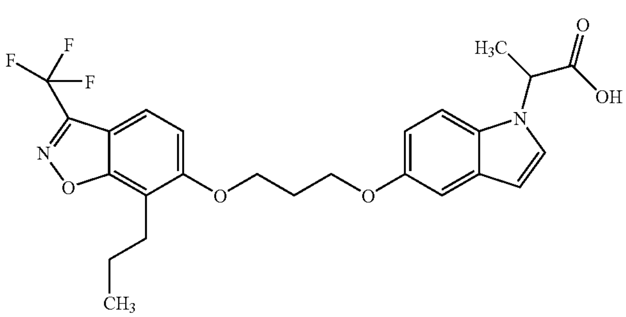 | 2-{5-[3-(7-propyl-3-trifluoromethyl-benzo[d]isoxazol-6-yloxy)-propoxy]-indol-1-yl}-propionic acid | 491.2 | 4.02 | 1, 7, 11 |

-continued

| Entry No. | Structure | IUPAC Name | M + H (ES) | RT (min) | Methods of Preparation |
|---|---|---|---|---|---|
| 3 | 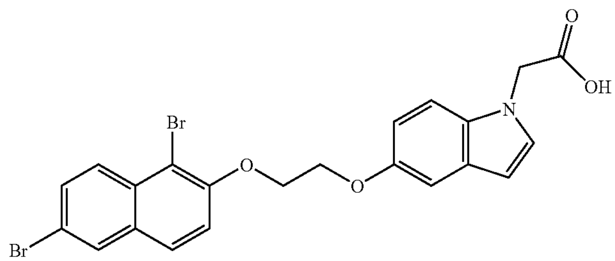 | {5-[2-(1,6-dibromo-naphthalen-2-yloxy)-ethoxy]-indol-1-yl}-acetic acid | 520 | 3.76 | 1, 3 |
| 4 | 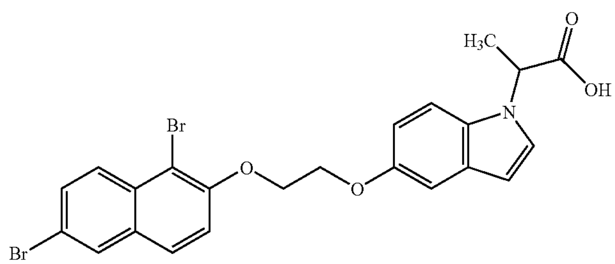 | 2-{5-[2-(1,6-dibromo-naphthalen-2-yloxy)-ethoxy]-indol-1-yl}-propionic acid | 534 | 3.82 | 1, 3 |
| 5 | Chiral | (2S)-2-{5-[2-(1,6-dibromo-naphthalen-2-yloxy)-ethoxy]-indol-1-yl}-propionic acid | 534 | 3.85 | 1, 3 |
| 6 | Chiral | (2R)-2-{5-[2-(1,6-dibromo-naphthalen-2-yloxy)-ethoxy]-indol-1-yl}-propionic acid | 534 | 3.85 | 1, 3 |
| 7 | 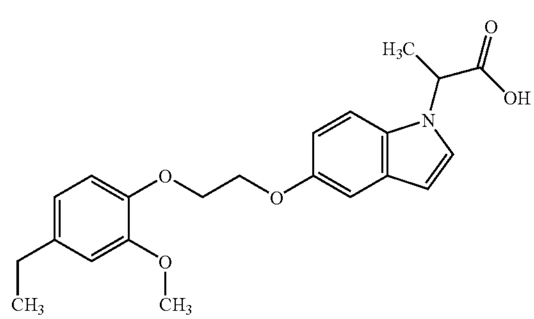 | 2-{5-[2-(4-ethyl-2-methoxy-phenoxy)-ethoxy]-indol-1-yl}-propionic acid | 384 | 3.27 | 1, 3 |

-continued

| Entry No. | Structure | IUPAC Name | M + H (ES) | RT (min) | Methods of Preparation |
|---|---|---|---|---|---|
| 8 | 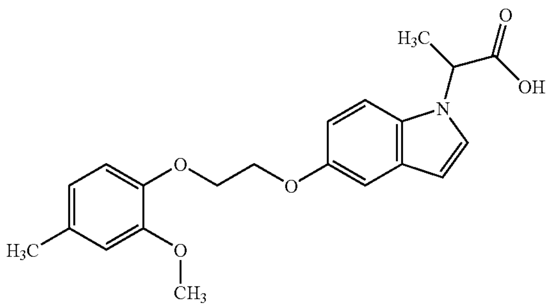 | 2-{5-[2-(2-methoxy-4-methyl-phenoxy)-ethoxy]-indol-1-yl}-propionic acid | 370 | 3.11 | 1, 3 |
| 9 | 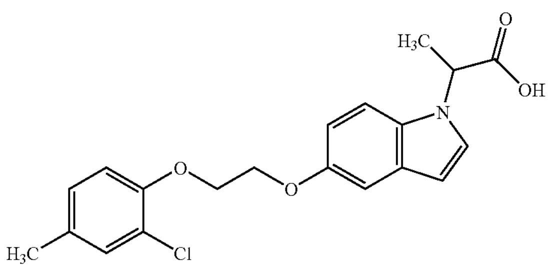 | 2-{5-[2-(2-chloro-4-methyl-phenoxy)-ethoxy]-indol-1-yl}-propionic acid | 74 | 3.37 | 1, 3 |
| 10 | 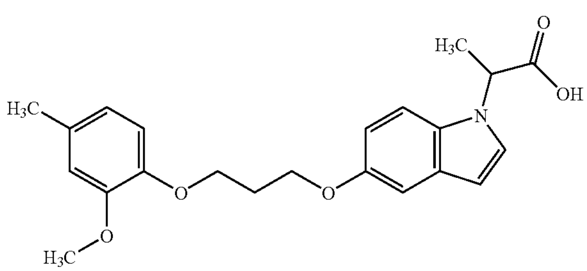 | 2-{5-[3-(2-methoxy-4-methyl-phenoxy)-propoxy]-indol-1-yl}-propionic acid | 384 | 3.22 | 1, 3 |
| 11 | 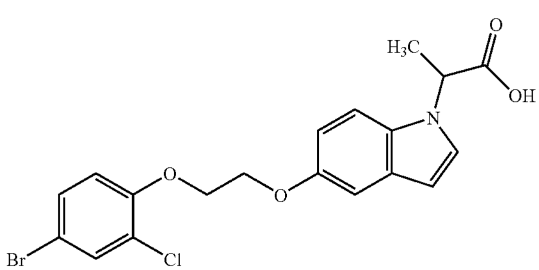 | 2-{5-[2-(4-bromo-2-chloro-phenoxy)-ethoxy]-indol-1-yl}-propionic acid | 439 | 3.54 | 1, 3 |
| 12 | 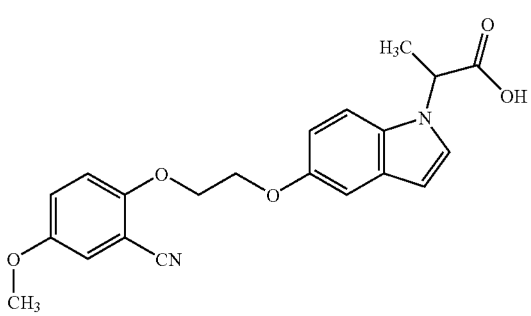 | 2-{5-[2-(2-cyano-4-methoxy-phenoxy)-ethoxy]-indol-1-yl}-propionic acid | 381 | 2.93 | 1, 3 |

-continued

| Entry No. | Structure | IUPAC Name | M + H (ES) | RT (min) | Methods of Preparation |
|---|---|---|---|---|---|
| 13 | 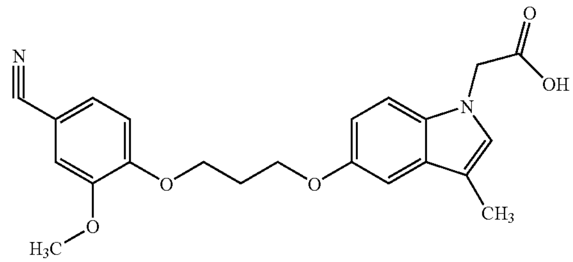 | {5-[3-(4-cyano-2-methoxy-phenoxy)-propoxy]-3-methyl-indol-1-yl}-acetic acid | 395 | 3.45 | 1, 4, 8 |
| 14 | 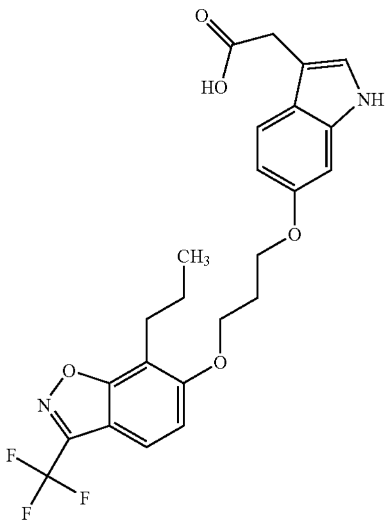 | {6-[3-(7-propyl-3-trifluoromethyl-benzo[d]isoxazol-6-yloxy)-propoxy]-1H-indol-3-yl}-acetic acid | 476.9 | 3.84 | 2, 7, 11 |
| 15 | 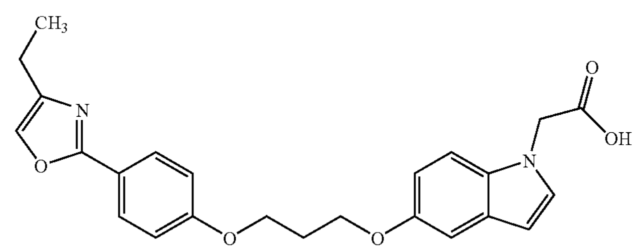 | (5-{3-[4-(4-ethyl-oxazol-2-yl)-phenoxy]-propoxy}-indol-1-yl)-acetic acid | 421.1 | 3.22 | 1, 5, 10 |
| 16 | 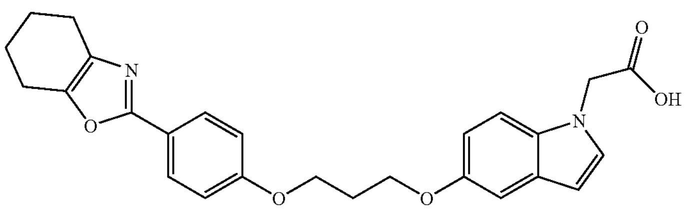 | (5-{3-[4-(4,5,6,7-tetrahydro-benzooxazol-2-yl)-phenoxy]-propoxy}-indol-1-yl)-acetic acid | 447.3 | 3.37 | 1, 5, 10 |
| 17 | 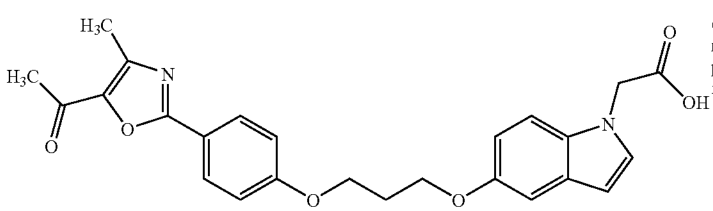 | (5-{3-[4-(5-acetyl-4-methyl-oxazol-2-yl)-phenoxy]-propoxy}-indol-1-yl)-acetic acid | 449.1 | 3.17 | 1, 5, 10 |

| Entry No. | Structure | IUPAC Name | M + H (ES) | RT (min) | Methods of Preparation |
|---|---|---|---|---|---|
| 18 | 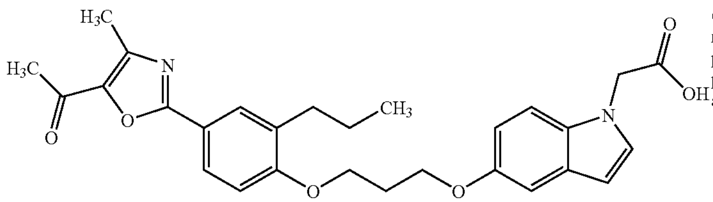 | (5-{3-[4-(5-acetyl-4-methyl-oxazol-2-yl)-2-propyl-phenoxy]-propoxy}-indol-1-yl)-acetic acid | 491.1 | 3.61 | 1, 5, 10 |
| 19 | 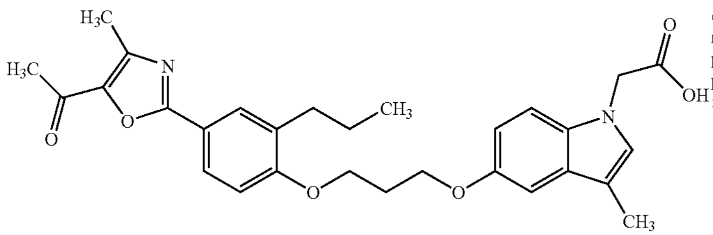 | (5-{3-[4-(5-acetyl-4-methyl-oxazol-2-yl)-2-propyl-phenoxy]-propoxy}-3-methyl-indolyl)-acetic acid | 505.3 | 3.69 | 1, 5, 10 |
| 20 | 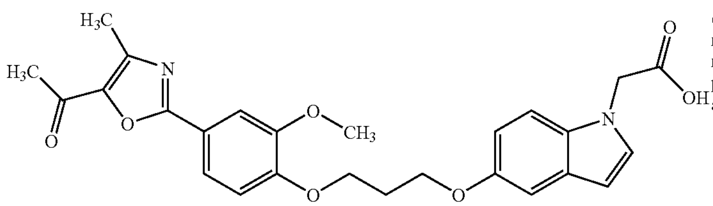 | (5-{3-[4-(5-acetyl-4-methyl-oxazol-2-yl)-2-methoxy-phenoxy]-propoxy}-indol-1-yl)-acetic acid | 479.3 | 2.99 | 1, 5, 10 |
| 21 | 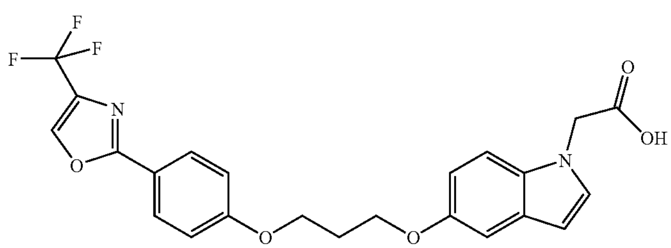 | (5-{3-[4-(4-trifluoro-methyl-oxazol-2-yl)-phenoxy]-propoxy}-indol-1-yl)-acetic acid | 461.1 | 3.52 | 1, 5, 10 |
| 22 | 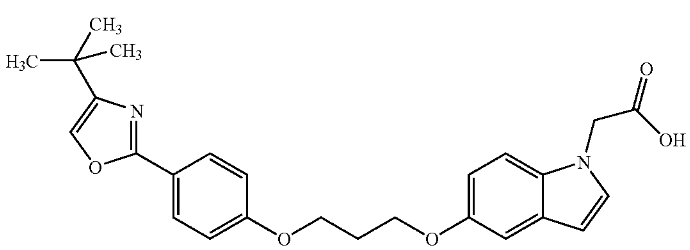 | (5-{3-[4-(4-tert-butyl-oxazol-2-yl)-phenoxy]-propoxy}-indol-1-yl)-acetic acid | | 3.65 | 1, 5, 10 |
| 23 | 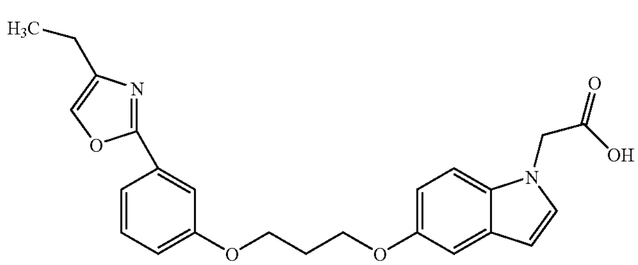 | (5-{3-[3-(4-ethyl-oxazol-2-yl)-phenoxy]-propoxy}-indol-1-yl)-acetic acid | 421.2 | 3.33 | 1, 6, 10 |

-continued

| Entry No. | Structure | IUPAC Name | M + H (ES) | RT (min) | Methods of Preparation |
|---|---|---|---|---|---|
| 24 | 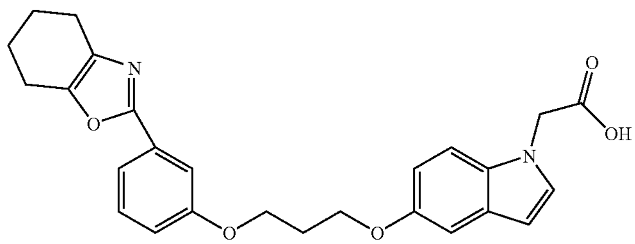 | (5-{3-[3-(4,5,6,7-tetra-hydro-benzooxazol-2-yl)-phenoxy]-propoxy}-indol-1-yl)-acetic acid | 447.2 | 3.47 | 1, 6, 10 |
| 25 | 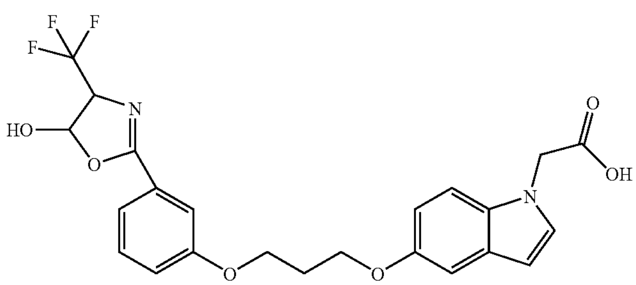 | (5-{3-[3-(5-hydroxy-4-trifluoromethyl-4,5-dihydro-oxazol-2-yl)-phenoxy]-propoxy}-indol-1-yl)-acetic acid | 479.1 | 3.04 | 1, 6, 10 |
| 26 | 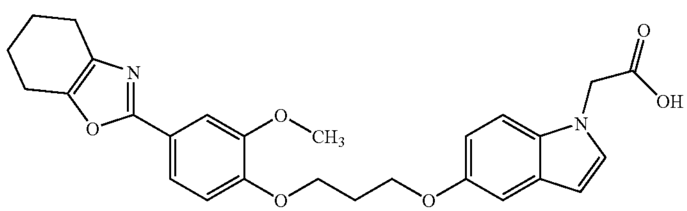 | (5-{3-[2-methoxy-4-(4,5,6,7-tetrahydro-benzooxazol-2-yl)-phenoxy]-propoxy}-indol-1-yl)-acetic acid | 477.2 | 3.34 | 1, 5, 10 |
| 27 | 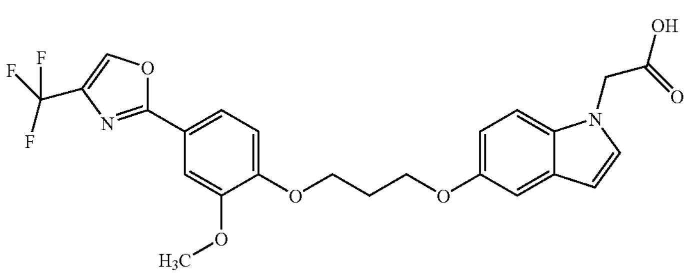 | (5-{3-[2-methoxy-4-(4-trifluoromethyl-oxazol-2-yl)-phenoxy]-propoxy}-indol-1-yl)-acetic acid | 491.1 | 3.37 | 1, 5, 10 |
| 28 | 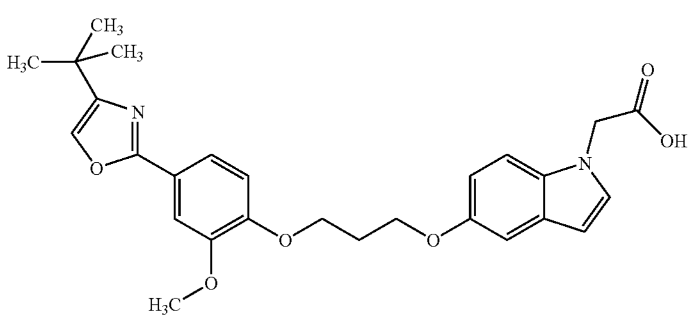 | (5-{3-[4-(4-tert-butyl-oxazol-2-yl)-2-methoxy-phenoxy]-propoxy}-indol-1-yl)-acetic acid | 479.3 | 3.53 | 1, 5, 10 |

| Entry No. | Structure | IUPAC Name | M + H (ES) | RT (min) | Methods of Preparation |
|---|---|---|---|---|---|
| 29 | 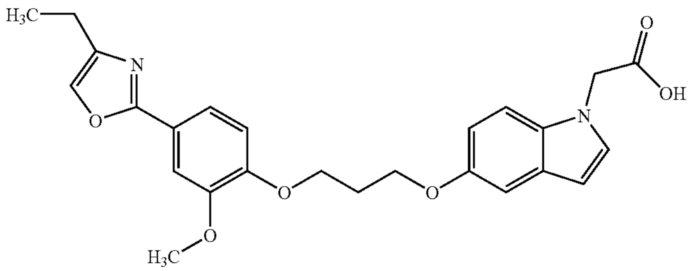 | (5-{3-[4-(4-ethyl-oxazol-2-yl)-2-methoxy-phenoxy]-propoxy}-indol-1-yl)-acetic acid | 451.2 | 3.15 | 1, 5, 10 |
| 30 | 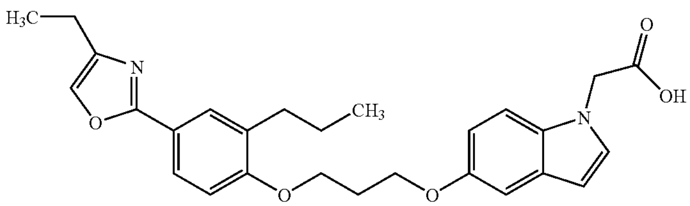 | (5-{3-[4-(4-ethyl-oxazol-2-yl)-2-propyl-phenoxy]-propoxy}-indol-1-yl)-acetic acid | 463.2 | 3.77 | 1, 6, 10 |
| 31 | 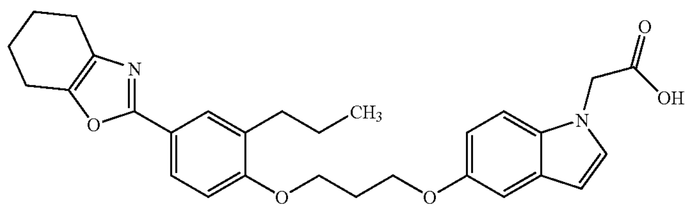 | (5-{3-[2-propyl-4-(4,5,6,7-tetrahydro-benzooxazol-2-yl)-phenoxy]-propoxy}-indol-1-yl)-acetic acid | 489.2 | 3.92 | 1, 6, 10 |
| 32 | 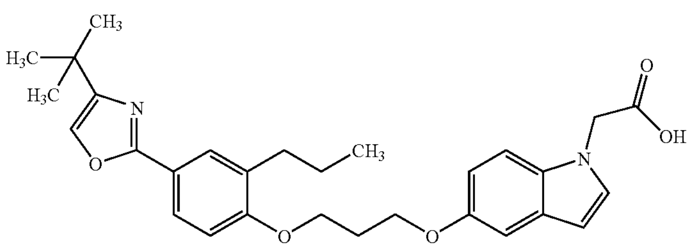 | (5-{3-[4-(4-tert-butyl-oxazol-2-yl)-2-propyl-phenoxy]-propoxy}-indol-1-yl)-acetic acid | 491.2 | 4.19 | 1, 6, 10 |
| 33 | 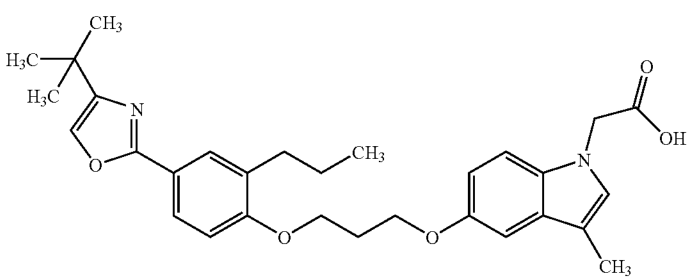 | (5-{3-[4-(4-tert-butyl-oxazol-2-yl)-2-propyl-phenoxy]-propoxy}-3-methylindolyl)-acetic acid | 505.5 | 4.27 | 1, 5, 10 |
| 34 | 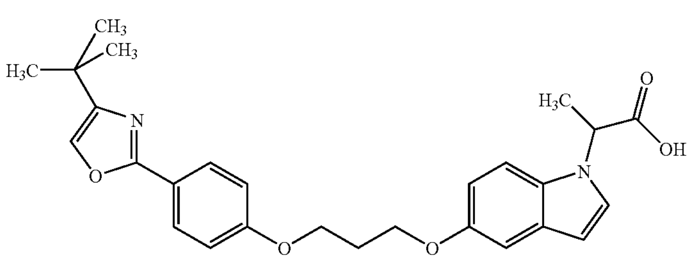 | 2-(5-{3-[4-(4-tert-butyl-oxazol-2-yl)-phenoxy]-propoxy}-indol-1-yl)-propionic acid | 463.2 | 3.87 | 1, 5, 10 |

-continued

| Entry No. | Structure | IUPAC Name | M + H (ES) | RT (min) | Methods of Preparation |
|---|---|---|---|---|---|
| 35 | 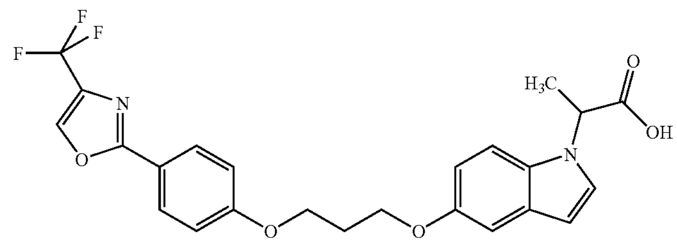 | 2-(5-{3-[4-(4-trifluoro-methyl-oxazol-2-yl)-phenoxy]-propoxy}-indol-1-yl)-propionic acid | 465.1 | 3.64 | 1, 5, 10 |
| 36 | 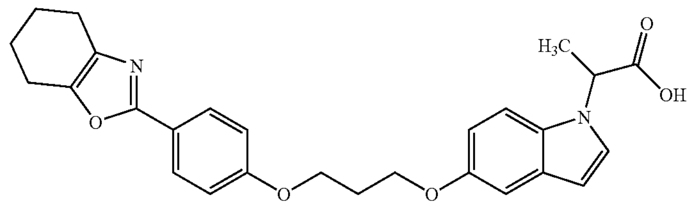 | 2-(5-{3-[4-(4,5,6,7-tetrahydro-benzooxazol-2-yl)-phenoxy]-propoxy}-indol-1-yl)-propionic acid | 461.3 | 3.52 | 1, 5, 10 |
| 37 | 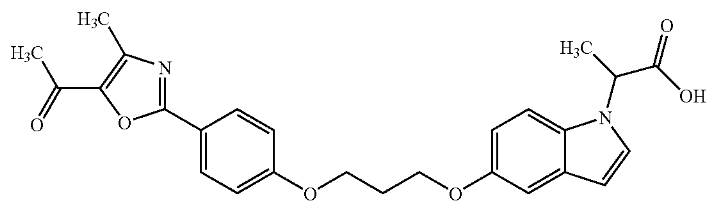 | 2-(5-{3-[4-(5-acetyl-4-methyl-oxazol-2-yl)-phenoxy]-propoxy}-indol-1-yl)-propionic acid | 463.2 | 3.23 | 1, 5, 10 |
| 38 | 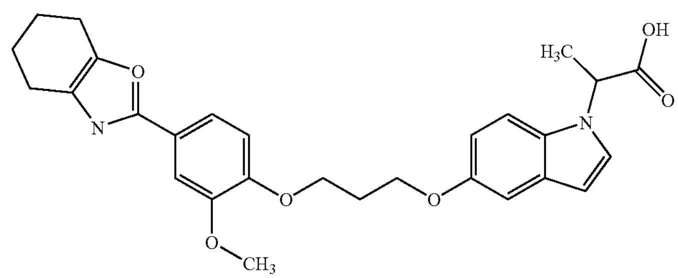 | 2-(5-{3-[2-methoxy-4-(4,5,6,7-tetrahydro-benzooxazol-2-yl)-phenoxy]-propoxy}-indol-1-yl)-propionic acid | 491.4 | 3.39 | 1, 5, 10 |
| 39 | 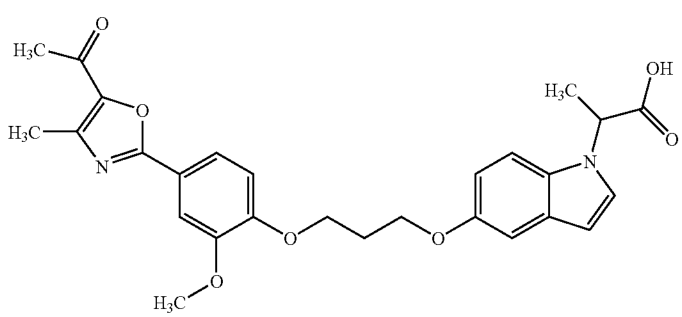 | 2-(5-{3-[4-(5-acetyl-4-methyl(1,3-oxazol-2-yl))-2-methoxyphenoxy]propoxy}indolyl)propanoic acid | 493.3 | 3.13 | 1, 5, 10 |
| 40 | 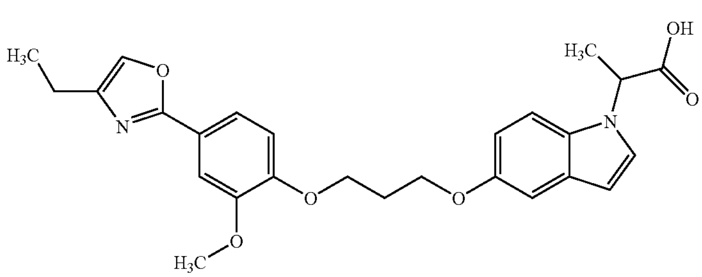 | 2-(5-{3-[4-(4-ethyl(1,3-oxazol-2-yl))-2-methoxyphenoxy]propoxy}indolyl)propanoic acid | 465.1 | 3.25 | 1, 5, 10 |

| Entry No. | Structure | IUPAC Name | M + H (ES) | RT (min) | Methods of Preparation |
|---|---|---|---|---|---|
| 41 | 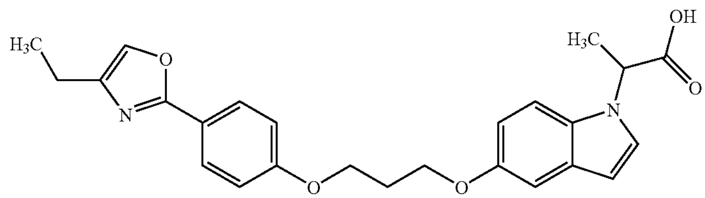 | 2-(5-{3-[4-(4-ethyl(1,3-oxazol-2-yl))-phenoxy]propoxy}indolyl)propanoic acid | 435.1 | 3.46 | 1, 5, 10 |
| 42 | 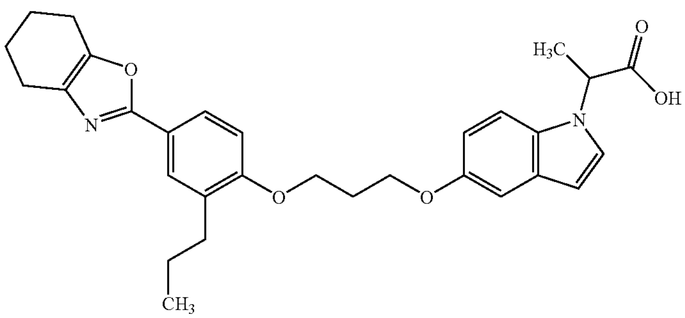 | 2-{5-[3-(2-propyl-4-(4,5,6,7-tetrahydrobenzoxazol-2-yl)phenoxy)propoxy]indolyl}propanoic acid | 503.5 | 3.99 | 1, 5, 10 |
| 43 | 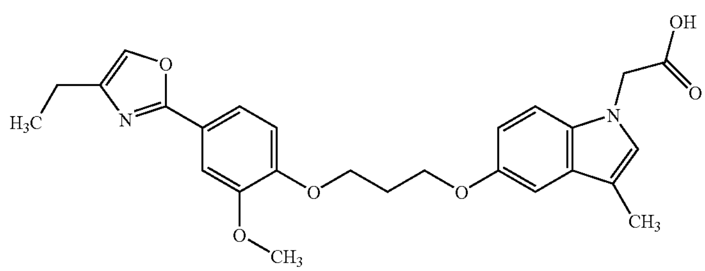 | 2-(5-{3-[4-(4-ethyl(1,3-oxazol-2-yl))-2-methoxyphenoxy]propoxy}-3-methylindolyl)acetic acid | 465.1 | 3.27 | 1, 5, 10 |
| 44 | 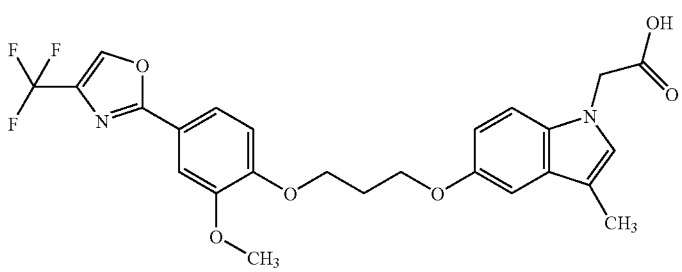 | 2-[5-(3-{2-methoxy-4-[4-(trifluoromethyl)(1,3-oxazol-2-yl)]phenoxy}propoxy)-3-methylindolyl]acetic acid | 505 | 3.51 | 1, 5, 10 |
| 45 | 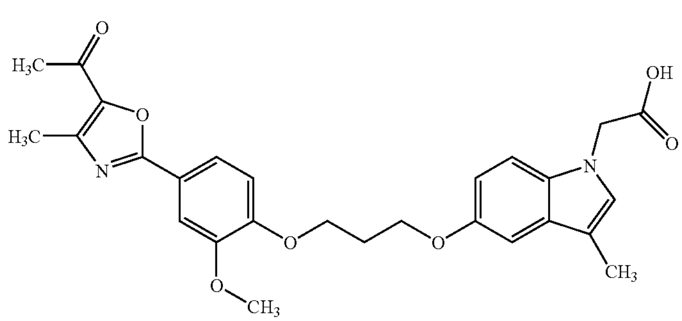 | 2-(5-{3-[4-(5-acetyl-4-methyl(1,3-oxazol-2-yl))-2-methoxyphenoxy]propoxy}-3-methylindolyl)acetic acid | 493.2 | 3.14 | 1, 5, 10 |

-continued

| Entry No. | Structure | IUPAC Name | M + H (ES) | RT (min) | Methods of Preparation |
|---|---|---|---|---|---|
| 46 | 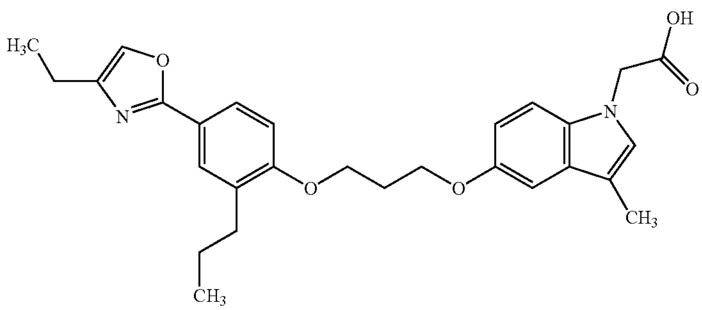 | 2-(5-{3-[4-(4-ethyl(1,3-oxazol-2-yl))-2-propyl-phenoxy]propoxy}-3-methylindolyl)acetic acid | 477.4 | 3.88 | 1, 5, 10 |
| 47 | 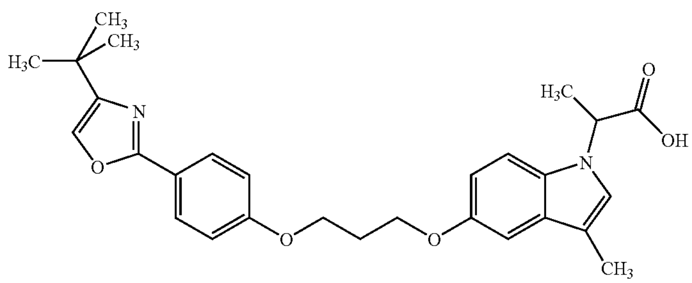 | 2-[5-(3-{4-[4-(tert-butyl)(1,3-oxazol-2-yl)]phenoxy}propoxy)-3-methylindolyl]propanoic acid | 477.2 | 4 | 1, 5, 10 |
| 48 | 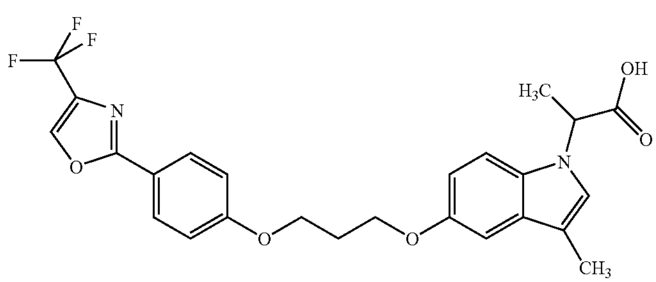 | 2-[3-methyl-5-(3-{4-[4-(trifluoromethyl)(1,3-oxazol-2-yl)]phenoxy}propoxy)indolyl]propanoic acid | 489.1 | 3.76 | 1, 5, 10 |
| 49 | 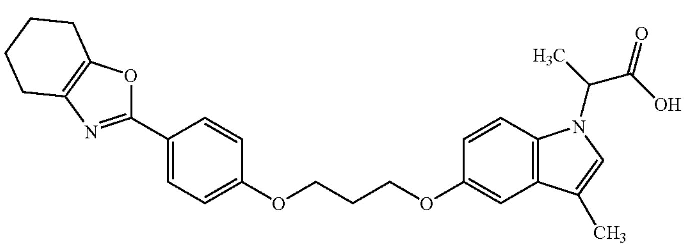 | 2-{3-methyl-5-[3-(4-(4,5,6,7-tetrahydro-benzoxazol-2-yl)phenoxy)propoxy]indolyl}propanoic acid | 475.3 | 3.7 | 1, 5, 10 |
| 50 | 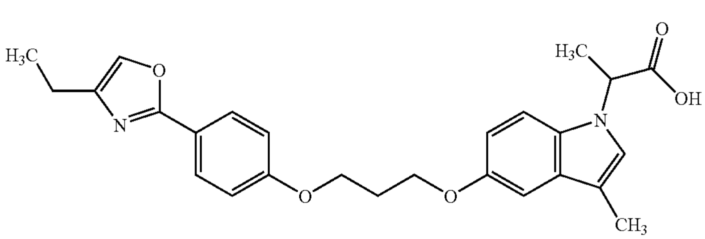 | 2-(5-{3-[4-(4-ethyl(1,3-oxazol-2-yl))phenoxy]propoxy}-3-methyl-indolyl)propanoic acid | 449.3 | 3.57 | 1, 5, 10 |

-continued

| Entry No. | Structure | IUPAC Name | M + H (ES) | RT (min) | Methods of Preparation |
|---|---|---|---|---|---|
| 51 | 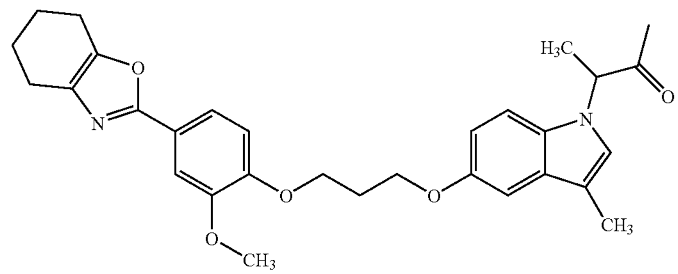 | 2-{5-[3-(2-methoxy-4-(4,5,6,7-tetrahydro-benzoxazol-2-yl)phenoxy)propoxy]-3-methylindolyl}propanoic acid | 505.4 | 3.53 | 1, 5, 10 |
| 52 | 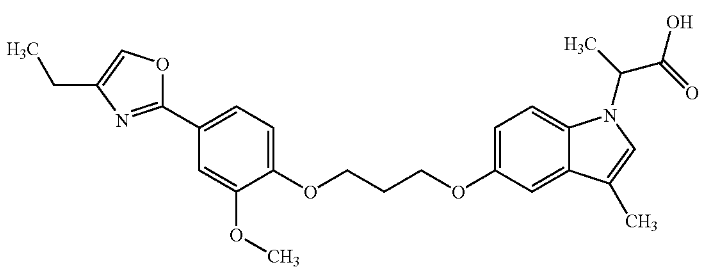 | 2-(5-{3-[4-(4-ethyl(1,3-oxazol-2-yl))-2-methoxy-phenoxy]propoxy}-3-methylindolyl)propanoic acid | 479.1 | 3.41 | 1, 5, 10 |
| 53 | 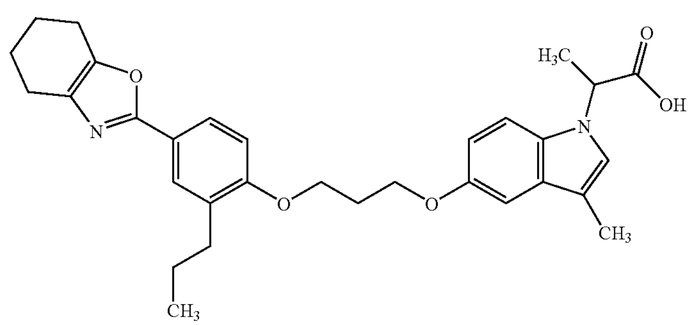 | 2-{3-methyl-5-[3-(2-propyl-4-(4,5,6,7-tetrahydrobenzoxazol-2-yl)phenoxy)propoxy]indolyl}propanoic acid | 517.5 | 4.11 | 1, 5, 10 |
| 54 | 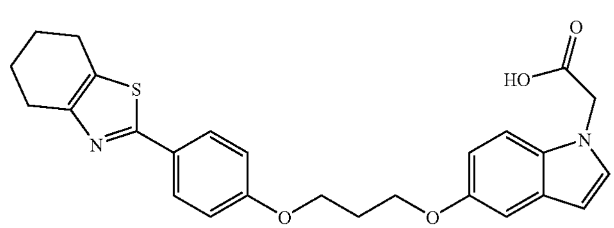 | 2-{5-[3-(4-(4,5,6,7-tetrahydrobenzothiazol-2-yl)phenoxy)propoxy]indolyl}acetic acid | 463.1 | 3.5 | 1, 4, 9 |
| 55 | 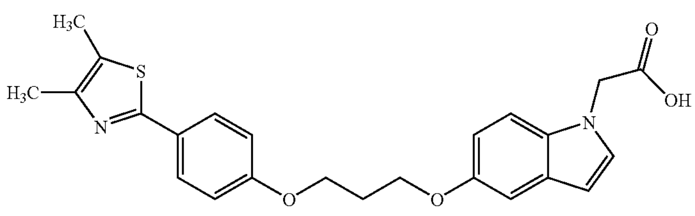 | 2-(5-{3-[4-(4,5-dimethyl-1,3-thiazol-2-yl)phenoxy]propoxy}indolyl)acetic acid | 437.1 | 3.21 | 1, 4, 9 |

-continued

| Entry No. | Structure | IUPAC Name | M + H (ES) | RT (min) | Methods of Preparation |
|---|---|---|---|---|---|
| 56 | 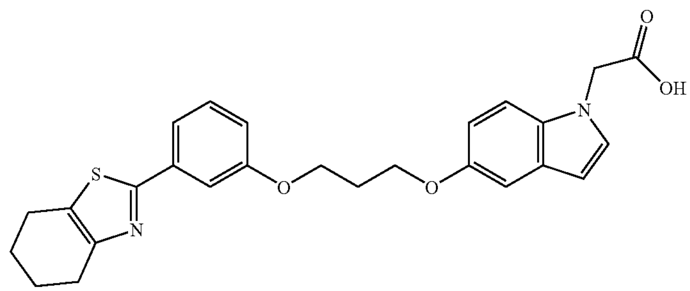 | (5-{3-[3-(4,5,6,7-tetrahydro-benzothiazol-2-yl)-phenoxy]-propoxy}-indol-1-yl)-acetic acid | 463.2 | 3.6 | 1, 4, 9 |
| 57 | 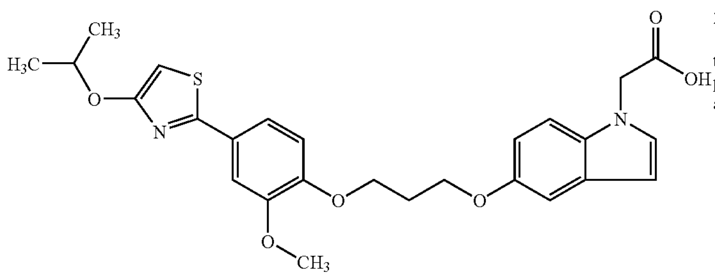 | 2-[5-(3-{2-methoxy-4-[4-(methylethoxy)(1,3-thiazol-2-yl)]phenoxy}propoxy)indolyl]acetic acid | 497.1 | 3.42 | 1, 4, 9 |
| 58 | 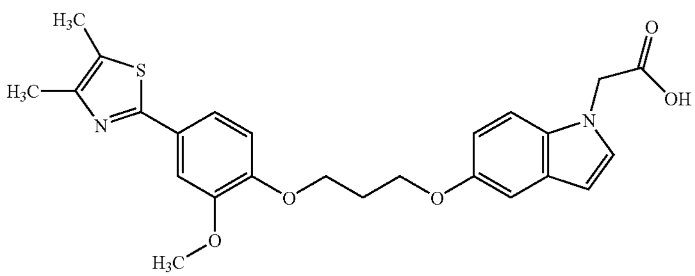 | 2-(5-{3-[4-(4,5-dimethyl(1,3-thiazol-2-yl))-2-methoxyphenoxy]propoxy}indolyl)acetic acid | 467.3 | 3.04 | 1, 4, 9 |
| 59 | 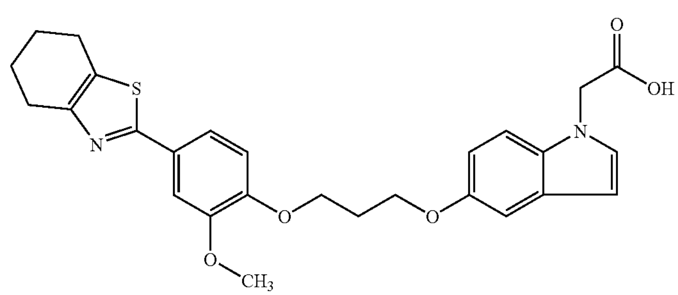 | 2-{5-[3-(2-methoxy-4-(4,5,6,7-tetrahydro-benzothiazol-2-yl)phenoxy)propoxy]indolyl}acetic acid | 493.2 | 3.37 | 1, 4, 9 |
| 60 | 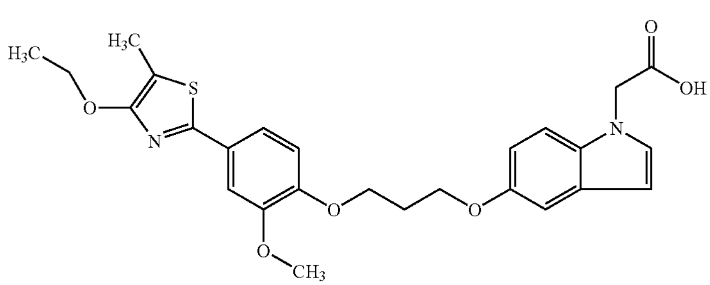 | 2-(5-{3-[4-(4-ethoxy-5-methyl(1,3-thiazol-2-yl))-2-methoxyphenoxy]propoxy}indolyl)acetic acid | 497.1 | 3.72 | 1, 4, 9 |

-continued

| Entry No. | Structure | IUPAC Name | M + H (ES) | RT (min) | Methods of Preparation |
|---|---|---|---|---|---|
| 61 | 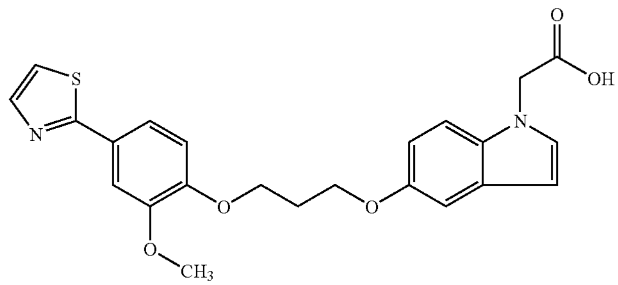 | 2-{5-[3-(2-methoxy-4-(1,3-thiazol-2-yl)phenoxy)propoxy]indolyl}acetic acid | 439.1 | 3.01 | 1, 4, 9 |
| 62 | 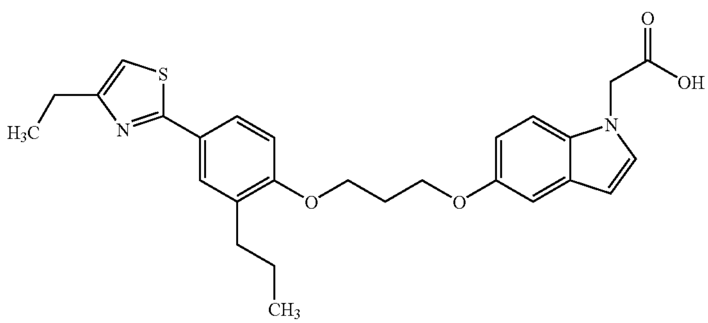 | (5-{3-[4-(4-ethyl-thiazol-2-yl)-2-propyl-phenoxy]-propoxy}-indol-1-yl)-acetic acid | 479.1 | 3.83 | 1, 4, 8 |
| 63 | 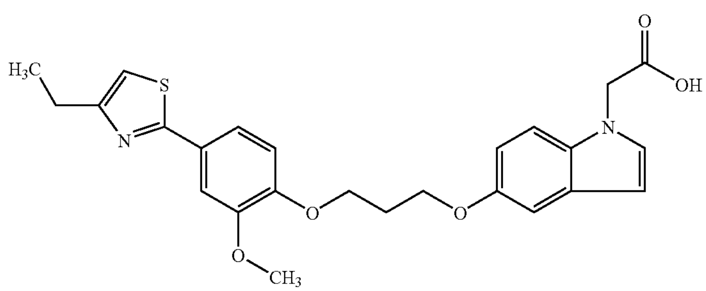 | (5-{3-[4-(4-ethyl-thiazol-2-yl)-2-methoxy-phenoxy]-propoxy}-indol-1-yl)-acetic acid | 467.1 | 3.3 | 1, 4, 8 |
| 64 | 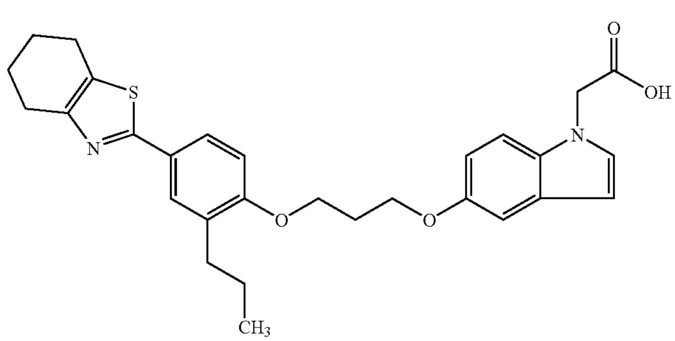 | 2-{5-[3-(2-propyl-4-(4,5,6,7-tetrahydro-benzothiazol-2-yl)phenoxy)propoxy]indolyl}acetic acid | 505.4 | 3.88 | 1, 4, 9 |

-continued

| Entry No. | Structure | IUPAC Name | M + H (ES) | RT (min) | Methods of Preparation |
|---|---|---|---|---|---|
| 65 | 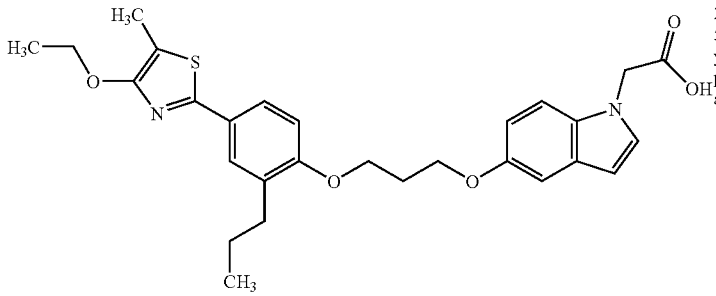 | 2-(5-{3-[4-(4-ethoxy-5-methyl(1,3-thiazol-2-yl))-2-propylphenoxy]propoxy}indolyl)acetic acid | 509.4 | 4.31 | 1, 4, 9 |
| 66 | 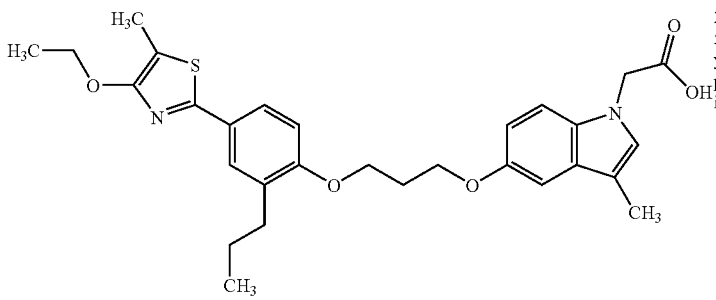 | 2-(5-{3-[4-(4-ethoxy-5-methyl(1,3-thiazol-2-yl))-2-propylphenoxy]propoxy}-3-methylindolyl)acetic acid | 523.2 | 4.42 | 1, 4, 9 |
| 67 | 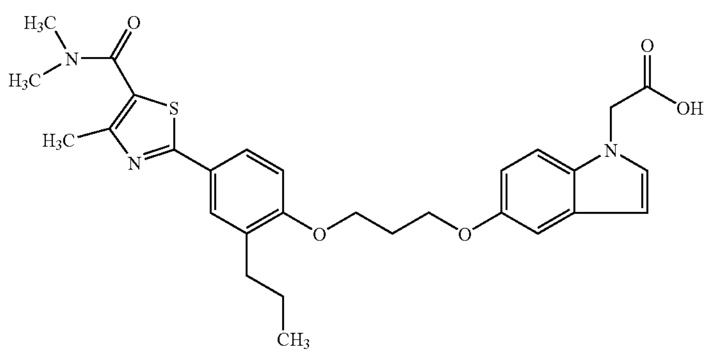 | 2-[5-(3-{4-[5-(N,N-dimethylcarbamoyl)-4-methyl(1,3-thiazol-2-yl)]-2-propylphenoxy}propoxy)indolyl]acetic acid | 536.1 | 3.36 | 1, 4, 8 |
| 68 | 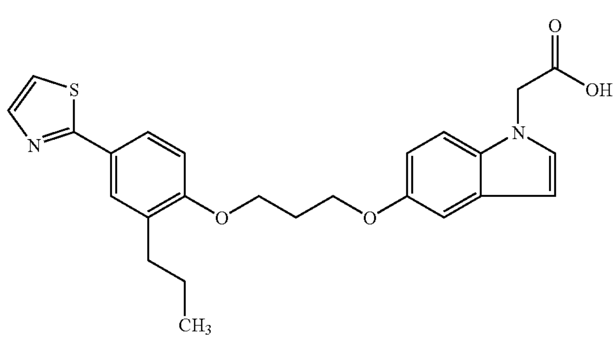 | 2-{5-[3-(2-propyl-4-(1,3-thiazol-2-yl)phenoxy)propoxy]indolyl}acetic acid | 451.3 | 3.57 | 1, 4, 9 |

-continued

| Entry No. | Structure | IUPAC Name | M + H (ES) | RT (min) | Methods of Preparation |
|---|---|---|---|---|---|
| 69 | 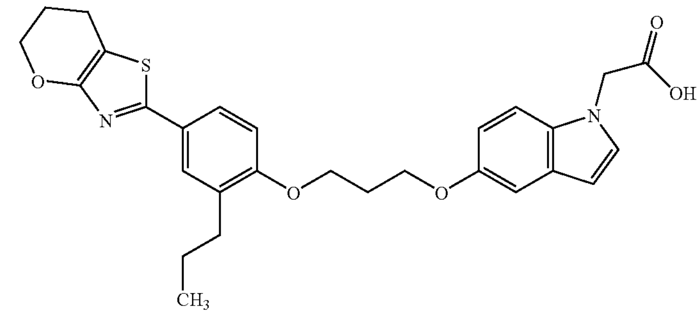 | (5-{3-[4-(6,7-dihydro-5H-pyrano[2,3-d]thiazol-2-yl)-2-propyl-phenoxy]-propoxy}-indol-1-yl)-acetic acid | 507.4 | 3.8 | 1, 4, 9 |
| 70 | 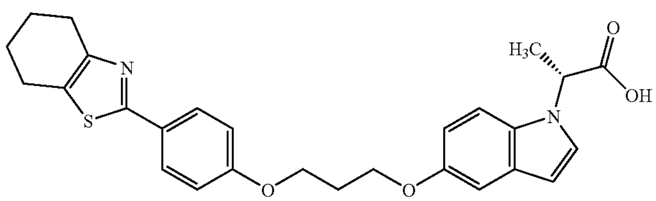 | Chiral 2-(5-{3-[4-(4,5,6,7-tetrahydro-benzothiazol-2-yl)-phenoxy]-propoxy}-indol-1-yl)-propionic acid | 477.2 | 3.52 | 1, 4, 9 |
| 71 | 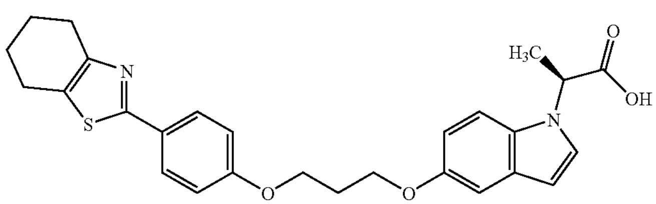 | Chiral 2-(5-{3-[4-(4,5,6,7-tetrahydro-benzothiazol-2-yl)-phenoxy]-propoxy}-indol-1-yl)-propionic acid | 477.2 | 3.52 | 1, 4, 9 |
| 72 | 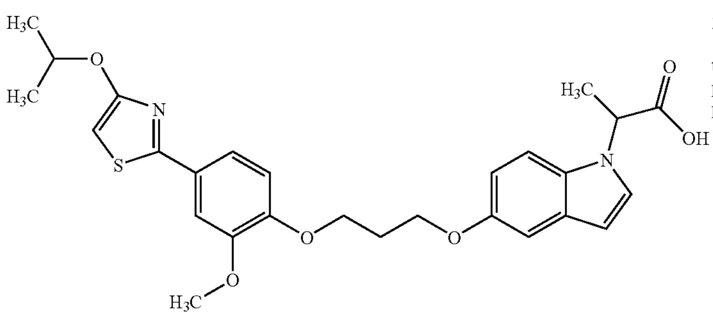 | 2-[5-(3-{2-methoxy-4-[4-(methylethoxy)(1,3-thiazol-2-yl)]phenoxy}propoxy)indolyl]propanoic acid | 511.3 | 3.56 | 1, 4, 9 |
| 73 | 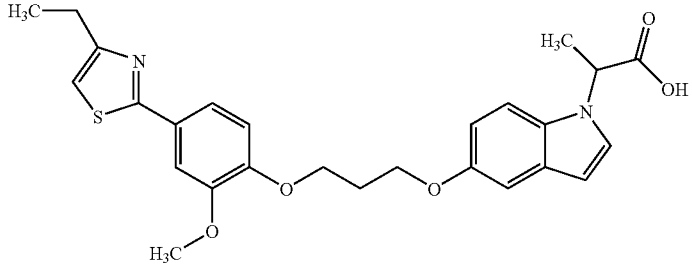 | 2-(5-{3-[4-(4-ethyl(1,3-thiazol-2-yl))-2-methoxy-phenoxy]propoxy}indolyl)propanoic acid | 481.3 | 3.36 | 1, 4, 9 |

-continued

| Entry No. | Structure | IUPAC Name | M + H (ES) | RT (min) | Methods of Preparation |
|---|---|---|---|---|---|
| 74 | 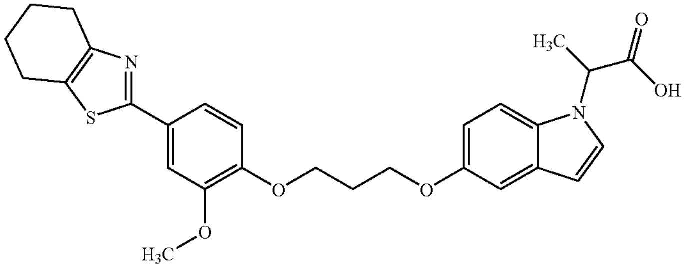 | 2-{5-[3-(2-methoxy-4-(4,5,6,7-tetrahydro-benzothiazol-2-yl)phenoxy)propoxy]indolyl}propanoic acid | 507.1 | 3.48 | 1, 4, 9 |
| 75 | 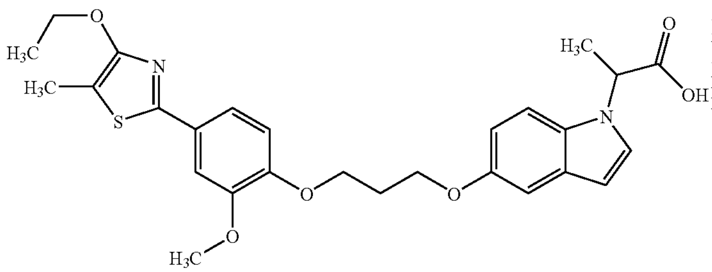 | 2-(5-{3-[4-(4-ethoxy-5-methyl(1,3-thiazol-2-yl))-2-methoxyphenoxy]propoxy}indolyl)propanoic acid | 511.1 | 3.83 | 1, 4, 9 |
| 76 | 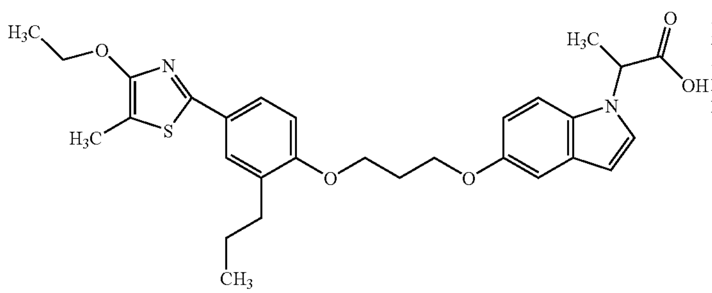 | 2-(5-{3-[4-(4-ethoxy-5-methyl(1,3-thiazol-2-yl))-2-propylphenoxy]propoxy}indolyl)propanoic acid | 523.1 | 4.46 | 1, 4, 9 |
| 77 | 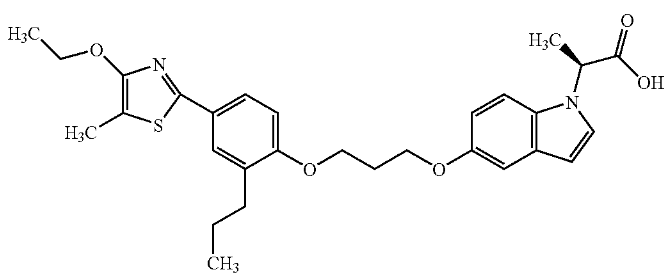 | Chiral (2S)-2-(5-{3-[4-(4-ethoxy-5-methyl-thiazol-2-yl)-2-propyl-phenoxy]-propoxy}-indol-1-yl)-propionic acid | 523.3 | 4.47 | 1, 4, 9 |
| 78 | 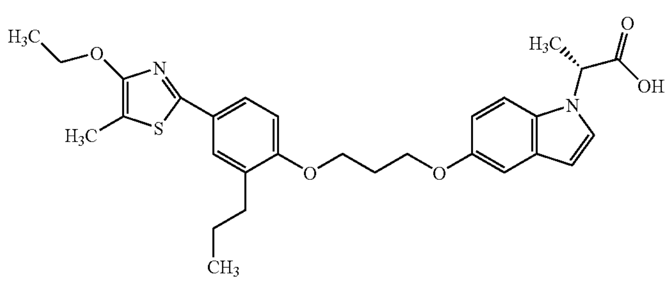 | Chiral (2R)-2-(5-{3-[4-(4-ethoxy-5-methyl-thiazol-2-yl)-2-propyl-phenoxy]-propoxy}-indol-1-yl)-propionic acid | 523.3 | 4.47 | 1, 4, 9 |

-continued

| Entry No. | Structure | IUPAC Name | M + H (ES) | RT (min) | Methods of Preparation |
|---|---|---|---|---|---|
| 79 | 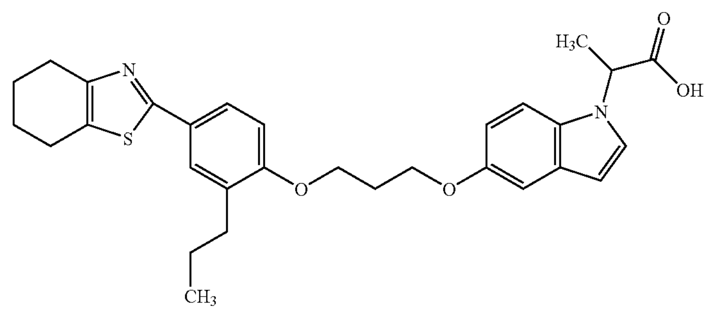 | 2-{5-[3-(2-propyl-4-(4,5,6,7-tetrahydro-benzothiazol-2-yl)phenoxy)propoxy]indolyl}propanoic acid | 519.2 | 3.99 | 1, 4, 9 |
| 80 | 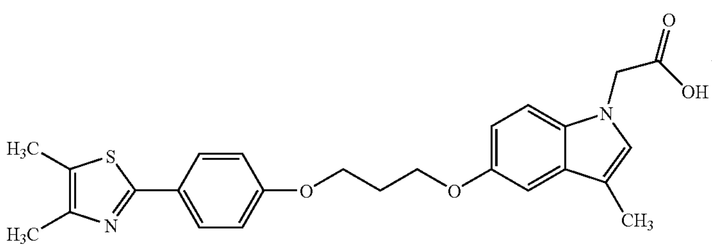 | 2-(5-{3-[4-(4,5-dimethyl(1,3-thiazol-2-yl))phenoxy]propoxy}-3-methylindolyl)acetic acid | 451 | 3.34 | 1, 4, 9 |
| 81 | 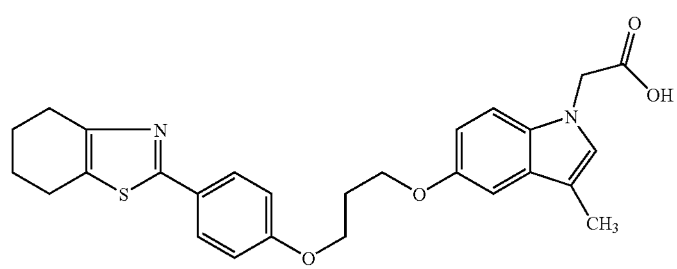 | (3-methyl-5-{3-[4-(4,5,6,7-tetrahydro-benzothiazol-2-yl)-phenoxy]-propoxy}-indol-1-yl)-acetic acid | 477 | 3.63 | 1, 4, 9 |
| 82 | 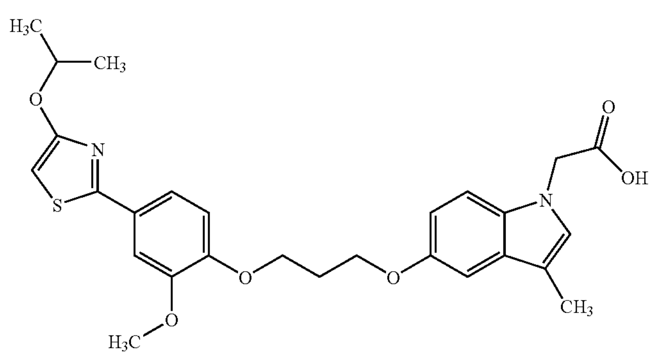 | 2-[5-(3-{2-methoxy-4-[4-(methylethoxy)(1,3-thiazol-2-yl)]phenoxy}propoxy)-3-methyl-indolyl]acetic acid | 511 | 3.57 | 1, 4, 9 |
| 83 | 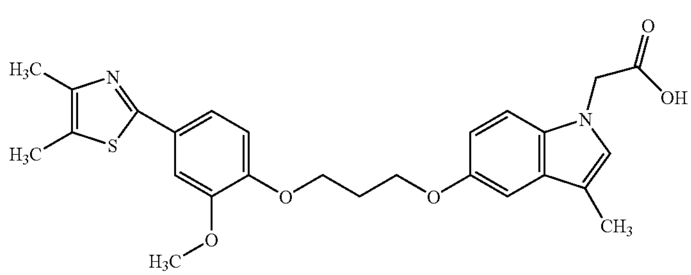 | 2-(5-{3-[4-(4,5-dimethyl(1,3-thiazol-2-yl))-3-methoxyphenoxy]propoxy}-3-methyl-indolyl)acetic acid | 481.1 | 3.21 | 1, 4, 9 |

-continued

| Entry No. | Structure | IUPAC Name | M + H (ES) | RT (min) | Methods of Preparation |
|---|---|---|---|---|---|
| 84 | 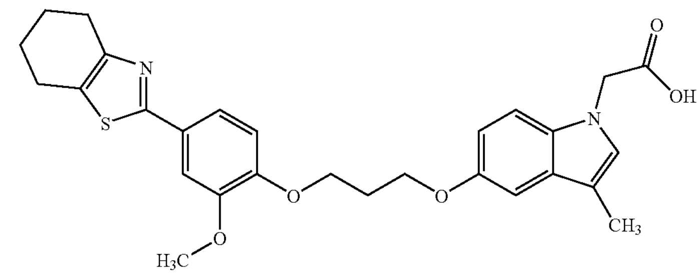 | 2-{5-[3-(2-methoxy-4-(4,5,6,7-tetrahydro-benzothiazol-2-yl)phenoxy)propoxy]-3-methylindolyl}acetic acid | 507.1 | 3.47 | 1, 4, 9 |
| 85 | 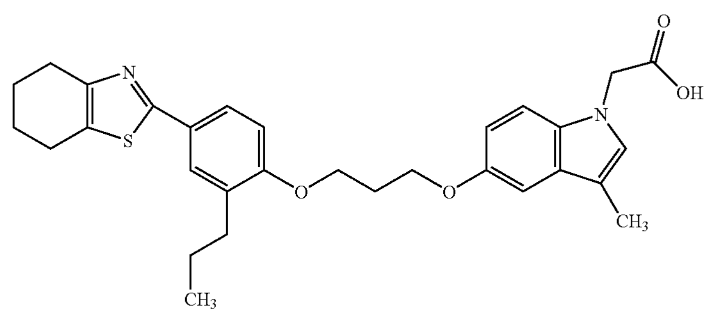 | 2-{3-methyl-5-[3-(2-propyl-4-(4,5,6,7-tetrahydrobenzothiazol-2-yl)phenoxy)propoxy]indolyl}acetic acid | 519.2 | 3.99 | 1, 4, 9 |
| 86 | 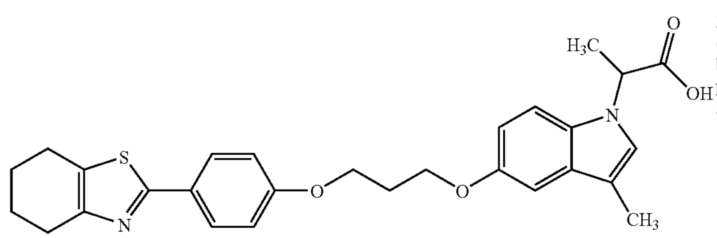 | 2-{3-methyl-5-[3-(4-(4,5,6,7-tetrahydro-benzothiazol-2-yl)phenoxy)propoxy]indolyl}propanoic acid | 491 | 3.76 | 1, 4, 9 |
| 87 | 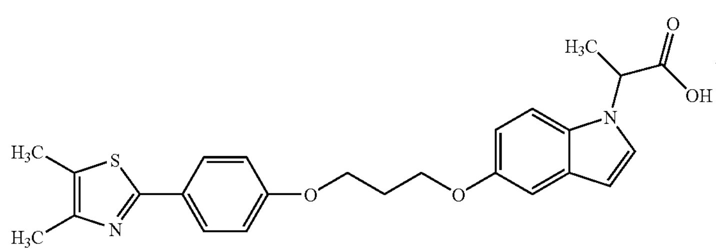 | 2-(5-{3-[4-(4,5-dimethyl(1,3-thiazol-2-yl))phenoxy]propoxy}-indol-1-yl)propanoic acid | 481.2 | 3.71 | 1, 4, 9 |
| 88 | 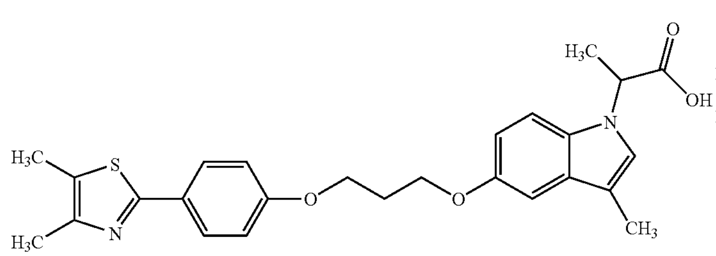 | 2-(5-{3-[4-(4,5-dimethyl(1,3-thiazol-2-yl))phenoxy]propoxy}-3-methylindolyl)propanoic acid | 465 | 3.46 | 1, 4, 9 |

-continued

| Entry No. | Structure | IUPAC Name | M + H (ES) | RT (min) | Methods of Preparation |
|---|---|---|---|---|---|
| 89 | 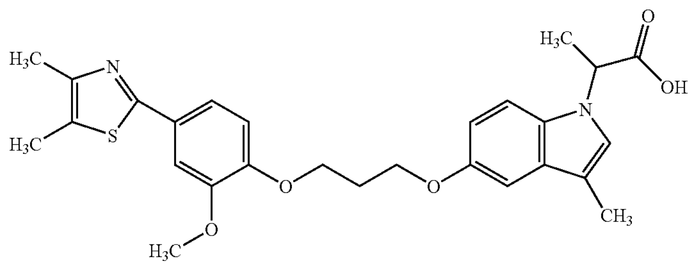 | 2-(5-{3-[4-(4,5-dimethyl (1,3-thiazol-2-yl))-2-methoxyphenoxy] propoxy}-3-methyl-indolyl)propanoic acid | 495.1 | 3.33 | 1, 4, 9 |
| 90 | 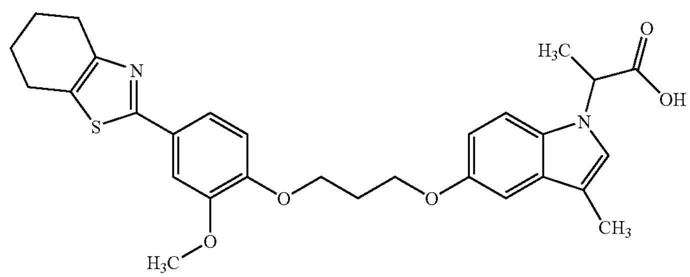 | 2-{5-[3-(2-methoxy-4-(4,5,6,7-tetrahydro-benzothiazol-2-yl) phenoxy)propoxy]-3-methylindolyl}propanoic acid | 521.2 | 3.59 | 1, 4, 9 |
| 91 | 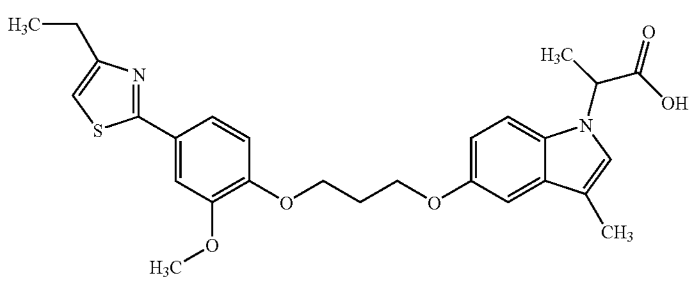 | 2-(5-{3-[4-(4-ethyl (1,3-thiazol-2-yl))-2-methoxyphenoxy] propoxy}-3-methyl-indolyl)propanoic acid | 495.1 | 3.53 | 1, 4, 9 |
| 92 | 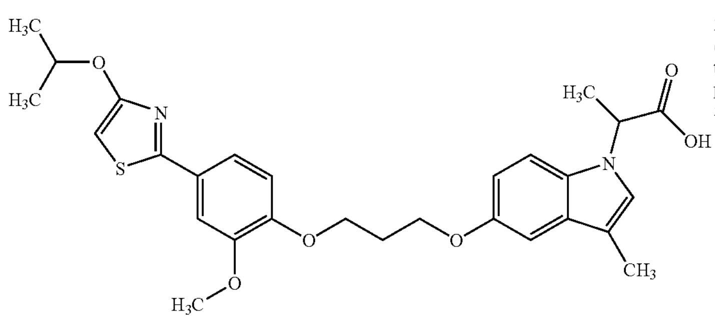 | 2-[5-(3-{2-methoxy-4-[4-(methylethoxy)(1,3-thiazol-2-yl)]phenoxy} propoxy)-3-methyl-indolyl]propanoic acid | 525.1 | 3.73 | 1, 4, 9 |
| 93 | 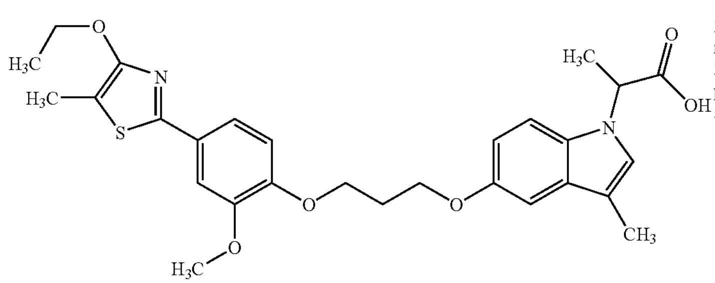 | 2-(5-{3-[4-(4-ethoxy-5-methyl(1,3-thiazol-2-yl))-2-methoxyphenoxy] propoxy}-3-methyl-indolyl)propanoic acid | 525.1 | 3.98 | 1, 4, 9 |

-continued

| Entry No. | Structure | IUPAC Name | M + H (ES) | RT (min) | Methods of Preparation |
|---|---|---|---|---|---|
| 94 | 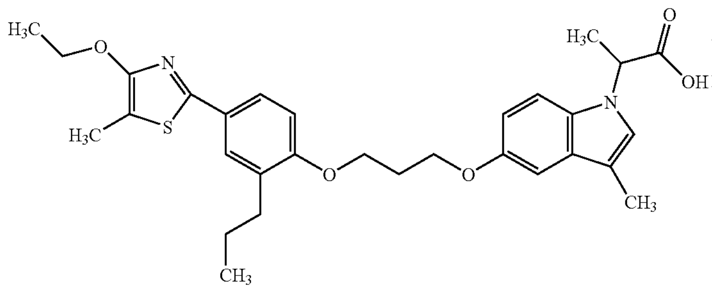 | 2-(5-{3-[4-(4-ethoxy-5-methyl(1,3-thiazol-2-yl))-2-propylphenoxy]propoxy}-3-methyl-indolyl)propanoic acid | 537.4 | 4.6 | 1, 4, 9 |
| 95 | 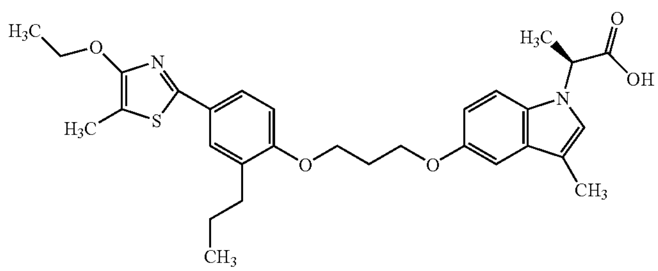 | Chiral (2S)-2-(5-{3-[4-(4-ethoxy-5-methyl-thiazol-2-yl)-2-propyl-phenoxy]-propoxy}-3-methyl-indol-1-yl)propionic acid | 537.3 | 4.6 | 1, 4, 9 |
| 96 | 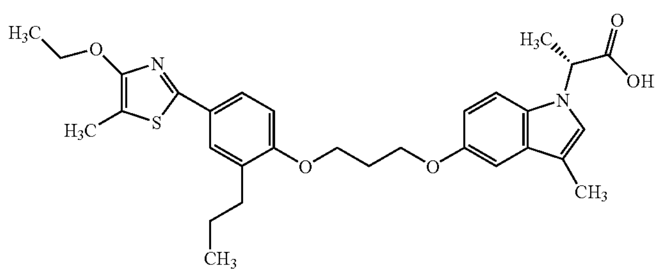 | Chiral (2R)-2-(5-{3-[4-(4-ethoxy-5-methyl-thiazol-2-yl)-2-propyl-phenoxy]-propoxy}-3-methyl-indol-1-yl)propionic acid | 537.3 | 4.6 | 1, 4, 9 |
| 97 | 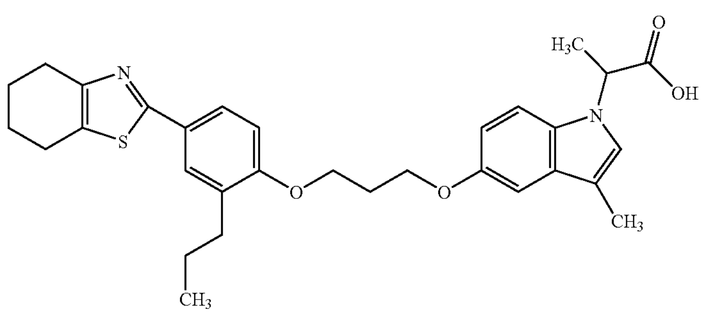 | 2-{3-methyl-5-[3-(2-propyl-4-(4,5,6,7-tetrahydrobenzothiazol-2-yl)phenoxy)propoxy]indolyl}propanoic acid | 533.2 | 4.13 | 1, 4, 9 |
| 98 | 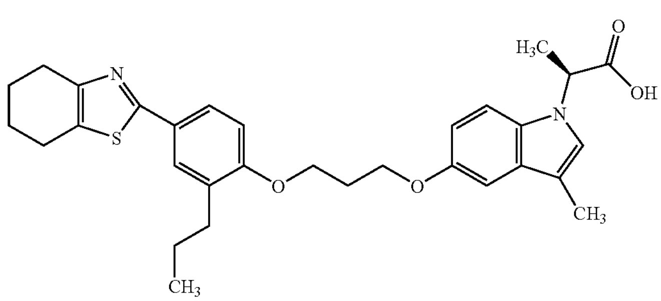 | Chiral (2S)-2-(3-methyl-5-{3-[2-propyl-4-(4,5,6,7-tetrahydro-benzothiazol-2-yl)-phenoxy]-propoxy}-indol-1-yl)-propionic acid | 533.3 | 4.13 | 1, 4, 9 |

-continued

| Entry No. | Structure | IUPAC Name | M + H (ES) | RT (min) | Methods of Preparation |
|---|---|---|---|---|---|
| 99 | 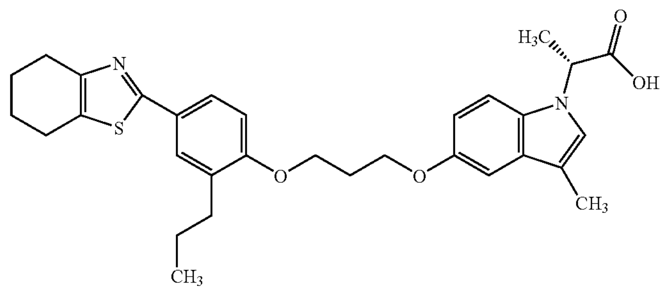 | Chiral(2R)-2-(3-methyl-5-{3-[2-propyl-4-(4,5,6,7-tetrahydro-benzothiazol-2-yl)-phenoxy]-propoxy}-indol-1-yl)-propionic acid | 533.3 | 4.13 | 1, 4, 9 |
| 100 | 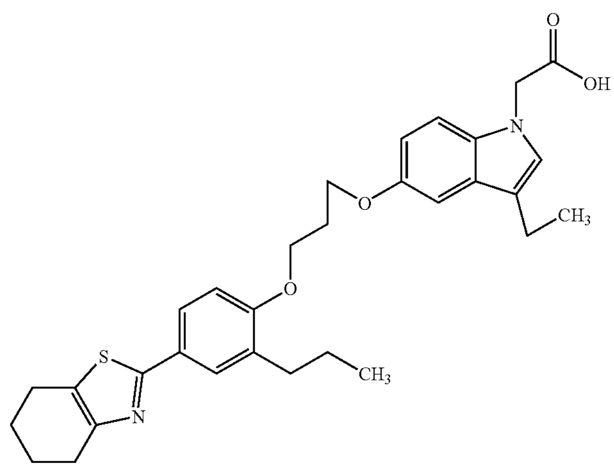 | (3-ethyl-5-{3-[2-propyl-4-(4,5,6,7-tetrahydro-benzothiazol-2-yl)-phenoxy]-propoxy}-indol-1-yl)-acetic acid | 533 | 4.43 | 1, 4, 9 |
| 101 | 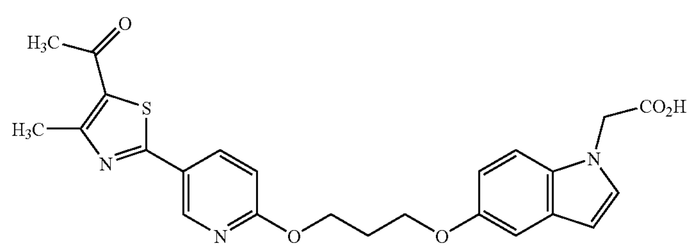 | (5-{3-[5-(5-acetyl-4-methyl-thiazol-2-yl)-pyridin-2-yloxy]-propoxy}-indol-1-yl)-acetic acid | 466 | 3.1 | 1, 12 |
| 102 | 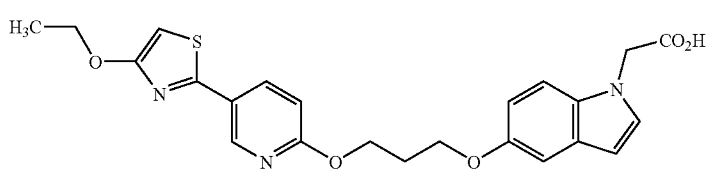 | 2-(5-{3-[5-(4-ethoxy-1,3-thiazol-2-yl)-2-pyridyloxy]propoxy}indolyl)acetic acid | 454 | 3.23 | 1, 12 |
| 103 | 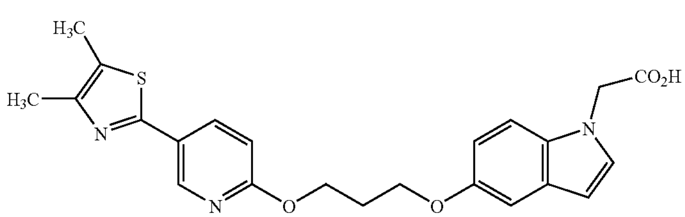 | 2-(5-{3-[5-(4,5-dimethyl-1,3-thiazol-2-yl)-2-pyridyloxy]propoxy}indolyl)acetic acid | 438.1 | 3.14 | 1, 12 |

| Entry No. | Structure | IUPAC Name | M + H (ES) | RT (min) | Methods of Preparation |
|---|---|---|---|---|---|
| 104 | 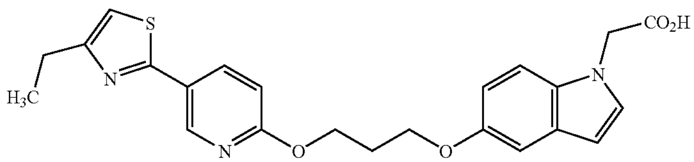 | 2-(5-{3-[5-(4-ethyl-1,3-thiazol-2-yl)-2-pyridyloxy]propoxy}indolyl)acetic acid | 438.1 | 3.26 | 1, 12 |
| 105 | 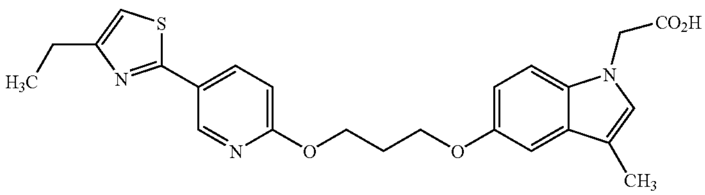 | (5-{3-[5-(4-ethyl-thiazol-2-yl)-pyridin-2-yloxy]-propoxy}-3-methyl-indol-1-yl)-acetic acid | 452 | 3.47 | 1, 14 |
| 106 | 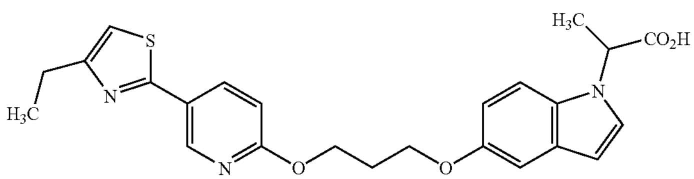 | 2-(5-{3-[5-(4-ethyl-1,3-thiazol-2-yl)-2-pyridyloxy]propoxy}indolyl)propanoic acid | 452.1 | 3.41 | 1, 12 |
| 107 | 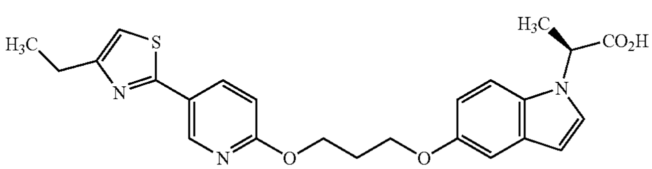 | Chiral (2S)-2-(5-{3-[5-(4-ethyl(1,3-thiazol-2-yl))(2-pyridyloxy)]propoxy}indolyl)propanoic acid | 452.1 | 3.38 | 1, 12 |
| 108 | 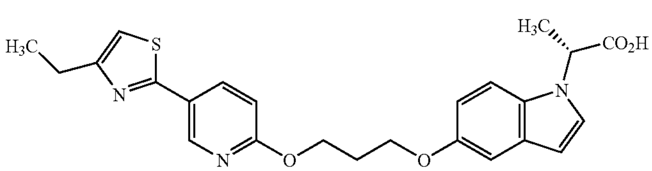 | Chiral (2R)-2-(5-{3-[5-(4-ethyl(1,3-thiazol-2-yl))(2-pyridyloxy)]propoxy}indolyl)propanoic acid | 452.1 | 3.42 | 1, 12, 13 |
| 109 | 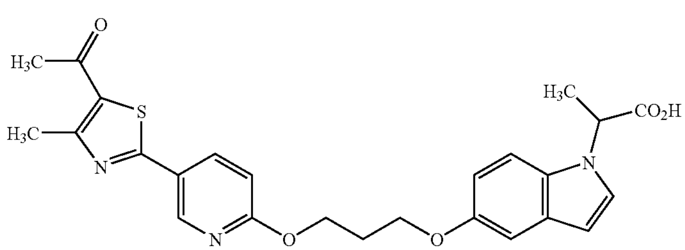 | 2-(5-{3-[5-(5-acetyl-4-methyl-1,3-thiazol-2-yl)-2-pyridyloxy]propoxy}indolyl)propanoic acid | 480 | 3.32 | 1, 12 |
| 110 | 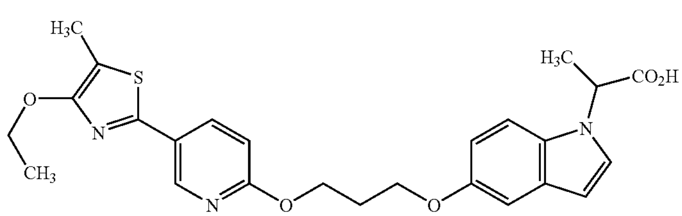 | 2-(5-{3-[5-(4-ethoxy-5-methyl-1,3-thiazol-2-yl)-2-pyridyloxy]propoxy}indolyl)propanoic acid | 482 | 3.88 | 1, 12 |

-continued

| Entry No. | Structure | IUPAC Name | M + H (ES) | RT (min) | Methods of Preparation |
|---|---|---|---|---|---|
| 111 | 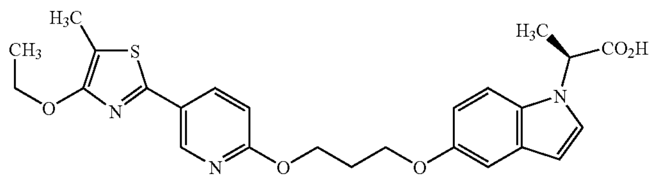 | Chiral (2S)-2-(5-{3-[5-(4-ethoxy-5-methyl-thiazol-2-yl)-pyridin-2-yloxy]-propoxy}-indol-1-yl)-propionic acid | 482 | 3.88 | 1, 12 |
| 112 | 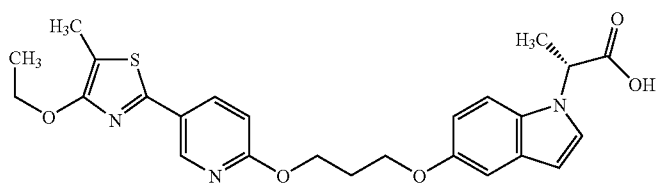 | Chiral (2R)-2-(5-{3-[5-(4-ethoxy-5-methyl-thiazol-2-yl)-pyridin-2-yloxy]-propoxy}-indol-1-yl)-propionic acid | 482 | 3.88 | 1, 12 |
| 113 | 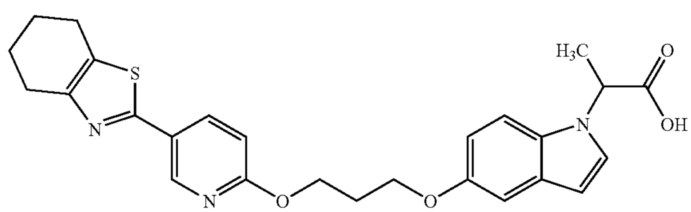 | 2-(5-{3-[5-(4,5,6,7-tetrahydro-benzothiazol-2-yl)-pyridin-2-yloxy]-propoxy}-indol-1-yl)-propionic acid | 478.2 | 2.9 | 1, 14 |
| 114 | 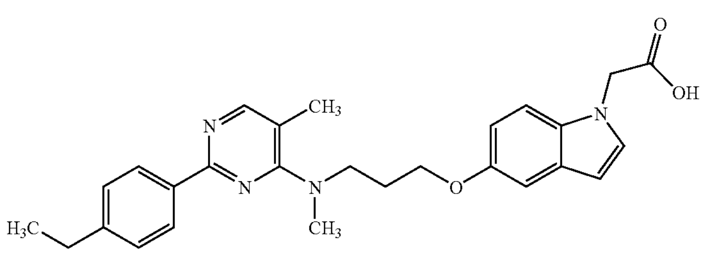 | 2-[5-(3-{[2-(4-ethylphenyl)-5-methyl-pyrimidin-4-yl]methyl-amino}propoxy)indolyl]acetic acid | 459.3 | 2.48 | 1, 15 |
| 115 | 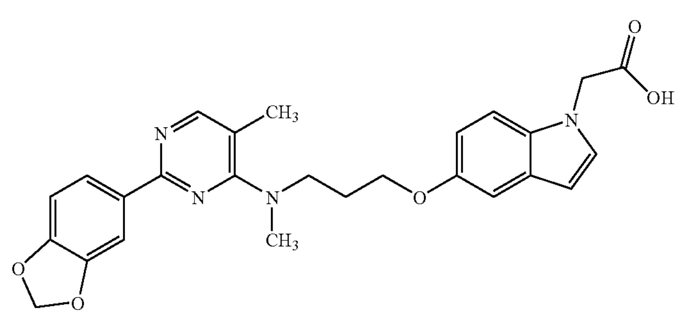 | 2-(5-{3-[(2-(2H-benzo[3,4-d]1,3-dioxolan-5-yl)-5-methylpyrimidin-4-yl)methylamino]propoxy}indolyl)acetic acid | 475.3 | 2.79 | 1, 15 |
| 116 | 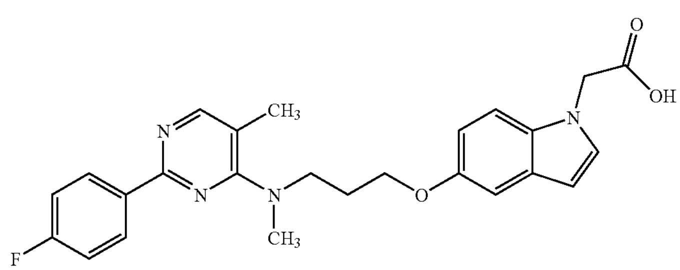 | 2-[5-(3-{[2-(4-fluorophenyl)-5-methyl-pyrimidin-4-yl]methyl-amino}propoxy)indolyl]acetic acid | 449.3 | 2.26 | 1, 16 |

| Entry No. | Structure | IUPAC Name | M + H (ES) | RT (min) | Methods of Preparation |
|---|---|---|---|---|---|
| 117 | 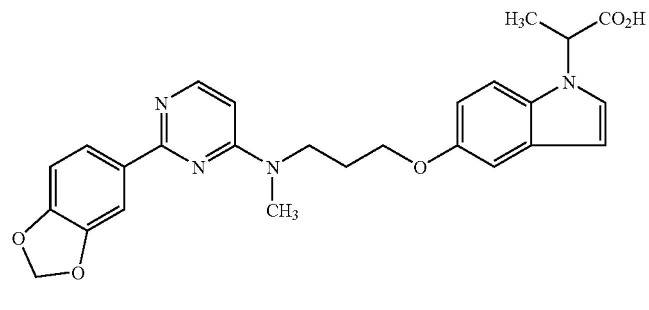 | 2-(5-{3-[(2-benzo[1,3] dioxol-5-yl-pyrimidin-4-yl)-methyl-amino]-propoxy}-indol-1-yl)-propionic acid | 475.3 | 2.26 | 1, 15 |
| 118 | 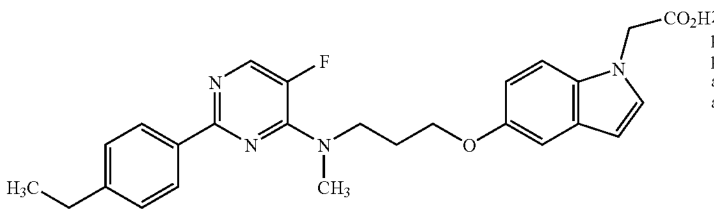 | 2-[5-(3-{[2-(4-ethyl-phenyl)-5-fluoro-pyrimidin-4-yl]methyl-amino}propoxy)indolyl] acetic acid | 463.2 | 2.28 | 1, 15 |
| 119 | 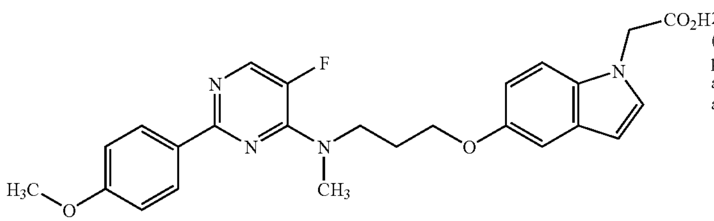 | 2-[5-(3-{[5-fluoro-2-(4-methoxyphenyl) pyrimidin-4-yl]methyl-amino}propoxy)indolyl] acetic acid | 465.2 | 2.51 | 1, 15 |
| 120 | 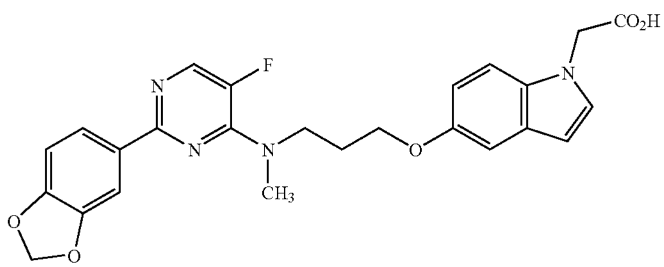 | 2-(5-{3-[(2-(2H-benzo[3,4-d]1,3-dioxolan-5-yl)-5-fluoropyrimidin-4-yl)methylamino] propoxy}indolyl)acetic acid | 479.2 | 2.6 | 1, 15 |
| 121 | 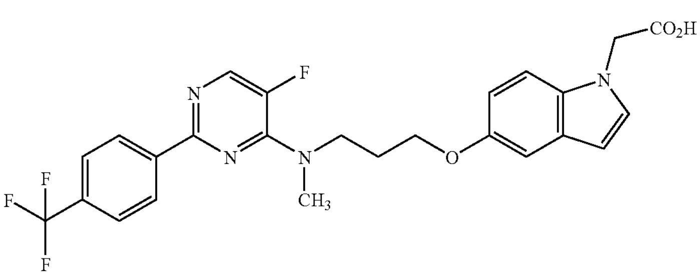 | 2-{5-[3-({5-fluoro-2-[4-(trifluoromethyl) phenyl]pyrimidin-4-yl} methylamino)propoxy] indolyl}acetic acid | 503.3 | 3.45 | 1, 15 |
| 122 | 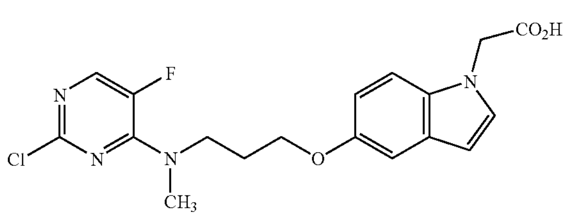 | 2-(5-{3-[(2-chloro-5-fluoropyrimidin-4-yl) methylamino]propoxy} indolyl)acetic acid | 393.2 | 2.86 | 1, 15 |

-continued

| Entry No. | Structure | IUPAC Name | M + H (ES) | RT (min) | Methods of Preparation |
|---|---|---|---|---|---|
| 123 | 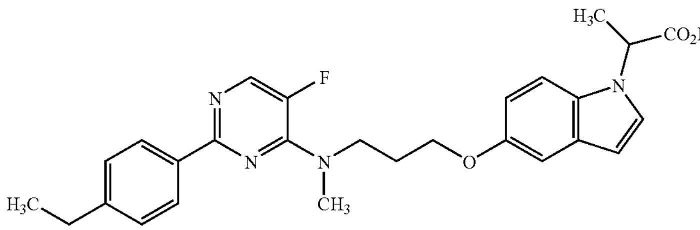 | 2-{5-[3-({5-fluoro-2-[4-(trifluoromethoxy)phenyl]pyrimidin-4-yl}methylamino)propoxy]indolyl}acetic acid | 519.3 | 3.34 | 1, 15 |
| 124 | 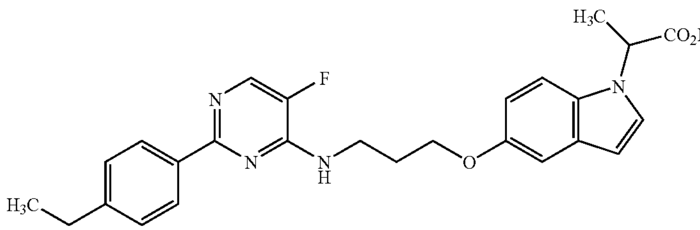 | 2-[5-(3-{[2-(4-Ethylphenyl)-5-fluoropyrimidin-4-yl]amino}propoxy)indolyl]propanoic acid | 463.4 | 2.68 | 1, 15, 17 |
| 125 | 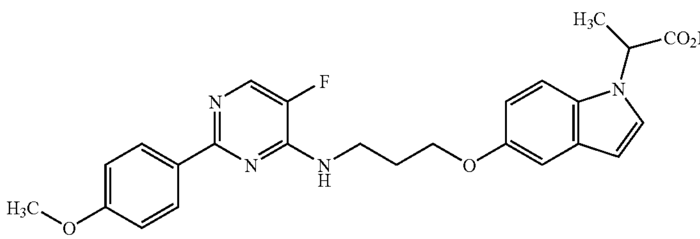 | 2-[5-(3-{[5-fluoro-2-(4-methoxyphenyl)pyrimidin-4-yl]amino}propoxy)indolyl]propanoic acid | 465.3 | 2.38 | 1, 15, 17 |
| 126 | 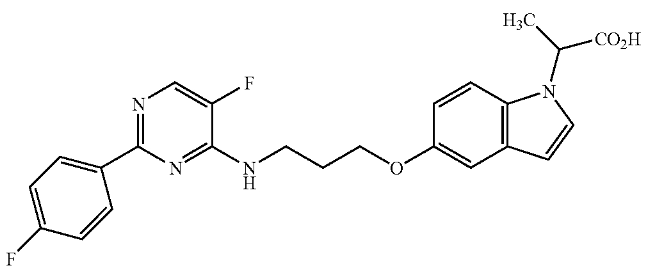 | 2-[5-(3-{[5-fluoro-2-(4-fluorophenyl)pyrimidin-4-yl]amino}propoxy)indolyl]propanoic acid | 453.1 | 2.68 | 1, 15, 17 |
| 127 | 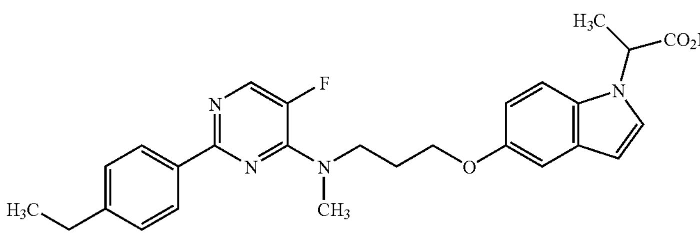 | 2-[5-(3-{[2-(4-Ethylphenyl)-5-fluoropyrimidin-4-yl]methylamino}propoxy)indolyl]propanoic acid | 477.2 | 2.72 | 1, 15, 17 |
| 128 | 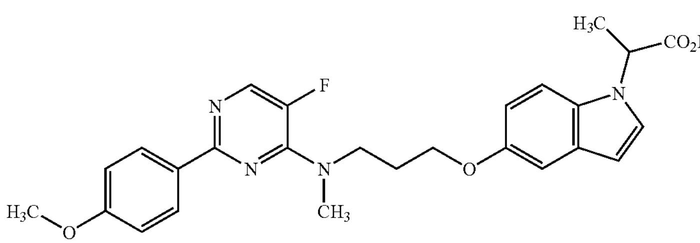 | 2-[5-(3-{[5-fluoro-2-(4-methoxyphenyl)pyrimidin-4-yl]methylamino}propoxy)indolyl]propanoic acid | 477.2 | 3.04 | 1, 15, 17 |

-continued

| Entry No. | Structure | IUPAC Name | M + H (ES) | RT (min) | Methods of Preparation |
|---|---|---|---|---|---|
| 129 | 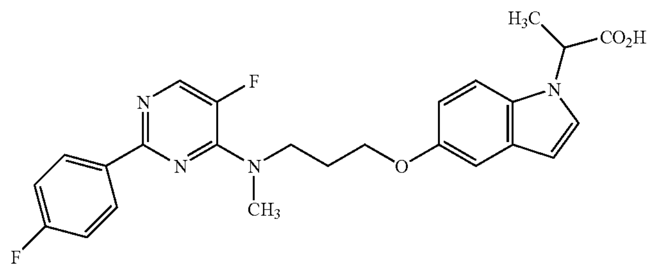 | 2-[5-(3-{[5-fluoro-2-(4-fluorophenyl)pyrimidin-4-yl]methylamino}propoxy)indolyl]propanoic acid | 467.2 | 2.99 | 1, 15, 17 |

Methods of Use

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a diabetic condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a diabetic condition or disorder severity, while avoiding or minimizing adverse side effects associated with the given therapeutic treatment.

The term "pharmaceutically acceptable" means that the subject item is appropriate for use in a pharmaceutical product.

The compounds of the present invention may be employed in the treatment of diabetes, including both type 1 and type 2 diabetes (non-insulin dependent diabetes mellitus). Such treatment may also delay the onset of diabetes and diabetic complications. The compounds may be used to prevent subjects with impaired glucose tolerance from proceeding to develop type 2 diabetes. Other diseases and conditions that may be treated or prevented using compounds of the invention in methods of the invention include: Maturity-Onset Diabetes of the Young (MODY) (Herman, et al., Diabetes 43:40, 1994); Latent Autoimmune Diabetes Adult (LADA) (Zimmet, et al., Diabetes Med. 11:299, 1994); impaired glucose tolerance (IGT) (Expert Committee on Classification of Diabetes Mellitus, Diabetes Care 22 (Supp. 1):S5, 1999); impaired fasting glucose (IFG) (Charles, et al., Diabetes 40:796, 1991); gestational diabetes (Metzger, Diabetes, 40:197, 1991); and metabolic syndrome X.

The compounds of the present invention may also be effective in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease.

The compounds of the present invention may also be useful for treating physiological disorders related to, for example, cell differentiation to produce lipid accumulating cells, regulation of insulin sensitivity and blood glucose levels, which are involved in, for example, abnormal pancreatic beta-cell function, insulin secreting tumors and/or autoimmune hypoglycemia due to autoantibodies to insulin, autoantibodies to the insulin receptor, or autoantibodies that are stimulatory to pancreatic beta-cells, macrophage differentiation which leads to the formation of atherosclerotic plaques, inflammatory response, carcinogenesis, hyperplasia, adipocyte gene expression, adipocyte differentiation, reduction in the pancreatic beta-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

Compounds of the invention may also be used in methods of the invention to treat secondary causes of diabetes (Expert Committee on Classification of Diabetes Mellitus, Diabetes Care 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenyloin, thyroid hormone, β-adrenergic agents, α-interferon and drugs used to treat HIV infection.

The compounds of the present invention may be used alone or in combination with additional therapies and/or compounds known to those skilled in the art in the treatment of diabetes and related disorders. Combination therapy includes administration of a single pharmaceutical dosage formulation which contains a compound of the present invention and one or more additional agents, as well as administration of the compound of the present invention and each additional agent in its own separate pharmaceutical dosage formulation. For example, a compound of the present invention and an agent may be administered to the patient together in a single oral dosage composition such as a tablet or capsule, or each agent may be administered in separate oral dosage formulations.

Where separate dosage formulations are used, the compound of the present invention and one or more additional agents may be administered at essentially the same time (e.g., concurrently) or at separately staggered times (e.g., sequentially).

The compounds of the invention may also be administered in combination with other known therapies for the treatment of diabetes, including PPAR ligands (agonists, antagonists), insulin secretagogues, for example sulfonylurea drugs and non-sulfonylurea secretagogues, α-glucosidase inhibitors, insulin sensitizers, hepatic glucose output lowering compounds, insulin and insulin derivatives, and anti-obesity drugs. Such therapies may be administered prior to, concurrently with or following administration of the compounds of the invention. Insulin and insulin derivatives include both long and short acting forms and formulations of insulin. PPAR ligands may include agonists and/or antagonists of any of the PPAR receptors or combinations thereof. For example, PPAR ligands may include ligands of PPAR-α, PPAR-γ, PPAR-δ or any combination of two or three of the receptors of PPAR. PPAR ligands include, for example, rosiglitazone, troglitazone, and pioglitazone. Sulfonylurea drugs include, for example, glyburide, glimepiride, chlorpropamide, tolbutamide, and glipizide. α-glucosidase inhibitors that may be useful in treating diabetes when administered with a compound of the invention include acarbose, miglitol, and voglibose. Insulin sensitizers that may be useful in treating diabetes include PPAR-γ agonists such as the glitazones (e.g., troglitazone, pioglitazone, englitazone, MCC-555, rosiglitazone, and the like) and other thiazolidinedione and non-thiazolidinedione compounds; biguanides such as metformin and phenformin; protein tyrosine phosphatase-1B (PTP-1B) inhibitors; dipeptidyl peptidase IV (DPP-IV) inhibitors, and 11beta-HSD inhibitors. Hepatic glucose output lowering compounds that may be useful in treating diabetes when administered with a compound of the invention include glucagon anatgonists and metformin, such as Glucophage and Glucophage XR. Insulin secretagogues that may be useful in treating diabetes when administered with a compound of the invention include sulfonylurea and non-sulfonylurea drugs: GLP-1, GIP, PACAP, secretin, and derivatives thereof; nateglinide, meglitnide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin.

Compounds of the invention may also be used in methods of the invention in combination with anti-obesity drugs. Anti-obesity drugs include β-3 agonists; CB-1 antagonists; neuropeptide Y5 inhibitors; appetite suppressants, such as, for example, sibutramine (Meridia); and lipase inhibitors, such as, for example, orlistat (Xenical).

Compounds of the invention may also be used in methods of the invention in combination with drugs commonly used to treat lipid disorders in diabetic patients. Such drugs include, but are not limited to, HMG-CoA reductase inhibitors, nicotinic acid, lipid lowering drugs (e.g., stanol esters, sterol glycosides such as tiqueside, and azetidinones such as ezetimibe), ACAT inhibitors (such as avasimibe), bile acid sequestrants, bile acid reuptake inhibitors, microsomal triglyceride transport inhibitors, and fibric acid derivatives. HMG-CoA reductase inhibitors include, for example, lovastatin, simvastatin, pravastatin, fluvastatin, atorvastatin, rivastatin, itavastatin, cerivastatin, and ZD4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of a cross-linked dextran.

Compounds of the invention may also be used in combination with anti-hypertensive drugs, such as, for example, β-blockers and ACE inhibitors. Examples of additional anti-hypertensive agents for use in combination with the compounds of the present invention include calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, neutral endopeptidase (NEP) inhibitors, vasopepsidase inhibitors (dual NEP-ACE inhibitors) (e.g., omapatrilat and gemopatrilat), and nitrates.

Such co-therapies may be administered in any combination of two or more drugs (e.g., a compound of the invention in combination with an insulin sensitizer and an anti-obesity drug). Such co-therapies may be administered in the form of pharmaceutical compositions, as described below.

Based on well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient (e.g., compounds) to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.0001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a therapeutically effective amount of a compound. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A therapeutically effective amount of a compound is that amount which produces a result or exerts an influence on the particular condition being treated. The compounds described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug (e.g., compound) with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC—CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for iniection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000).

It should be apparent to one of ordinary skill in the art that changes and modifications can be made to this invention without departing from the spirit or scope of the invention as it is set forth herein.

Evaluation of Compounds

In order that this invention may be better understood, the following examples are set forth. These examples are for the purpose of illustration only, and are not to be construed as limiting the scope of the invention in any manner. All publications mentioned herein are incorporated by reference in their entirety.

Demonstration of the activity of the compounds of the present invention may be accomplished through in vitro, ex vivo, and in vivo assays that are well known in the art. For example, to demonstrate the efficacy of a pharmaceutical agent for the treatment of diabetes and related disorders such as Syndrome X, impaired glucose tolerance, impaired fasting glucose, and hyperinsulinemia or atherosclerotic disease and related disorders such as hypertriglyceridemia and hypercholesteremia, the following assays may be used.

Insulin Receptor Binding in 3T3-L1 Cells Treated with Compounds

3T3-L1 cells were seeded at 9300 cells per well in Costar flat bottom TC and incubated for 1 week until they were 2 days post-confluent (e.g., cells have reached maximum density). The cells were then treated for 2 days with differentiation media (Dulbecco's Modified Eagle Medium (DMEM), 100 µg/ml Penicillin/Streptomycin, 2 mM L-Glutamine, 10% Fetal Bovine Serum) containing 0.5 µM human Insulin-like Growth Factor (IGF-1) and test compounds. After treatment, the media was replaced with differentiation media, and the cells were incubated for 4 days. The cells were then assayed for insulin receptor activity. After washing the cells with buffer, they were incubated with 0.1 nM $^{125}$I-insulin and (+/−) 100 nM unlabeled insulin, and incubated at rt for 1 hour. The cells were then washed 3× with buffer, dissolved with 1N NaOH, and counted on a gamma counter. An EC50 value was determined if a plateau was attained and percent maximum stimulation was assessed.

In Vivo Assays

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 14 days. At this point, the animals are bled again by eye or tail vein and blood glucose levels are determined. In each case, glucose levels are measured with a Glucometer Elite XL (Bayer Corporation, Elkhart, Ind.).

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (CX4) (Beckman Coulter, Fullerton, CA).

Method for Measuring Total Cholesterol, HDL-Cholesterol, Triglycerides, and Glucose Levels In another in vivo assay, obese rats are bled, then orally dosed once daily with vehicle or test compound for 4 weeks, and then bled again. Serum is analyzed for total cholesterol, HDL-cholesterol, triglycerides, and glucose using the Synchron Clinical System (CX4) (Beckman Coulter, Fullerton, CA). Lipoprotein subclass analysis is performed by NMR spectroscopy as described by Oliver et al., (*Proc. Natl. Acad. Sci. USA* 98:5306-5311, 2001).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell et al., (Am. J. Hypertens. 13:370-375, 2000).

It should be apparent to one of ordinary skill in the art that changes and modifications can be made to this invention without departing from the spirit or scope of the invention as it is set forth herein.

What is claimed is:

1. A compound of Formula (Ia)

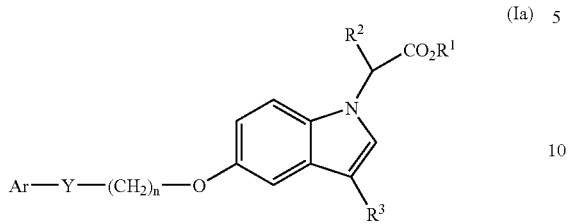

wherein
$R^1$ is H;
$R^2$ is H or $C_1$ alkyl;
$R^3$ is H or $C_1$ alkyl;
Y is O or $NR^5$;
$R^5$ is H;
n is 3;
Ar is a ring radical selected from phenyl and a 6-membered heteroaryl ring containing up to three N atoms, said Ar being optionally substituted at any available position by 1 to 5 independently selected $R^6$ groups, and optionally fused to a 5- or 6-membered saturated carbocyclic ring, a 5- or 6-membered unsaturated carbocyclic ring, or a 5- or 6-membered heterocyclic ring containing up to 3 additional heteroatoms selected from N, O, and S, wherein
said fused ring may be optionally substituted at any available position by 1-4 independently selected $R^7$ groups, with the proviso that when $R^1$, $R^2$ and $R^3$ are H, n is 3, Y is $NR^5$, wherein $R^5$ H and Ar is a 6-membered heteroaryl ring, the 6-membered heteroaryl ring contains two or three N atoms;
$R^6$ is selected from the group consisting of
  OH,
  SH,
  halo,
  CN,
  $NO_2$,
  C(=O)OH,
  (=O)—$OC_1$-$C_6$ alkyl,
  C(=O)—$OC_3$-$C_6$ cycloalkyl,
  $NR^8R^9$,
  C(=O)$NR^8R^9$,
  C(=S)$NR^8R^9$,
  $C_1$-$C_6$ alkyl optionally substituted with halo, OH, $NR^8R^9$, or $C_1$-$C_6$ alkoxy,
  $C_1$-$C_6$ haloalkyl,
  $C_1$-$C_6$ alkoxy,
  $C_1$-$C_6$ thioalkyl,
  $C_2$-$C_6$ alkenyl,
  $C_1$-$C_6$ haloalkoxy,
  $C_3$-$C_6$ cycloalkyl,
  $C_3$-$C_6$ cycloalkoxy,
  phenoxy optionally substituted on the phenyl ring with halo, $C_1$-$C_6$ alkyl, or $C_1$-$C_6$ alkoxy, and
  a mono or bicyclic ring radical selected from the group consisting of phenyl optionally fused to a 5- or 6-membered saturated or partially unsaturated carbocyclic ring, or a 5- or 6-membered saturated or partially unsaturated heterocyclic ring containing from 1-3 heteroatoms selected from N, O, and S, a 5- or 6-membered heterocyclic ring radical containing up to 4 heteroatoms selected from N, O, or S, optionally fused to a 5- or 6-membered saturated or partially unsaturated carbocyclic ring, or a 5- or 6-membered saturated or partially unsaturated heterocyclic ring containing from 1-3 heteroatoms selected from N, O, and S, said mono or bicyclic ring radical being optionally substituted with up to 5 of the following groups
  halo,
  hydroxy,
  oxo,
  CN,
  $C_1$-$C_6$ alkyl optionally substituted with halo, OH, $NR^8R^9$, or $C_1$-$C_6$ alkoxy,
  $C_1$-$C_6$ haloalkyl,
  $C_1$-$C_6$ alkoxy,
  $C_1$-$C_6$ thioalkyl
  $C_1$-$C_6$ haloalkoxy,
  $C_3$-$C_6$ cycloalkyl,
  $C_3$-$C_6$ cycloalkoxy,
  $C_1$-$C_6$ acyl,
  C(=O)OH,
  $CH_2$C(=O)OH,
  $NR^8R^9$,
  C(=O)$NR^8R^9$,
  C(=O)$OC_1$-$C_6$ alkyl, and
  C(=O)$OC_3$-$C_6$ cycloalkyl;
$R^7$ is selected from the group consisting of
  oxo,
  hydroxy,
  halo,
  CN,
  $NR^8R^9$,
  $C_1$-$C_6$ alkyl optionally substituted with OH, $NR^8R^9$, or $C_1$-$C_6$ alkoxy,
  $C_1$-$C_6$ haloalkyl,
  $C_1$-$C_6$ alkoxy,
  $C_1$-$C_6$ thioalkyl,
  $C_1$-$C_6$ haloalkoxy,
  $C_3$-$C_6$ cycloalkyl, and
  $C_3$-$C_6$ cycloalkoxy;
$R^8$ and $R^9$ are independently selected from the group consisting of
  H,
  $C_1$-$C_6$ alkyl optionally substituted with $C_3$-$C_6$ cycloalkyl,
  $C_1$-$C_6$ acyl,
  benzyl optionally substituted with halo, $C_1$-$C_6$ alkoxy, ($C_1$-$C_6$)alkyl, CN, $NH_2$, N[($C_1$-$C_3$)alkyl]$_2$, $NO_2$, or $CF_3$,
  $C_3$-$C_6$ cycloalkyl, and
  phenyl optionally substituted with halo, $C_1$-$C_6$ alkoxy, ($C_1$-$C_6$)alkyl, CN, N[($C_1$-$C_3$)alkyl]$_2$, $NO_2$, or $CF_3$,
or
$R^8$ and $R^9$ may be taken together with the nitrogen atom to which they are attached to form a 5- or 6-membered heterocyclic ring optionally interrupted by $NR^5$ or O;
or the pharmacologically acceptable esters and salts thereof.

2. The compound of claim 1, wherein
$R^1$ is H;
Y is O;
n is 3 ;
Ar is phenyl,
  said phenyl being optionally substituted at any available position by 1 to 5 independently selected $R^6$ groups, and optionally fused to a 5- or 6-membered saturated carbocyclic ring, a 5- or 6-membered unsaturated carbocyclic ring, or a 5- or 6-membered heterocyclic ring containing up to 3 additional heteroatoms selected from N, O, and S, wherein said fused ring may be optionally substituted at any available position by 1-4 independently selected $R^7$ groups;

and $R^2$, $R^3$, $R^6$, $R^7$, $R^8$, and $R^9$ are as defined in claim 1.

3. The compound of claim 2, wherein

Ar is phenyl, said phenyl being optionally substituted at any available position by 1 to 5 independently selected $R^6$ groups, and fused to a 5- or 6-membered saturated carbocyclic ring, a 5- or 6-membered unsaturated carbocyclic ring, or a 5- or 6-membered heterocyclic ring containing up to 3 additional heteroatoms selected from N, O, and S, wherein said fused ring may be optionally substituted at any available position by 1-4 independently selected $R^7$ groups.

4. The compound of claim 1, wherein $R^1$ is H;

Y is O;

n is 3;

Ar is phenyl, said phenyl being optionally substituted at any available position by 1 to 5 independently selected $R^6$ groups, and one or more substituents is a 5- or 6-membered heterocyclic ring radical containing up to 4 heteroatoms selected from N, O, or S, optionally fused to a 5- or 6-membered saturated or partially unsaturated carbocyclic ring, or a 5- or 6-membered saturated or partially unsaturated heterocyclic ring containing from 1-3 heteroatoms selected from N, O, and S, said mono or bicyclic ring radical being optionally substituted with up to 5 of the following groups halo,
hydroxy,
oxo,
CN,
$C_1$-$C_6$ alkyl optionally substituted with halo, OH, $NR^8R^9$, or $C_1$-$C_6$ alkoxy,
$C_1$-$C_6$ haloalkyl,
$C_1$-$C_6$ alkoxy,
$C_1$-$C_6$ thioalkyl
$C_1$-$C_6$ haloalkoxy,
$C_3$-$C_6$ cycloalkyl,
$C_3$-$C_6$ cycloalkoxy,
$C_1$-$C_6$ acyl,
C(=O)OH,
$CH_2$C(=O)OH,
$NR^8R^9$,
C(=O)$NR^8R^9$,
C(=O)O$C_1$-$C_6$ alkyl, and
C(=O)O$C_3$-$C_6$ cycloalkyl;

and $R^2$, $R^3$, $R^6$, $R^7$, $R^8$, and $R^9$ are as defined in claim 1.

5. The compound of claim 1, wherein $R^1$ is H;

Y is O;

n is 3;

Ar is a 6-membered heteroaryl ring containing up to three N atoms, said heteroaryl being optionally substituted at any available position by 1 to 5 independently selected $R^6$ groups, and optionally fused to a 5- or 6-membered saturated carbocyclic ring, a 5- or 6-membered unsaturated carbocyclic ring, or a 5- or 6-membered heterocyclic ring containing up to 3 additional heteroatoms selected from N, O, and S, wherein said fused ring may be optionally substituted at any available position by 1-4 independently selected $R^7$ groups;

and $R^2$, $R^3$, $R^6$, $R^7$, $R^8$, and $R^9$ are as defined in claim 1.

6. The compound of claim 1, wherein $R^1$ is H;

Y is $NR^5$;

n is 3;

Ar is a 6-membered heteroaryl ring containing up to three N atoms, said heteroaryl being substituted at any available position by 1 to 5 independently selected $R^6$ groups when the 6-membered heteroaryl ring contains one N atom and optionally substituted at any available position by 1 to 5 independently selected $R^6$ groups when the 6-membered heteroaryl ring contains two or three N atoms, and optionally fused to a 5- or 6-membered saturated carbocyclic ring, a 5- or 6-membered unsaturated carbocyclic ring, or a 5- or 6-membered heterocyclic ring containing up to 3 additional heteroatoms selected from N, O, and S, wherein said fused ring may be optionally substituted at any available position by 1-4 independently selected $R^7$ groups;

and $R^2$, $R^3$, $R^5$, $R^6$, $R^7$, $R^8$, and $R^9$ are as defined in claim 1.

7. A compound selected from the group consisting of (5-{3-[4-(4,5,6,7-tetrahydro-benzooxazol-2-yl)-phenoxy]-propoxy}-indol-1-yl)-acetic acid;

(5-{3-[4-(4-ethyl-oxazol-2-yl)-2-propyl-phenoxy]-propoxy}-indol-1-yl)-acetic acid;

(5-{3-[2-propyl-4-(4,5,6,7-tetrahydro-benzooxazol-2-yl)-phenoxy]-propoxy}-indol-1-yl)-acetic acid;

(5-{3-[4-(4-tert-butyl-oxazol-2-yl)-2-propyl-phenoxy]-propoxy}-3-methylindolyl)-acetic acid;

2-(5-{3-[4-(4-ethyl(1,3-oxazol-2-yl))-2-propylphenoxy]propoxy}-3-methylindolyl)acetic acid;

2-{3-methyl-5-[3-(2-propyl-4-(4,5,6,7-tetrahydrobenzoxazol-2-yl)phenoxy)propoxy]indolyl}propanoic acid;

2-{5-[3-(2-methoxy-4-(4,5,6,7-tetrahydrobenzothiazol-2-yl)phenoxy)propoxy]indolyl}acetic acid;

(5-{3-[4-(4-ethyl-thiazol-2-yl)-2-propyl-phenoxy]-propoxy}-indol-1-yl)-acetic acid;

2-{5-[3-(2-propyl-4-(4,5,6,7-tetrahydrobenzothiazol-2-yl)phenoxy)propoxy]indolyl}acetic acid;

2-(5-{3-[4-(4-ethoxy-5-methyl(1,3-thiazol-2-yl))-2-propylphenoxy]propoxy}indolyl)acetic acid;

2-[5-(3-{4-[5-(N,N-dimethylcarbamoyl)-4-methyl(1,3-thiazol-2-yl)]-2-propylphenoxy}propoxy)indolyl]acetic acid;

2-{5-[3-(2-propyl-4-(1,3-thiazol-2-yl)phenoxy)propoxy]indolyl}acetic acid;

(5-{3-[4-(6,7-dihydro-5H-pyrano[2,3-d]thiazol-2-yl)-2-propyl-phenoxy]-propoxy}-indol-1-yl)-acetic acid;

2-(5-{3-[4-(4,5,6,7-tetrahydro-benzothiazol-2-yl)-phenoxy]-propoxy}-indol-1-yl)-propionic acid;

(2S)-2-(5-{3-[4-(4ethoxy-5-methyl-thiazol-2-yl)-2-propyl-phenoxy]-propoxy}-indol-1-yl)-propionic acid;

(2R)-2-(5-{3-[4-(4-ethoxy-5-methyl-thiazol-2-yl)-2-propyl-phenoxy]-propoxy}-indol-1-yl)-propionic acid;

2-{3-methyl-5-[3-(2-propyl-4-(4,5,6,7-tetrahydrobenzothiazol-2-yl)phenoxy)propoxy]indolyl}acetic acid;

(2S)-2-(3-methyl-5-{3-[2-propyl-4-(4,5,6,7-tetrahydro-benzothiazol-2-yl)-phenoxy]-propoxy}-indol-1-yl)-propionic acid; and (3-ethyl-5-{3-[2-propyl-4-(4,5,6,7-tetrahydro-benzothiazol-2-yl)-phenoxy]-propoxy}-indol-1-yl)-acetic acid.

8. A pharmaceutical composition comprising a therapeutically effective amount of a compound of claim 1, or a pharmaceutically acceptable salt or ester, in combination with a pharmaceutically acceptable carrier.

9. A pharmaceutical composition comprising a therapeutically effective amount of a compound of claim 1, or a pharmaceutically acceptable salt thereof, in combination with a pharmaceutically acceptable carrier and one or more pharmaceutical agents.

10. The pharmaceutical composition of claim 9, wherein the pharmaceutical agent is PPAR ligands, insulin secretagogues, sulfonylurea drugs, α-glucosidase inhibitors, insulin sensitizers, hepatic glucose output lowering compounds, insulin and insulin derivatives, biguanides, protein tyrosine phosphatase-1B, dipeptidyl peptidase IV, 11beta-HSD inhibitors, anti-obesity drugs, HMG-CoA reductase inhibitors, nicotinic acid, lipid lowering drugs, ACAT inhibitors, bile acid sequestrants, bile acid reuptake inhibitors, microsomal triglyceride transport inhibitors, fibric acid derivatives, β-blockers, ACE inhibitors, calcium channel blockers, diuretics, renin inhibitors, AT-1 receptor antagonists, ET receptor antagonists, neutral endopeptidase inhibitors, vasopepsidase inhibitors, and nitrates.

11. A method of treating a disease or condition selected from the group consisting of diabetes (type 1 or type 2), maturity-onset diabetes of the young (MODY), latent autoimmune diabetes adult (LADA), impaired glucose tolerance (IGT), impaired fasting glucose (IFG), and gestational diabetes, comprising administering to a mammal an effective amount of a compound of claim 1.

12. The method of claim 11, further comprising administering a PPAR ligand, an insulin sensitizer, a sulfonylurea, an insulin secretagogue, a hepatic glucose output lowering compound, an α-glucosidase inhibitor, biguanides, protein tyrosine phosphatase-1B (PTP-1B) inhibitors, dipeptidyl peptidase IV, 11beta-HSD inhibitors, insulin or insulin derivatives in combination with said compound of claim 1.

13. The method of claim 11, further comprising administering an anti-obesity drug in combination with said compound of claim 1.

14. The method of claim 13, wherein the anti-obesity drug is selected from β-3 agonists, CB-1 antagonists, neuropeptide Y5 inhibitors, ciliary neurotrophic factor and derivatives, appetite suppressants, and lipase inhibitors.

15. A method of treating lipid disorders in diabetic patients, comprising administering to a mammal an effective amount of a compound of claim 1 in combination with HMG-CoA reductase inhibitors, nicotinic acid, fatty acid lowering compounds, lipid lowering drugs, ACAT inhibitors, bile acid sequestrants, bile acid reuptake inhibitors, microsomal triglyceride transport inhibitors, or fibric acid derivatives.

16. A method of treating hypertension in diabetic patients, comprising administering to a mammal an effective amount of a compound of claim 1 in combination with β-blockers, ACE inhibitors, calcium channel blockers, diuretics, renin inhibitors, AT-1 receptor antagonists, ET receptor antagonists, neutral endopeptidase (NEP) inhibitors, vasopepsidase inhibitors, and nitrates.

17. A medicament comprising a compound according to any of claims 1-6 or 7.

18. A medicament comprising a compound according to any of claims 1-6 or 7 in combination with at least one pharmaceutically acceptable, pharmaceutically safe carrier or excipient/diluent/adjuvants.

19. A medicament consisting of a compound according to any of claims 1-6 or 7 in combination with PPAR ligands, insulin secretagogues, sulfonylurea drugs, α-glucosidase inhibitors, insulin sensitizers, hepatic glucose output lowering compounds, insulin and insulin derivatives, biguanides, protein tyrosine phosphatase-1B, dipeptidyl peptidase IV, 11beta-HSD inhibitors, anti-obesity drugs, HMG-CoA reductase inhibitors, nicotinic acid, lipid lowering drugs, ACAT inhibitors, bile acid sequestrants, bile acid reuptake inhibitors, microsomal triglyceride transport inhibitors, fibric acid derivatives, β-blockers, ACE inhibitors, calcium channel blockers, diuretics, renin inhibitors, AT-1 receptor antagonists, ET receptor antagonists, neutral endopeptidase inhibitors, vasopepsidase inhibitors, and nitrates.

20. A process for preparing a medicament according to claim 18, comprising combining at least one compound according to any of claims 1-6 or 7 with at least one pharmaceutically acceptable, pharmaceutically safe carrier or excipient/diluent/adjuvants, mixing the combination and bringing the combination into a suitable administration form.

* * * * *

UNITED STATES PATENT AND TRADEMARK OFFICE
CERTIFICATE OF CORRECTION

PATENT NO.        : 7,592,361 B2
APPLICATION NO.   : 10/555024
DATED             : September 22, 2009
INVENTOR(S)       : Ma et al.

It is certified that error appears in the above-identified patent and that said Letters Patent is hereby corrected as shown below:

In the Specification:

Column 98, Entry No. 46: Please reverse -- OH -- and -- O -- as shown below:

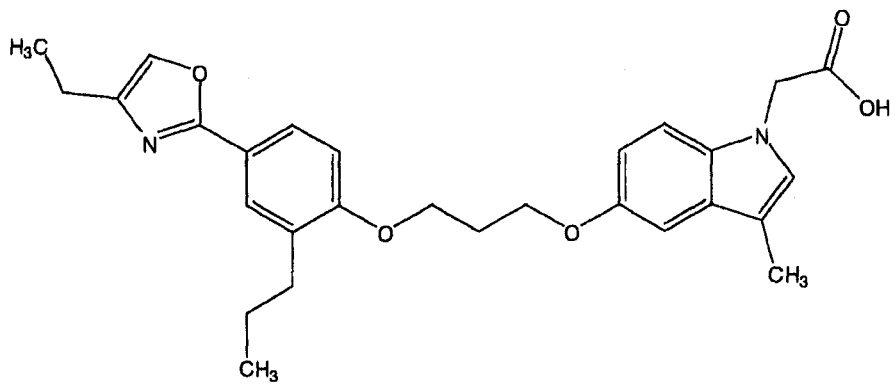

Column 98, Entry No. 48: Please correct by reversing -- OH -- and -- O -- as shown below:

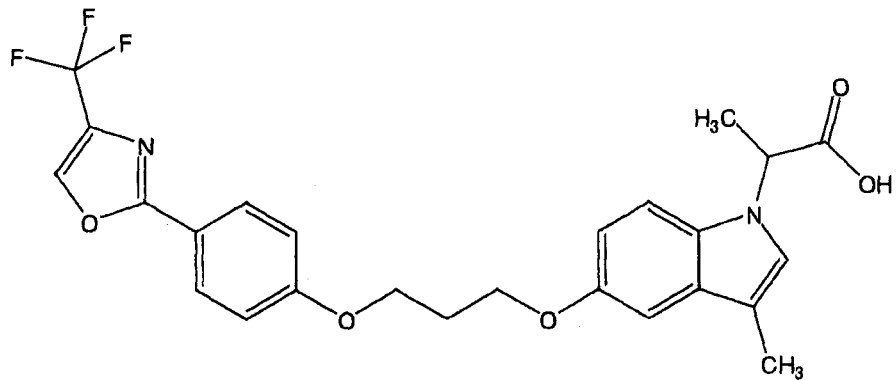

CERTIFICATE OF CORRECTION (continued)
U.S. Pat. No. 7,592,361 B2

Column 99, Entry No. 51: Please add the missing -- OH -- as shown below:

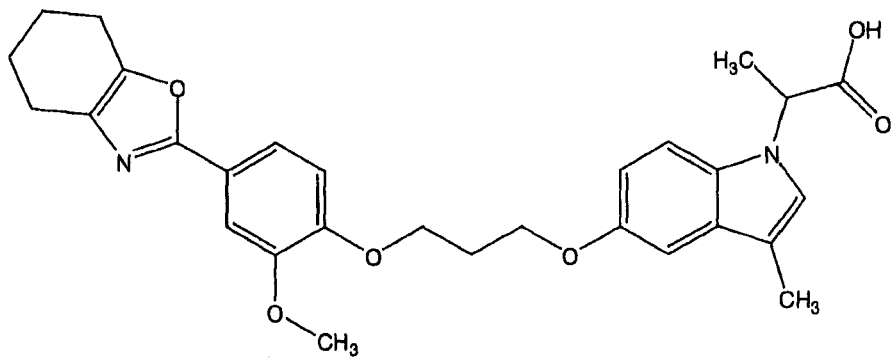

Column 112, Entry No. 83: correct "-3-methoxyphenoxy]"
to read -- -2-methoxyphenoxy] --

In the Claims:

Column 139, Claim 1, Line 34: Please correct "$R^5H$" to read -- $R^5$ is H --

Column 139, Claim 1, Line 44: Please correct "(=O)" to read -- C(=O) --

Column 142, Claim 7, Line 59: Please correct "4ethoxy" to read -- 4-ethoxy --

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,592,361 B2  Page 1 of 1
APPLICATION NO. : 10/555024
DATED : September 22, 2009
INVENTOR(S) : Ma et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 627 days.

Signed and Sealed this

Twenty-first Day of September, 2010

David J. Kappos
*Director of the United States Patent and Trademark Office*